(12) United States Patent
Boyd et al.

(10) Patent No.: US 9,217,737 B2
(45) Date of Patent: Dec. 22, 2015

(54) MULTIMEDIA EVALUATION OF BUTANOL-CONTAINING FUELS

(75) Inventors: Dennis P. Boyd, Chicago, IL (US); Theresa M. Dobel, Akron, OH (US); Don Germano, Wilmington, DE (US); Robert S. Grace, Caversham (GB); Phillip R. Greene, Reading (GB); Ken Kimura, Cypress, CA (US); Geoffrey Lulham, Pangbourne (GB); Adam Schubert, Naperville, IL (US); Ronald D. Stevens, Wilmington, DE (US); Delwyn Greene, legal representative, Lincolnshire (GB)

(73) Assignee: Butamax Advanced Biofuels LLC, Wilmington, DE (US)

(*) Notice: Subject to any disclaimer, the term of this patent is extended or adjusted under 35 U.S.C. 154(b) by 460 days.

(21) Appl. No.: 13/237,819

(22) Filed: Sep. 20, 2011

(65) Prior Publication Data

US 2012/0240454 A1    Sep. 27, 2012

Related U.S. Application Data

(60) Provisional application No. 61/384,461, filed on Sep. 20, 2010, provisional application No. 61/512,864, filed on Jul. 28, 2011.

(51) Int. Cl.
*G01N 33/28* (2006.01)
*C10L 1/02* (2006.01)

(52) U.S. Cl.
CPC ............ *G01N 33/2852* (2013.01); *C10L 1/023* (2013.01); *C10L 1/026* (2013.01)

(58) Field of Classification Search
CPC ......... C10L 1/1824; C10L 1/02; C10L 1/023; C10L 1/026; G01N 33/2852
USPC ................................................. 44/451, 452
See application file for complete search history.

(56) References Cited

U.S. PATENT DOCUMENTS

| | | | |
|---|---|---|---|
| 4,398,920 | A | 8/1983 | Guibet et al. |
| 8,465,560 | B1 | 6/2013 | Wolf |
| 8,734,543 | B2 | 5/2014 | Baustian |
| 8,870,983 | B2 | 10/2014 | Baustian et al. |
| 8,968,429 | B2 | 3/2015 | Baustian et al. |
| 2004/0123518 | A1 | 7/2004 | Eastman et al. |
| 2006/0162243 | A1 | 7/2006 | Wolf |
| 2007/0092957 | A1 | 4/2007 | Donaldson et al. |
| 2009/0099401 | A1 | 4/2009 | D'Amore et al. |
| 2009/0199464 | A1 | 8/2009 | Wolf |
| 2010/0031558 | A1 | 2/2010 | Goss et al. |
| 2010/0307053 | A1 | 12/2010 | Kuberka et al. |
| 2011/0023354 | A1 | 2/2011 | Wolf |
| 2011/0283604 | A1 | 11/2011 | Foster et al. |
| 2012/0144902 | A1 | 6/2012 | Torres-Ordonez et al. |
| 2013/0180164 | A1 | 7/2013 | Wolf |
| 2013/0227878 | A1 | 9/2013 | Wolf et al. |
| 2013/0247450 | A1 | 9/2013 | Wolf |
| 2013/0247453 | A1 | 9/2013 | Baustian et al. |
| 2014/0005443 | A1 | 1/2014 | D'Amore et al. |
| 2014/0109467 | A1 | 4/2014 | Wolf |
| 2015/0007490 | A1 | 1/2015 | Torres-Ordonez et al. |
| 2015/0007491 | A1 | 1/2015 | Baustian et al. |

FOREIGN PATENT DOCUMENTS

WO    WO2009137356    11/2009

OTHER PUBLICATIONS

California Biobutanol Multimedia Evaluation, Tier I, Jan. 2010.*
Pierce, et al., Effects of Fuel Exposure on Physical Properties of Selected Plastics, SAE Technical Paper Series, Paper No. 900632, International Congress and Exposition, Feb. 26-Mar. 2, 1990.
Thomas, Fluoroelastomer Compatibility with Bioalcohol Fuels,SAE International, No. 2009-01-0994, 2009.
Siegl, et al., Improved Emissions Speciation Methodology for Phase II of the a Research Program—Hydrocarbons and Oxygenates, SAE International, Paper No. 930142, 1993 (Abstract).
ASTM D471-06, Standard Test Method for Rubber Property—Effect of Liquids, 2006.
ASTM D790-10, Standard Test Methods for Flexural Properties of Unreinforced and Reinforced Plastics and Electrical Insulating Materials, 2010.
ASTM D1415-06, Standard Test Method for Rubber Property—International Hardness, 2006.
ASTM D1963-85, Standard Test Method for Specific Gravity of Drying Oils, Varnishes, Resins, and Related Materials at 25/25° C., 1985.
ASTM D2000-08, Standard Classification System for Rubber Products in Automotive Applications, 2008.
ASTM D2240-05, Standard Test Method for Rubber Property—Durometer Hardness, 2010.
ASTM D2583-07, Standard Test Method for Indentation Hardness of Rigid Plastics by Means of a Barcol Impressor, 2007.
ASTM D2624-09, Standard Test Methods for Electrical Conductivity of Aviation and Distillate Fuels, 2009.
ASTM D4308-95, Standard Test Method for Electrical Conductivity of Liquid Hydrocarbons by Precision Meter, 2010.
ASTM D6115-97, Standard Test Method for Mode I Fatigue Delamination Growth Onset of Unidirectional Fiber-Reinforced Polymer Matrix Composites, 2004.
International Search Report for corresponding PCT Application No. PCT/US2011/001622, dated May 7, 2012.
U.S. Appl. No. 12/469,373, filed May 20, 2009 (Butamax).
U.S. Appl. No. 14/259,611, filed Apr. 23, 2014 (Butamax).
U.S. Appl. No. 14/598,569, filed Jan. 16, 2015 (Butamax).

* cited by examiner

*Primary Examiner* — Cephia D Toomer

(57) ABSTRACT

The present invention is related to hydrocarbon compositions comprising butanol that have substantially the same or improved performance properties than comparable hydrocarbon compositions comprising ethanol and to methods for identifying such compositions.

5 Claims, 37 Drawing Sheets

| # | Item |
|---|---|
| 1 | Stainless steel chamber bottom |
| 2 | Stainless steel chamber top |
| 3 | Bleed valve |
| 4 | Thermocouple |
| 5 | 0-15 PSI Pressure gauge |
| 6 | Sampling port assembly |

Test Fuel Property Comparison (Axis on left is DVPE, psi. Axis on Right is Relative Density. Bars from L to R are Non-Oxy, E10, Bu16, E10:Bu16) RVP profile, match blending for consistent RVP across fuels.

Two Day Total Emissions of the 24 Hour California Diurnal Cycle (65°F to 105°F to 65°F). (For each rig, Bars from L to R are E0, Bu16, Bu16:E10, E10)

Top 20 Hydrocarbon Species Comparison – Non-Oxygenated Gasoline

| Baseline | Non-Oxygenated Gasoline - Baseline | | | | | | | |
|---|---|---|---|---|---|---|---|---|
| Species | Rig 1 wt% | Rig 2 wt% | Rig 3 wt% | Rig 4 wt% | Rig 5 wt% | Rig 6 wt% | Rig 7 wt% | Fuel wt% |
| Toluene | 11.94 | 11.90 | 9.26 | 18.69 | 12.57 | 12.63 | 9.67 | 4.455 |
| 2-Methylbutane (Isopentane) | 9.03 | 13.88 | 12.16 | 6.37 | 9.70 | 9.00 | 12.62 | 6.796 |
| n-Pentane | 8.04 | 9.22 | 11.20 | 5.79 | 7.59 | 7.55 | 8.93 | 4.495 |
| 2,2,4-TriMePentane (IsoOctane) | 5.23 | 3.94 | 5.70 | 3.60 | 6.00 | 6.66 | 10.84 | 13.001 |
| n-Hexane | 3.97 | 4.93 | 5.83 | 3.43 | 4.16 | 4.50 | 4.70 | 3.728 |
| Benzene | 4.89 | 4.40 | 3.41 | 6.36 | 4.10 | 4.05 | 2.82 | 1.243 |
| 1-Methyl-3-Ethylbenzene | 9.99 | 2.22 | 1.40 | 3.96 | 2.83 | 3.56 | 2.50 | 2.939 |
| 3-Methylpentane | 2.44 | 2.33 | 2.93 | 1.75 | 2.56 | 2.64 | 3.29 | 2.838 |
| 2,3,4-Trimethylpentane | 1.88 | 1.68 | 2.10 | 1.63 | 2.15 | 2.71 | 3.81 | 4.825 |
| Methylcyclopentane | 1.44 | 1.58 | 1.71 | 1.33 | 1.62 | 1.65 | 1.79 | 1.747 |
| n-Butane | 4.93 | | 6.83 | 3.33 | 4.46 | 4.15 | 7.09 | 1.627 |
| 1,2,4-TriMeBenz & t-Butylbenzene | 3.87 | 4.23 | 3.97 | 7.94 | 4.59 | | 4.50 | 6.751 |
| 2-MePentane & 4-Me-o-2-Pentene | 3.95 | 3.91 | 5.09 | 2.87 | 4.14 | | 5.33 | 4.328 |
| 2,3-Dimethylpentane | 2.09 | 1.85 | 2.38 | 1.59 | 2.29 | | 3.43 | |
| 1,3,5-Trimethylbenzene | 1.49 | 1.28 | 1.39 | 2.43 | 1.46 | 2.16 | 1.48 | 2.226 |
| 2,3-Dimethylbutane | 1.93 | 1.68 | 1.32 | | 1.26 | | 2.47 | 1.446 |
| 2,3,5-Trimethylhexane | | 6.38 | | 1.32 | | | | |
| 3-Methylnonane | | | | | | 7.05 | | |
| Cyclohexene & 3-Methylhexane | 1.19 | | 1.45 | | 1.31 | 1.37 | 1.54 | 1.732 |
| 1,3-Butadiene | | 6.77 | | | | | | |
| 2-Methylhexane | | 1.29 | | | | 3.74 | 1.44 | 5.463 |
| Ethanol | | | | | 4.19 | 1.93 | | |
| 1-Methyl-4-Ethylbenzene | | | 1.42 | 2.87 | 1.42 | | | 1.493 |
| meta- & para-Xylenes | 1.26 | | | 2.12 | 1.94 | | | 0.307 |
| Unknown #2 | | | | | | 4.22 | | |
| n-Heptane | 1.10 | 1.52 | 1.48 | | | | | 1.341 |
| 1-Ethyl-2-Methylbenzene | | | | 1.66 | | 1.36 | | |
| 2,5-DiMeHexane & EtCyPentane | | | 1.44 | | | 1.53 | | 0.847 |
| Cyclohexane | 1.17 | | | 1.45 | | | | 0.657 |
| Cyclopentane | | | | | | 1.97 | | 0.51 |
| 2,3-DiMeHexane & 2,3-MeEtPentane | | | | | | | 1.43 | 1.79 |
| 2,4-Dimethylpentane | | | | | | | 1.39 | 1.436 |
| 2-Methyl-2-butene | | 1.34 | | | | | | 0.378 |
| Components Common to all = | 58.9 | 56.1 | 55.7 | 52.9 | 53.3 | 55.0 | 61.0 | 46.1 |
| Top 20 total = | 81.8 | 86.3 | 82.5 | 80.5 | 80.4 | 84.4 | 91.1 | |
| Total Permeation, mg/48 hours = | 397.3 | 95.2 | 913.4 | 659.1 | 803.2 | 1158.8 | 1883.5 | |

FIG. 8A

Top 20 Hydrocarbon Species Comparison – 10% Ethanol Blend

| Species | 10% Ethanol Blend | | | | | | | |
|---|---|---|---|---|---|---|---|---|
| | Rig 1 wt% | Rig 2 wt% | Rig 3 wt% | Rig 4 wt% | Rig 5 wt% | Rig 6 wt% | Rig 7 wt% | Fuel wt% |
| Ethanol | 50.84 | 27.36 | 39.03 | 36.16 | 48.36 | 27.00 | 46.43 | 9.267 |
| Toluene | 9.99 | 9.61 | 7.14 | 15.06 | 11.68 | 8.66 | 9.87 | 5.821 |
| 2-Methylbutane (Isopentane) | 4.99 | 10.27 | 7.16 | 3.81 | 2.76 | 7.85 | 6.13 | 4.312 |
| n-Pentane | 3.85 | 5.94 | 7.35 | 4.11 | 3.91 | 5.85 | 5.21 | 3.533 |
| 2,2,4-TriMePentane (IsoOctane) | 3.01 | 4.52 | 5.00 | 3.92 | 3.99 | 8.22 | 3.21 | 17.542 |
| Benzene | 3.50 | 3.18 | 2.74 | 4.95 | 3.81 | 2.67 | 3.65 | 1.324 |
| n-Hexane | 2.39 | 4.04 | 3.85 | 2.91 | 1.85 | 3.48 | 2.59 | 3.296 |
| n-Butane | 1.65 | 2.60 | 3.33 | 1.93 | 2.33 | 2.63 | 2.85 | 0.953 |
| 3-Methylpentane | 1.18 | 1.53 | 1.74 | 1.41 | 0.80 | 2.10 | 1.26 | 2.318 |
| meta- & para-Xylenes | 1.35 | 1.30 | 0.82 | 2.22 | 1.68 | 1.41 | 1.23 | 1.055 |
| 1,2,4-TriMeBenz & t-Butylbenzene | 1.25 | 0.88 | 0.74 | 1.91 | 1.71 | 1.53 | 1.11 | 4.279 |
| n-Heptane | 0.68 | 1.42 | 1.19 | 1.05 | 0.72 | 1.14 | 0.75 | 1.625 |
| Methylcyclopentane | 0.84 | 0.90 | 1.08 | 1.05 | 0.64 | 1.29 | 0.84 | 1.509 |
| Cyclohexene & 3-Methylhexane | 0.69 | 0.79 | 1.04 | 0.97 | 0.78 | 1.34 | 0.71 | 1.895 |
| 2-Methylhexane | 0.61 | 1.22 | 0.94 | 0.85 | 0.60 | 1.11 | 0.61 | 3.572 |
| 2,3-Dimethylpentane | 0.53 | 0.92 | 0.80 | 0.73 | 0.62 | 1.13 | 0.53 | |
| 2-MePentane & 4-Me-o-2-Pentane | 1.95 | 3.14 | | 2.26 | 1.33 | 3.36 | 2.25 | 3.393 |
| 2,3,5-Trimethylhexane | | 5.76 | | | | | | |
| 1-Methyl-3-Ethylbenzene | 0.74 | | | 1.06 | 1.30 | 0.88 | 0.61 | 1.948 |
| Unknown #2 | | | 3.23 | | | | | |
| 2,3,4-Trimethylpentane | 0.47 | | 0.59 | 0.66 | | 1.02 | | 1.875 |
| n-Decane | | 2.06 | | | | | | |
| 1-Methyl-4-Ethylbenzene | | | | 0.71 | 0.66 | | 0.42 | 0.933 |
| 2,3-Dimethylbutane | | | | | | 0.78 | 0.45 | 0.862 |
| Cyclopentane | | | 1.18 | | | | | 0.379 |
| ortho-Xylene | | 0.97 | | | | | | 0.441 |
| t-2-Pentene | | | 0.63 | | | | | |
| 1,3,5-Trimethylbenzene | | | | | | 0.62 | | 1.375 |
| Cyclohexane | 0.44 | | | | | | | 0.625 |
| Components Common to all = | 87.3 | 76.5 | 83.9 | 83.0 | 86.3 | 77.4 | 87.0 | 62.3 |
| Top 20 total = | 90.9 | 88.4 | 89.6 | 87.7 | 90.2 | 83.5 | 90.7 | |
| Total Permeation, mg/48 hours = | 1898.9 | 123.8 | 940.4 | 1915.0 | 2106.3 | 1316.6 | 2853.4 | |

FIG. 8B

Top 20 Hydrocarbon Species Comparison – 16% Isobutanol Blend

| Component | 16% Isobutanol Blend | | | | | | | |
|---|---|---|---|---|---|---|---|---|
| | Rig 1 | Rig 2 | Rig 3 | Rig 4 | Rig 5 | Rig 6 | Rig 7 | Fuel |
| | wt% | wt% | wt% | wt% | wt% | wt% | wt% | wt% |
| iso-Butyl Alcohol | 24.88 | 8.95 | 8.01 | 19.93 | 15.40 | 14.72 | 26.38 | 17.768 |
| Toluene | 17.82 | 14.06 | 13.62 | 18.89 | 12.33 | 13.00 | 14.90 | 5.765 |
| i-Pentane | 10.41 | 5.88 | 19.66 | 10.84 | 19.80 | 14.95 | 14.91 | 9.408 |
| Benzene | 3.78 | 2.99 | 3.22 | 5.10 | 2.96 | 2.57 | 4.09 | 1.08 |
| n-Pentane | 2.63 | 3.09 | 5.07 | 2.79 | 3.52 | 3.07 | 3.51 | 1.667 |
| 2,2,4-Trimethylpentane (Iso-Octane) | 2.42 | 2.58 | 3.58 | 2.34 | 3.29 | 4.55 | 2.09 | 6.574 |
| 1,2,4-Trimethyl benzene | 2.49 | 5.84 | 2.08 | 2.75 | 2.23 | 2.77 | 1.57 | 3.97 |
| n-Butane | 2.00 | 2.13 | 3.90 | 1.93 | 3.95 | 2.11 | 3.11 | 0.77 |
| n-Hexane | 1.87 | 1.73 | 3.06 | 1.91 | 1.92 | 2.24 | 1.90 | 1.616 |
| 1-Methyl-3-ethylbenzene | 1.75 | 2.78 | 1.68 | 2.32 | 1.95 | 2.25 | 1.38 | 2.408 |
| meta- & para-Xylenes | 2.40 | 2.21 | 1.68 | 2.33 | 1.48 | 1.63 | 1.53 | 0.881 |
| 2,3,4-Trimethylpentane | 1.22 | 1.20 | 1.77 | 1.30 | 1.53 | 2.43 | 1.05 | 3.295 |
| n-Heptane | 1.25 | 1.09 | 1.96 | 1.32 | 1.11 | 1.45 | 1.03 | 1.542 |
| 1-Methyl-4-ethylbenzene | 0.98 | 1.14 | 0.88 | 1.16 | 0.97 | 1.01 | 0.69 | 1.061 |
| 2,3-Dimethylbutane | 0.77 | | 2.01 | 1.20 | 1.68 | 1.83 | 1.37 | 1.518 |
| 4-Methylheptane | 1.22 | | 1.91 | 1.20 | 1.48 | 1.72 | 1.25 | 0.379 |
| 2-Methylhexane | 1.01 | | 1.57 | 1.08 | 1.11 | 1.49 | 0.91 | 4.178 |
| 2,4-Dimethylpentane | 0.69 | | 1.38 | 0.95 | 1.11 | 1.44 | 0.90 | 1.624 |
| 1,3,5-Trimethylbenzene | | 2.22 | 0.78 | 0.88 | 0.70 | 1.03 | 0.52 | 1.202 |
| 2-Methylbutene-2 | | | 0.98 | 0.73 | 0.74 | | 0.82 | 0.312 |
| 1,2,3-Trimethylbenzene | | 1.80 | | | | | | 0.87 |
| 3-Methylheptane | | 1.50 | | | | | | 0.785 |
| n-Propylbenzene | | 1.15 | | | | | | 0.679 |
| 2-Methylheptane | | 1.12 | | | | | | 0.62 |
| 1,4-Dimechyl-2-ethylbenzene | | 0.96 | | | | | | 0.23 |
| 2,4-Dimethylhexane | | | | | | 0.92 | | 0.834 |
| Ethylbenzene | 0.69 | | | | | | | 0.298 |
| 2,3-Dimethylhexane | 0.67 | | | | | | | 0.779 |
| Components Common to all = | 75.9 | 55.7 | 70.2 | 74.9 | 72.4 | 68.8 | 78.2 | 57.8 |
| Top 20 total = | 80.9 | 64.4 | 78.8 | 81.0 | 79.2 | 77.2 | 83.9 | |
| Total Permeation, mg/48 hours = | 632.0 | 86.3 | 681.8 | 1823.3 | 1685.1 | 996.0 | 1925.1 | |

FIG. 8C

Top 20 Hydrocarbon Species Comparison – 50:50 Blend

| Component | 50:50 Blend of E10 and Bu16 | | | | | | | |
|---|---|---|---|---|---|---|---|---|
| | Rig 1 | Rig 2 | Rig 3 | Rig 4 | Rig 5 | Rig 6 | Rig 7 | Fuel |
| | wt% | wt% | wt% | wt% | wt% | wt% | wt% | wt% |
| Ethanol | 27.34 | 14.22 | 14.21 | 22.97 | 19.96 | 8.60 | 34.07 | 4.062 |
| Toluene | 12.83 | 11.77 | 9.28 | 14.39 | 14.24 | 14.40 | 11.24 | 5.97 |
| iso-Butyl Alcohol | 12.33 | 4.33 | 4.26 | 10.08 | 10.33 | 9.29 | 11.82 | 9.972 |
| i-Pentane | 6.52 | 12.90 | 13.62 | 6.33 | 7.05 | 5.48 | 5.99 | 6.81 |
| 2,2,4-Trimethylpentane | 2.78 | 3.89 | 4.38 | 2.87 | 4.33 | 8.41 | 2.06 | 12.246 |
| n-Pentane | 3.20 | 4.01 | 6.38 | 3.01 | 3.41 | 3.51 | 2.86 | 2.558 |
| Benzene | 3.58 | 2.73 | 2.58 | 3.72 | 3.45 | 3.05 | 3.17 | 1.167 |
| meta- & para-Xylenes | 2.77 | 2.07 | 2.09 | 3.22 | 3.01 | 3.33 | 2.44 | 1.601 |
| n-Hexane | 1.79 | 2.95 | 3.24 | 2.05 | 2.17 | 2.53 | 1.57 | 2.219 |
| 1,2,4-Trimethyl benzene | 1.81 | 1.71 | 1.65 | 2.11 | 1.74 | 2.47 | 1.97 | 3.645 |
| 3-Methylpentane | 1.04 | 2.12 | 1.98 | 1.23 | 1.37 | 1.52 | 0.87 | 1.896 |
| n-Heptane | 0.85 | 1.44 | 1.19 | 0.92 | 1.02 | 1.48 | 0.65 | 1.452 |
| 2-Methylhexane | 0.82 | 1.09 | 1.33 | 0.92 | 1.09 | 1.65 | 0.62 | 4.074 |
| n-Butane | 1.56 | 5.49 | 5.50 | 2.36 | 2.29 | | 2.35 | 1.291 |
| 2-Methylpentane | | 3.48 | 3.28 | 1.94 | 2.14 | 2.20 | 1.41 | 2.744 |
| 1-Methyl-3-ethylbenzene | 1.27 | | 1.14 | 2.71 | 1.83 | 1.86 | 1.18 | 1.995 |
| 2,3,4-Trimethylpentane | 0.73 | 1.26 | 1.03 | 0.82 | 1.12 | 2.10 | | 2.651 |
| 2,3-Dimethylbutane | | 1.64 | 1.59 | 0.72 | 1.10 | 1.14 | 0.72 | 1.226 |
| 1-Methyl-4-ethylbenzene | 0.63 | 2.05 | | 1.02 | 0.84 | | 0.73 | 0.909 |
| 1,3,5-Trimethylbenzene | | 2.65 | | 0.75 | | 1.07 | 0.60 | 1.162 |
| 2,4-Dimethylpentane | | | 0.87 | | 0.69 | 1.07 | | 1.234 |
| Cyclohexane | | 1.43 | | | | | | 0.27 |
| o-Xylene | 0.65 | | | | | | 0.56 | 0.618 |
| 3-Methylheptane | | | | | | 1.01 | | 0.948 |
| 2-Methylbutene-2 | | | 0.90 | | | | | 0.347 |
| Cyclopentane | 0.82 | | | | | | | 0.248 |
| Ethylbenzene | 0.62 | | | | | | | 0.468 |
| | 20 | 20 | 20 | 20 | 20 | 20 | 20 | 27 |
| Components Common to all = | 77.7 | 65.3 | 66.2 | 73.8 | 73.2 | 65.7 | 79.3 | 57.7 |
| Top 20 total = | 83.9 | 83.2 | 80.5 | 84.1 | 83.2 | 76.2 | 86.9 | |
| Total Permeation, mg/48 hours = | 863.9 | 113.5 | 1040.1 | 2173.4 | 2217.4 | 756.2 | 2542.9 | |

FIG. 8D

Impact on Aromatic Emissions

| Benzene | E0 | mg/48 hrs E10 | Bu16 | E10:Bu16 |
|---|---|---|---|---|
| Rig 1 | 14.5 | 66.4 | 27.2 | 34.8 |
| Rig 2 | 4.2 | 3.9 | 3.4 | 3.4 |
| Rig 3 | 31.2 | 25.7 | 25.9 | 31.0 |
| Rig 4 | 41.9 | 94.7 | 106.2 | 89.2 |
| Rig 5 | 32.9 | 80.4 | 58.7 | 85.3 |
| Rig 6 | 46.9 | 35.2 | 30.1 | 27.1 |
| Rig 7 | 53.1 | 104.0 | 88.8 | 87.9 |

| Toluene | E0 | mg/48 hrs E10 | Bu16 | E10:Bu16 |
|---|---|---|---|---|
| Rig 1 | 55.5 | 189.8 | 128.2 | 124.9 |
| Rig 2 | 11.3 | 11.9 | 16.2 | 14.8 |
| Rig 3 | 84.6 | 67.2 | 109.2 | 111.5 |
| Rig 4 | 123.2 | 285.4 | 393.8 | 345.3 |
| Rig 5 | 101.0 | 246.1 | 244.4 | 351.9 |
| Rig 6 | 146.4 | 114.0 | 152.2 | 128.1 |
| Rig 7 | 182.2 | 281.6 | 323.5 | 311.8 |

FIG. 8E

Reactivity Summary

Diurnal Speciation Results - Total All Non Zero Species

| Rig No. | Test No. | Fuel | Total VOC | Total Ozone | Reactivity | Fleet Average |
|---|---|---|---|---|---|---|
| Rig 1 | 7678 | E0 | 297.3 | 963.4 | 3.241 | |
| Rig 2 | 7656 | E0 | 95.2 | 325.5 | 3.419 | |
| Rig 3 | 7687 | E0 | 913.4 | 2,436.5 | 2.667 | |
| Rig 4 | 7697 | E0 | 659.1 | 2,341.4 | 3.553 | |
| Rig 5 | 7734 | E0 | 803.2 | 2,332.2 | 2.904 | |
| Rig 6 | 7736 | E0 | 1,158.8 | 3,123.2 | 2.695 | |
| Rig 7 | 7728 | E0 | 1,883.5 | 4,350.5 | 2.310 | 2.968 |
| Rig 1 | 7880 | E10 | 1,898.9 | 4,102.3 | 2.160 | |
| Rig 2 | 7825 | E10 | 123.8 | 270.9 | 2.188 | |
| Rig 3 | 7851 | E10 | 940.4 | 1,976.9 | 2.102 | |
| Rig 4 | 7835 | E10 | 1,915.0 | 4,748.2 | 2.479 | |
| Rig 5 | 7867 | E10 | 2,106.3 | 4,857.2 | 2.306 | |
| Rig 6 | 7868 | E10 | 1,316.6 | 3,054.6 | 2.320 | |
| Rig 7 | 7845 | E10 | 2,853.4 | 6,097.9 | 2.137 | 2.242 |
| Rig 1 | 7960 | Bu16 | 719.1 | 2,106.8 | 2.930 | |
| Rig 2 | 7955 | Bu16 | 115.3 | 413.8 | 3.589 | |
| Rig 3 | 7958 | Bu16 | 802.1 | 2,148.5 | 2.678 | |
| Rig 4 | 7944 | Bu16 | 2,064.4 | 6,408.9 | 3.075 | |
| Rig 5 | 7940 | Bu16 | 1,983.2 | 5,355.9 | 2.701 | |
| Rig 6 | 7963 | Bu16 | 1,170.7 | 3,264.8 | 2.789 | |
| Rig 7 | 7953 | Bu16 | 2,171.3 | 6,039.1 | 2.781 | 2.934 |
| Rig 1 | 8013 | E10-Bu16 | 973.7 | 2,660.5 | 2.732 | |
| Rig 2 | 8005 | E10-Bu16 | 125.7 | 335.3 | 2.667 | |
| Rig 3 | 8014 | E10-Bu16 | 1,201.2 | 3,021.8 | 2.515 | |
| Rig 4 | 7992 | E10-Bu16 | 2,400.1 | 6,856.1 | 2.857 | |
| Rig 5 | 8000 | E10-Bu16 | 2,471.4 | 6,789.8 | 2.747 | |
| Rig 6 | 8023 | E10-Bu16 | 889.4 | 2,601.7 | 2.925 | |
| Rig 7 | 8006 | E10-Bu16 | 2,774.7 | 7,159.1 | 2.580 | 2.718 |

FIG. 9

MULTIMEDIA EVALUATION OF BUTANOL-CONTAINING FUELS

CROSS-REFERENCE TO RELATED APPLICATIONS

This application claims the benefit of U.S. Provisional Application No. 61/384,461, filed Sep. 20, 2010 and U.S. Provisional Application No. 61/512,864, filed Jul. 28, 2011, which are incorporated herein by reference in their entireties.

BACKGROUND OF THE INVENTION

1. Field of the Invention

The invention generally relates to alternative energy sources and fuels. More specifically, the invention relates to methods for multimedia evaluation of butanol-containing fuels, including comparing such fuels to an ethanol-containing fuel standard.

2. Background of the Invention

Global demand for liquid transportation fuel is projected to strain the ability to meet certain environmentally driven goals, for example, the conservation of oil reserves. Such demand has driven the development of technology which allows utilization of renewable resources to mitigate the depletion of oil reserves. This invention addresses the need for improved alternative fuel compositions and processes which allow for the conservation of oil reserves. Such compositions and processes would satisfy both fuel demands and environmental concerns.

Ethanol is routinely blended with both finished gasoline and gasoline subgrades (e.g., blendstocks for oxygenate blending) to make fuel blends. Butanol is an important industrial chemical that is also suitable for use in fuel blends. Butanol may be made through chemical synthesis or by fermentation. Recombinant microbial production hosts, expressing a 1-butanol biosynthetic pathway (Donaldson et al., U.S. Appl. Pub. No. 2008/0182308), a 2-butanol biosynthetic pathway (Donaldson et al., U.S. Appl. Pub. Nos. 2007/0259410 and 2007/0292927), and an isobutanol biosynthetic pathway (Maggio-Hall et al., U.S. Appl. Pub. No. 2007/0092957) have been described.

The use of butanol in fuel blends has several advantages over the use of ethanol. For example, because butanol has energy content closer to that of gasoline, consumers face less of a compromise on fuel economy by using a butanol-containing fuel. Butanol is also advantageous because it yields only $CO_2$ and little or no $SO_X$ or $NO_X$ when burned in the standard internal combustion engine, and is less corrosive than ethanol. Also, butanol has a lower vapor pressure than ethanol, meaning that it can be easily added to conventional gasoline and does not require automakers to compromise on performance to meet environmental regulations. Butanol has a blending Reid vapor pressure (RVP) of 5.1 psia, which is considerably lower than that of ethanol (blending RVP of 19 psia). As a result, butanol offers enhanced value to refiners who are typically RVP-constrained during summer blending season. The lower vapor pressure of butanol also means that it can be used in higher blend concentrations than ethanol without requiring especially adapted vehicles.

In addition, butanol fuel blends are less susceptible to separation in the presence of water than ethanol fuel blends. Furthermore, butanol's chemical properties also allow it to be blended at least 16% by volume in gasoline, thereby displacing more gasoline per gallon of fuel consumed than the standard 10% by volume ethanol blend. The water-solubility and corrosivity of butanol is also sufficiently low such that butanol-containing fuels can be transported in existing pipelines without risk of phase separation.

Butanol-containing fuels with up to 3.7 wt % oxygen (approximately 16 vol % of butanol) and meeting certain additional requirements have been approved by the U.S. Environmental Protection Agency as substantially similar to baseline gasoline under terms of the Octamix Waiver issued under §211(f) of the Clean Air Act Amendments [53 FR 3636 (2/8/88)]. However, there is a need to further determine the automotive performance parameters of such butanol-containing fuels.

Ethanol-containing fuels can have a detrimental effect on automotive materials and components. Pierce et al., "Effects of Fuel Exposure on Physical Properties of Selected Plastics," SAE International, International Congress and Exposition (1990); Shiotani et al., "Research About Applicability of Biomass Ethanol for Motor Fuel," Society of Automotive Engineers of Japan, Academic Lecture Meeting, May 20, 2005. However, only limited information about the effects of butanol-containing fuels on automotive materials and components is available.

BRIEF SUMMARY OF THE INVENTION

The present invention is related to hydrocarbon compositions comprising butanol that have substantially the same or improved performance properties than comparable hydrocarbon compositions comprising ethanol and to methods for identifying such compositions. In one aspect, the compositions of the invention are compatible with automotive materials. In another aspect, the invention is related to a hydrocarbon composition having at least about 12% renewable components comprising butanol, wherein the composition is capable of being used with an elastomer, and wherein the change in durometer hardness of the elastomer upon contact with the composition is substantially the same or less than the change in durometer hardness of the elastomer upon contact with a hydrocarbon composition comprising no more than about 10% ethanol. In another aspect, the invention is related to a hydrocarbon composition having at least about 12% renewable components comprising butanol, wherein the composition is capable of being used with an elastomer, wherein the elastomer has a durometer hardness of from about 20 to about 90 units after contact with the composition. In another aspect, the invention relates to a hydrocarbon composition having at least about 12% renewable components comprising butanol, wherein the composition is capable of being used with an elastomer, wherein the elastomer has a change in durometer hardness of less than about 6% after contact with the composition. In another aspect, the composition is compatible with the elastomer.

In one aspect, the invention relates to a hydrocarbon composition having at least about 12% renewable components comprising butanol, wherein the composition is capable of being used with an elastomer, wherein the change in tensile strength of the elastomer upon contact with the composition is substantially the same or less than the change in tensile strength of the elastomer upon contact with a hydrocarbon composition comprising no more than about 10% ethanol. In another aspect, the invention relates to a hydrocarbon composition having at least about 12% renewable components comprising butanol, wherein the composition is capable of being used with an elastomer, wherein the elastomer has a change in tensile strength or elongation of less than about 70% after contact with the composition.

In one aspect, the invention relates to a hydrocarbon composition having at least about 12% renewable components comprising butanol, wherein the composition is capable of being used with an elastomer, wherein the change in hardness of the elastomer upon contact with the composition is substantially the same or less than the change in hardness of the elastomer upon contact with a hydrocarbon composition comprising no more than about 10% ethanol. In another aspect, the invention relates to a hydrocarbon composition having at least about 12% renewable components comprising butanol, wherein the composition is capable of being used with an elastomer, wherein the elastomer has a change in hardness of less than about 20% after contact with the composition.

In one aspect, the invention relates to a hydrocarbon composition having at least about 12% renewable components comprising butanol, wherein the composition is capable of being used with an elastomer, wherein the change in volume of the elastomer upon contact with the composition is substantially the same or less than the change in volume of the elastomer upon contact with a hydrocarbon composition comprising no more than about 10% ethanol. In another aspect, the invention relates to a hydrocarbon composition having at least about 12% renewable components comprising butanol, wherein the composition is capable of being used with an elastomer, wherein the elastomer has a change in volume of less than about 160% after contact with the composition.

In one aspect, the invention relates to a hydrocarbon composition having at least about 12% renewable components comprising butanol, wherein the composition is capable of being used with an elastomer, wherein the change in mass of the elastomer upon contact with the composition is substantially the same or less than the change in mass of the elastomer upon contact with a hydrocarbon composition comprising no more than about 10% ethanol. In another aspect, the invention relates to a hydrocarbon composition having at least about 12% renewable components comprising butanol, wherein the composition is capable of being used with an elastomer, wherein the change in indentation hardness of the elastomer upon contact with the composition is substantially the same or less than the change in indentation hardness of the elastomer upon contact with a hydrocarbon composition comprising no more than about 10% ethanol. In another aspect, the invention relates to a hydrocarbon composition having at least about 12% renewable components comprising butanol, wherein the composition is capable of being used with an elastomer, wherein the elastomer has an indentation hardness of from about 30 to about 65 units of Barcol hardness after contact with the composition.

In one aspect, the invention relates to a hydrocarbon composition having at least about 12% renewable components comprising butanol, wherein the composition is capable of being used with an elastomer, wherein the change in international hardness of the elastomer upon contact with the composition is substantially the same or less than the change in international hardness of the elastomer upon contact with a hydrocarbon composition comprising no more than about 10% ethanol. In another aspect, the invention relates to a hydrocarbon composition comprising at least about 12% renewable components comprising butanol, wherein the composition is capable of being used with an elastomer, wherein the elastomer has an international hardness of from about 10 to about 100 International Rubber Hardness Determination (IRHD) units after contact with the composition.

In one aspect of the invention, the durometer hardness of an elastomer is measured according to ASTM D2240. In another aspect, the elongation, hardness, volume and/or mass of an elastomer is measured according to ASTM D471. In another aspect, the indentation hardness of an elastomer is measured according to ASTM D2583. In another aspect, the international hardness of an elastomer is measured according to ASTM D1415.

In another aspect, the elastomer comprises FKM fluoroelastomer, ethylene oxide copolymer, VQM fluorosilicone rubber, hydrogenated acrylonitrile butadiene rubber, acrylonitrile butadiene rubber, silicon rubber, chlorinated polyethylene, chloroprene rubber, styrene butadiene rubber, terpolymer of ethylene propylene diene monomer rubber, vulcanized rubber, or thermoplastic elastomer. In another aspect, the elastomer comprises chlorinated polyethylene, epichlorohydride, chlorosulfonated polyethylene synthetic rubber, or fluoropolymer elastomer. In another aspect, the elastomer comprises styrene-acrylonitrile, unsaturated polyester resin, or polyester laminate. In another aspect, the composition is compatible with the elastomer.

In one aspect, the invention relates to a hydrocarbon composition having at least about 12% renewable components comprising butanol, wherein the composition is capable of being used with a fiberglass tank resin or sealant, wherein the change in durometer hardness of the resin or sealant upon contact with the composition is substantially the same or less than the change in durometer hardness of the resin or sealant upon contact with a hydrocarbon composition comprising no more than about 10% ethanol. In another aspect, the invention relates to a hydrocarbon composition having at least about 12% renewable components comprising butanol, wherein the composition is capable of being used with a fiberglass tank resin or sealant, wherein the resin or sealant has a change in durometer hardness of from about 20 to about 90 units after contact with the composition. In another aspect, the invention relates to a hydrocarbon composition having at least about 12% renewable components comprising butanol, wherein the composition is capable of being used with a fiberglass tank resin or sealant, wherein the resin or sealant has a change in durometer hardness of less than about 6% after contact with the composition.

In one aspect, the invention relates to a hydrocarbon composition having at least about 12% renewable components comprising butanol, wherein the composition is capable of being used with a fiberglass tank resin or sealant, wherein the change in indentation hardness of the resin or sealant upon contact with the composition is substantially the same or less than the change in indentation hardness of the resin or sealant upon contact with a hydrocarbon composition comprising no more than about 10% ethanol. In another aspect, the invention relates to a hydrocarbon composition having at least about 12% renewable components comprising butanol, wherein the composition is capable of being used with a fiberglass tank resin or sealant, wherein the resin or sealant has an indentation hardness of from about 30 to about 65 units of Barcol hardness after contact with the composition.

In one aspect, the invention relates to a hydrocarbon composition having at least about 12% renewable components comprising butanol, wherein the composition is capable of being used with a fiberglass tank resin or sealant, wherein the change in flexural strength of the resin or sealant upon contact with the composition is substantially the same or less than the change in flexural strength of the resin or sealant upon contact with a hydrocarbon composition comprising no more than about 10% ethanol. In another aspect, the invention relates to a hydrocarbon composition comprising at least about 12% renewable components comprising butanol, wherein the composition is capable of being used with a fiberglass tank resin or sealant, wherein the resin or sealant has a flexural strength of from about $10 \times 10^3$ to about $30 \times 10^3$ psi after contact with the composition.

In one aspect, the invention relates to a hydrocarbon composition having at least about 12% renewable components comprising butanol, wherein the composition is capable of being used with a fiberglass tank resin or sealant, wherein the resin or sealant has substantially no visual signs of leaching or delamination after contact with the composition. In another aspect, the invention relates to a hydrocarbon composition comprising at least about 12% renewable components comprising butanol, wherein the composition is capable of being used with a fiberglass tank resin or sealant, wherein the change in volume of the resin or sealant upon contact with the composition is substantially the same or less than the change in volume of the resin or sealant upon contact with a hydrocarbon composition comprising no more than about 10% ethanol. In another aspect, the invention relates to a hydrocarbon composition comprising at least about 12% renewable components comprising butanol, wherein the composition is capable of being used with a fiberglass tank resin or sealant, wherein the resin or sealant has a change in volume of less than about 160% after contact with the composition.

In one aspect, the invention relates to a hydrocarbon composition having at least about 12% renewable components comprising butanol, wherein the composition is capable of being used with a fiberglass tank resin or sealant, wherein the change in mass of the resin or sealant upon contact with the composition is substantially the same or less than the change in mass of the resin or sealant upon contact with a hydrocarbon composition comprising no more than about 10% ethanol.

In one aspect, the durometer hardness of the resin or sealant is measured according to ASTM D2240, the indentation hardness of the resin or sealant is measured according to ASTM D2583, the flexural strength of the resin or sealant is measured according to ASTM D790, and/or the volume or mass of the resin or sealant is measured according to ASTM D471.

In one aspect of the invention, the resin or sealant has high density polyethylene (HDP), fluorinated HDP, polypropylene, acetal homopolymer, acetal copolymer, polyethylene terephthalate polyester, polyethylene terephthalate glycol copolyester, polybutylene terephthalate polyester, cork, nylon, polyvinylidene fluoride, polytetrafluoroethylene, polyphenylene sulfide, isophthalic polyester resin, terephthalic polyester resin, epoxy novolac vinyl ester resin, epoxy resin, polythiourea, or nitrile. In another aspect, the composition is compatible with the resin or sealant.

In one aspect, the invention relates to a hydrocarbon composition having at least about 12% renewable components comprising butanol, wherein the electrical conductivity of the composition is substantially the same or less than the electrical conductivity of a hydrocarbon composition comprising no more than about 10% ethanol. In another aspect, the invention relates to a hydrocarbon composition having at least about 12% renewable components comprising butanol, wherein the composition has an electrical conductivity that does not cause static build-up, static discharge, or galvanic corrosion. In another aspect, the invention relates to a hydrocarbon composition having at least about 12% renewable components comprising butanol, wherein the composition has an electrical conductivity of at least about 10 pS/m. In another aspect, the electrical conductivity is measured according to ASTM D2624 or ASTM D4308.

In one aspect, the invention relates to a hydrocarbon composition having at least about 12% renewable components comprising butanol, wherein the composition has an exhaust, evaporative or permeation emission that is substantially the same or less a hydrocarbon composition comprising no more than about 10% ethanol. In another aspect, the measured emissions component is carbon monoxide, oxides of nitrogen, carbon dioxide, total hydrocarbons, methane, benzene, 1,3-butadiene, formaldehyde, or acetaldehyde.

In one aspect, the invention relates to a method to compare the compatibility of a butanol composition with an elastomer to the compatibility of an ethanol composition with the same elastomer, comprising: (i) contacting a hydrocarbon composition comprising at least about 12% renewable components comprising butanol with a first sample of the elastomer for a time period of at least about one day while, separately, contacting a hydrocarbon composition comprising no more than about 10% ethanol with a second sample of the same elastomer for about the same time period; (ii) measuring a value of a physical or chemical property from the first and second samples of the elastomer following the contacting; and comparing the values from the first and second samples. In another aspect, the contacting is for at least about one week at a temperature of no greater than about 40° C. In another aspect, the method further comprises curing the elastomer prior to the contacting and/or cutting the elastomer into a slab prior to the contacting. In another aspect, the physical or chemical property of the elastomer is mass swell, volume swell, elongation, hardness, tensile strength, or permeability.

In one aspect, the invention relates to a method to compare the compatibility of a butanol composition with a fiberglass resin or sealant to the compatibility of an ethanol composition with the same fiberglass resin or sealant, comprising: (i) contacting a hydrocarbon composition comprising at least about 12% renewable components comprising butanol with a first sample of the fiberglass resin or sealant for a time period of at least about one day while, separately, contacting a hydrocarbon composition comprising no more than 10% ethanol with a second sample of the same fiberglass resin or sealant for about the same time period; (ii) measuring a value of a physical or chemical property from the first and second samples of the resin or sealant following the contacting; and (iii) comparing the values from the first and second samples. In another aspect, the contacting is for a time period of at least about 30 days at a temperature of no greater than about 60° C. In another aspect, the physical or chemical property of the fiberglass resin or sealant is leaching, delamination, mass swell, volume swell, hardness, or flexural strength.

In one aspect, the invention relates to a method to compare an electrical conductivity of a butanol composition to an electrical conductivity of an ethanol composition, comprising: (i) measuring the electrical conductivity of a hydrocarbon composition comprising at least about 12% renewable components comprising butanol; (ii) measuring the electrical conductivity of a hydrocarbon composition comprising no more than about 10% ethanol; (iii) comparing the electrical conductivity of (i) with (ii).

In one aspect, the invention relates to a method to compare an exhaust emission of a butanol composition to an exhaust emission of an ethanol composition, comprising: (i) operating a vehicle containing a hydrocarbon composition comprising at least about 12% renewable components comprising butanol in the fuel system of the vehicle; (ii) obtaining an exhaust sample from the vehicle during operation; (iii) measuring an exhaust emission from the sample; (iv) repeating steps (i) to (iii) while operating the vehicle containing a hydrocarbon composition comprising no more than about 10% ethanol in the fuel system of the vehicle; and (v) comparing the exhaust emission from the vehicle containing a hydrocarbon composition comprising at least about 12% renewable components comprising butanol with the exhaust emission from a vehicle containing a hydrocarbon composition comprising no more than about 10% ethanol.

In one aspect, the invention relates to a method to compare an evaporative emission of a butanol composition to an evaporative emission of an ethanol composition, comprising: (i) adding a hydrocarbon composition comprising at least about 12% renewable components comprising butanol to an evaporative emissions generator; (ii) heating the generator to form a volatile portion of the composition; (iii) collecting a sample from the headspace in the generator; (iv) measuring an evaporative emission from the sample; and (v) comparing the evaporative emission of (iii) with the same evaporative emission from a hydrocarbon composition comprising no more than about 10% ethanol. In one aspect, the evaporative emission is measured at a temperature of at least about 70° F. In another aspect, the evaporative emission is measured more than once during heating.

In one aspect, the invention relates to a method to compare a permeation emission of a butanol composition to a permeation emission of an ethanol composition, comprising: (i) operating a fuel system containing a hydrocarbon composition comprising at least about 12% renewable components comprising butanol; (ii) measuring a permeation emission of the fuel system; and (iii) comparing the permeation emission of (ii) with the same permeation emission from a hydrocarbon composition comprising no more than about 10% ethanol.

In one aspect, the invention relates to a hydrocarbon composition having at least about 12% renewable components comprising butanol identified by a method described herein as having substantially the same or improved properties when compared to a hydrocarbon composition comprising no more than about 10% ethanol. In another aspect, the butanol is isobutanol. In another aspect, the butanol is no greater than about 16% by volume in the composition. In another aspect, the butanol is about 12.5% by volume in the composition.

In another aspect the renewable composition has at least about 16% butanol, or at least about 24% butanol. In another aspect the invention has not more than 50%, 40%, or 30% butanol.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIGS. 8A-8E show a comparison of the top 20 permeate species for test fuels described in the examples.

FIG. 9 shows the ozone reactivity of test fuels described in the examples.

DETAILED DESCRIPTION OF THE INVENTION

Figure 1:
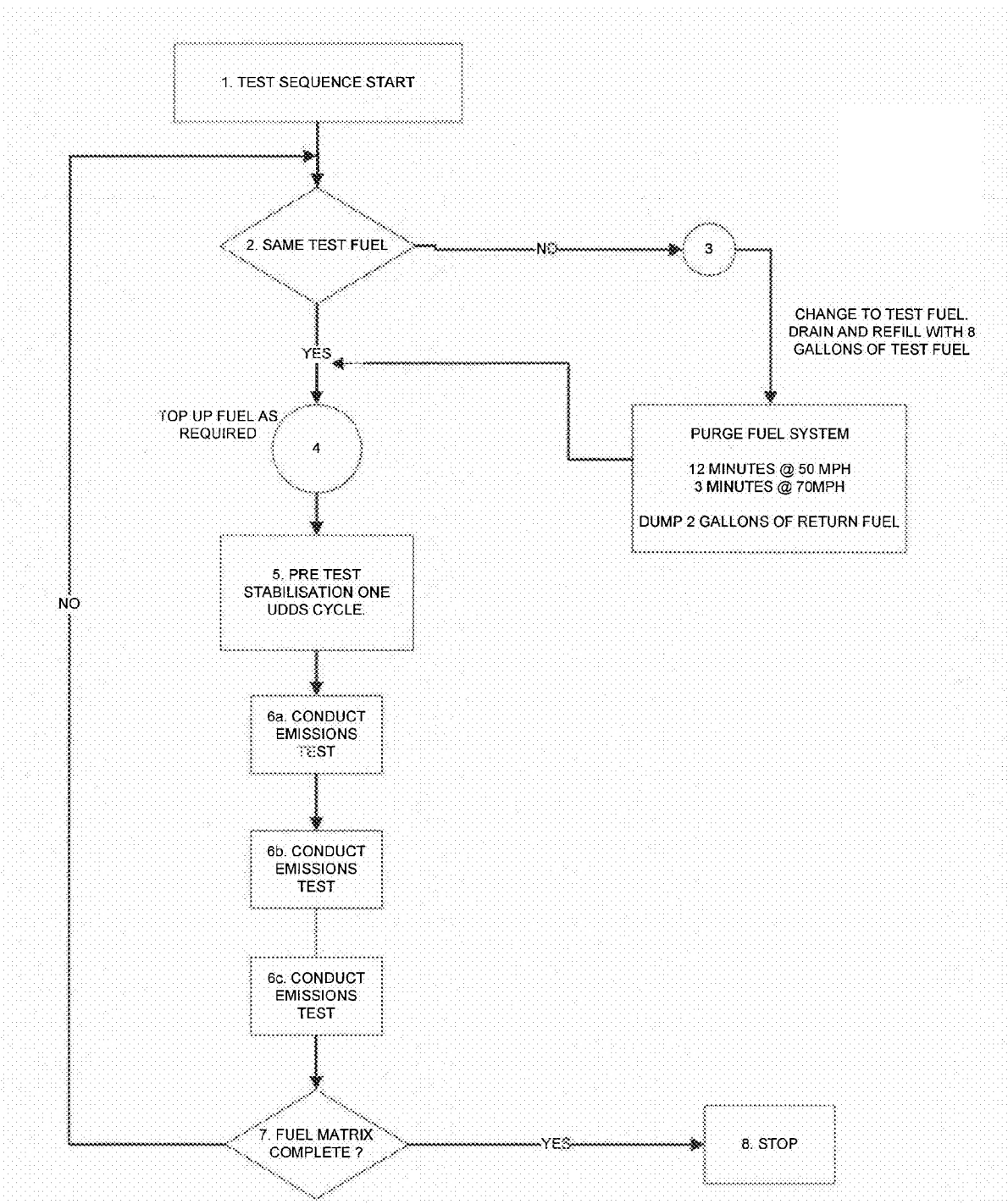
FIG. 1 shows a fuel change procedure in preparation for emission testing methods in the examples.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

The materials, methods and examples are illustrative only and are not intended to be limiting. Other features and advantages of the invention will be apparent from the detailed description and from the claims.

The following definitions and abbreviations are to be used for the interpretation of the claims and the specification.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, preferably within 5% of the reported numerical value.

The term "invention" or "present invention" as used herein is a non-limiting term and is not intended to refer to any single embodiment of the particular invention but encompasses all possible embodiments as described in the specification and the claims.

The term "butanol" as used herein, refers to 2-butanol, 1-butanol, isobutanol or mixtures thereof.

The term "substantially the same" when used in reference to the comparison of a property of a composition of the invention to another means that the properties differ by less than about 20%, with less than about 15% or 10% are more preferred. The properties can also differ by less than about 5%, 4%, 3%, 2% or 1%.

As used herein, "renewable components" when used in reference to a hydrocarbon composition of the invention includes compositions containing butanol and/or butanol and ethanol blends. Such renewable components may be produced from biomass feedstocks, typically by action of a microorganism or a recombinant microorganism. Suitable biomass feedstocks include, but are not limited to, rye, wheat, corn, cane, barley, cellulosic material, lignocellulosic material, or mixtures thereof.

Unless otherwise specified, the methods described herein are based on the standard testing methods of, for example, the American Society for Testing and Materials (ASTM), and on federal (e.g., Department of Energy or Environmental Protection Agency) and/or state standards (e.g., California or CARB).

In embodiments, the invention is directed to a hydrocarbon composition comprising renewable components comprising butanol. In some embodiments, the composition has one or more performance, physical and/or chemical properties that is substantially the same or improved when compared to a comparable composition comprising ethanol. In embodiments, the renewable components comprise at least about 12%, 12.5%, 15%, 20%, 25%, 30%, 35%, 40%, 45%, 50%, 55%, 60%, 65%, 60%, 75%, 80%, 85%, 90%, 95%, or 99% of the composition volume (including any ranges of values therein). In embodiments, the renewable components comprise at least about 16% or at least about 24% of the composition volume. In embodiments, the renewable components comprise about 12%, about 16% or about 24% of the composition volume. In embodiments, the renewable components comprise from about 12% to about 99% of the composition volume. In embodiments, the renewable components comprise from about 16% to about 50% of the composition volume. In embodiments, the renewable components comprise from about 24% to about 50% of the composition volume. In embodiments, the renewable components comprise from about 16% to about 40% of the composition volume. In embodiments, the renewable components comprise from about 24% to about 40% of the composition volume. In embodiments, the renewable components comprise from about 16% to about 24% of the composition volume. In embodiments, the renewable components consist essentially of butanol.

In embodiments, the hydrocarbon composition comprises at least about 12%, 12.5%, 15%, 20%, 25%, 30%, 35%, 40%, 45%, 50%, 55%, 60%, 65%, 60%, 75%, 80%, 85%, 90%, 95%, or 99% butanol of the composition volume (including any ranges of values therein). In embodiments, the composition comprises at least about 16% or at least about 24% butanol. In embodiments, the composition comprises from about 12% to about 99% butanol. In embodiments, the composition comprises from about 16% to about 50% butanol. In embodiments, the composition comprises from about 24% to about 50% butanol. In embodiments, the composition comprises from about 16% to about 40% butanol. In embodiments, the composition comprises from about 24% to about 40% butanol. In embodiments, the composition comprises from about 16% to about 24% butanol.

In other embodiments, the butanol comprises at least about 0.1%, 0.5%, 1%, 5%, 10%, 15%, 20%, 30%, 40%, 50%, 60%, 70%, 80%, 90%, 95% or 99% of the composition volume (including any ranges of values therein). In other embodiments, the ethanol comprises at least about 0.1%, 0.5%, 1%, 5%, 10%, 15%, 20%, 30%, 40%, 50%, 60%, 70%, 80%, 90%, 95% or 99% of the composition volume (including any ranges of values therein). In embodiments, the butanol of any composition or method of the invention described herein is isobutanol. In embodiments, the butanol of any composition or method of the invention described herein is no greater than about 12.5% by volume in the composition. In embodiments, the butanol of any composition or method of the invention described herein is no greater than about 12.5% by volume in the composition. In embodiments, the hydrocarbon composition comprises about 12%, about 16%, or about 24% butanol.

From time to time herein, embodiments comprise properties or measures resulting from hydrocarbon compositions comprising butanol that are substantially the same as or are improved as compared to those resulting from hydrocarbon compositions comprising ethanol. In some embodiments, such properties or measures from hydrocarbon compositions comprising at least about 12% by volume butanol are substantially the same as or are improved as compared to those resulting from hydrocarbon compositions comprising no more than about 10% ethanol. In some embodiments, such properties or measures from hydrocarbon compositions comprising at least about 16% or comprising about 16% by volume butanol are substantially the same as or are improved as compared to those resulting from hydrocarbon compositions comprising no more than about 10% ethanol. In some embodiments, such properties or measures from hydrocarbon compositions comprising at least about 24% or comprising about 24% by volume butanol are substantially the same as or are improved as compared to those resulting from hydrocarbon compositions comprising no more than about 15% ethanol.

Properties and Compatibility of Elastomers with Butanol Hydrocarbon Compositions In embodiments, a composition of the invention is compatible and/or is capable of being used with an elastomer. Elastomeric compounds can be found in many parts of a fuel system or terminal, such as in gaskets and seals, and are known in the art. However, any elastomeric compound used for an automotive purpose can be used in relation to the compositions and methods of the present invention.

Examples of elastomer include, but are not limited to, FKM fluoroelastomer, ethylene oxide copolymer, VQM fluorosilicone rubber, hydrogenated acrylonitrile butadiene rubber, acrylonitrile butadiene rubber, silicon rubber, chlorinated polyethylene, chloroprene rubber, styrene butadiene rubber, terpolymer of ethylene propylene diene monomer rubber, vulcanized rubber, thermoplastic rubber, chlorinated polyethylene, epichlorohydride, chlorosulfonated polyethylene synthetic rubber, fluoropolymer elastomer, styrene-acrylonitrile, unsaturated polyester resin, polyester laminate, and any combinations thereof.

The physical and chemical properties of elastomers have been described. Examples of such properties include, but are not limited to, mass swell, volume swell, elongation, hardness, tensile strength, flexural strength and/or permeability.

Methods for measuring a physical or chemical property of an elastomer have been described. Examples of such methods include, but are not limited to standard ASTM testing methods, and federal and state standards. In embodiments of the invention, one or more physical or chemical properties of an elastomer are measured.

In other embodiments, the hardness of an elastomer is measured with a durometer. In embodiments, the hardness of an elastomer is measured according to ASTM D2240. In embodiments, the tensile strength of an elastomer is measured according to ASTM D412. In other embodiments, the permeability of an elastomer is measured according to SAE J2665. In embodiments, the swell of an elastomer is measured according to ASTM D471. In embodiments, the durometer hardness of an elastomer is measured according to ASTM D2240. In other embodiments, the elongation of an elastomer is measured according to ASTM D471. In embodiments, the hardness of an elastomer is measured according to ASTM D471. In embodiments, the volume of an elastomer is measured according to ASTM D471. In embodiments, the mass of an elastomer is measured according to ASTM D471. In embodiments, the indentation hardness of an elastomer is measured according to ASTM D2583. In embodiments, the international hardness of an elastomer is measured according to ASTM D1415. In embodiments, an elastomer of the invention includes a material with the ability to resist oil-induced swelling and/or the ability to resist heat as defined by ASTM D2000. In embodiments, the flexural strength of an elastomer is measured according to ASTM D790.

In other embodiments, the change in durometer hardness of an elastomer upon contact with the composition is substantially the same or less than the change in durometer hardness of the elastomer upon contact with a hydrocarbon composition comprising no more than about 10% ethanol. In embodiments, the elastomer has a durometer hardness of from about 20 to about 90 units after contact with the composition. In embodiments, the elastomer has a change in durometer hardness of less than about 6% after contact with the composition.

In embodiments, the invention is directed to a hydrocarbon composition comprising at least about 12% renewable components comprising butanol, wherein the composition is capable of being used with an elastomer, wherein the change in tensile strength of the elastomer upon contact with the composition is substantially the same or less than the change in tensile strength of the elastomer upon contact with a hydrocarbon composition comprising no more than about 10% ethanol. In other embodiments, the invention is directed to a hydrocarbon composition comprising at least about 12% renewable components comprising butanol, wherein the composition is capable of being used with an elastomer, wherein the elastomer has a change in tensile strength or elongation of less than about 70% after contact with the composition.

In embodiments, the invention is directed to a hydrocarbon composition comprising at least about 12% renewable components comprising butanol, wherein the composition is capable of being used with an elastomer, wherein the change in hardness of the elastomer upon contact with the composition is substantially the same or less than the change in hardness of the elastomer upon contact with a hydrocarbon composition comprising no more than about 10% ethanol. In other embodiments, the invention is directed to a hydrocarbon composition comprising at least about 12% renewable components comprising butanol, wherein the composition is capable of being used with an elastomer, wherein the elastomer has a change in hardness of less than about 20% after contact with the composition.

In embodiments, the invention is directed to a hydrocarbon composition comprising at least about 12% renewable components comprising butanol, wherein the composition is capable of being used with an elastomer, wherein the change in volume of the elastomer upon contact with the composition is substantially the same or less than the change in volume of the elastomer upon contact with a hydrocarbon composition comprising no more than about 10% ethanol.

In other embodiments, the invention is directed to a hydrocarbon composition comprising at least about 12% renewable components comprising butanol, wherein the composition is capable of being used with an elastomer, wherein the elastomer has a change in volume of less than about 160% after contact with the composition. In other embodiments, the invention is directed to a hydrocarbon composition comprising at least about 12% renewable components comprising butanol, wherein the composition is capable of being used with an elastomer, wherein the change in indentation hardness of the elastomer upon contact with the composition is substantially the same or less than the change in indentation hardness of the elastomer upon contact with a hydrocarbon composition comprising no more than about 10% ethanol. In other embodiments, the invention is directed to a hydrocarbon composition comprising at least about 12% renewable components comprising butanol, wherein the composition is capable of being used with an elastomer, wherein the elastomer has an indentation hardness of from about 30 to about 65 units of Barcol hardness after contact with the composition.

In embodiments, the invention is directed to a hydrocarbon composition comprising at least about 12% renewable components comprising butanol, wherein the composition is capable of being used with an elastomer, wherein the change in mass of the elastomer upon contact with the composition is substantially the same or less than the change in mass of the elastomer upon contact with a hydrocarbon composition comprising no more than about 10% ethanol.

In other embodiments, a hydrocarbon composition comprising at least about 12% renewable components comprising butanol, wherein the composition is capable of being used with an elastomer, wherein the change in international hardness of the elastomer upon contact with the composition is substantially the same or less than the change in international hardness of the elastomer upon contact with a hydrocarbon composition comprising no more than about 10% ethanol. In other embodiments, the invention is directed to a hydrocarbon composition comprising at least about 12% renewable components comprising butanol, wherein the composition is capable of being used with an elastomer, wherein the elastomer has an international hardness of from about 10 to about 100 International Rubber Hardness Determination (IRHD) units after contact with the composition.

In other embodiments, the invention is directed to a method to compare the compatibility of a butanol composition with an elastomer to the compatibility of an ethanol composition with the same elastomer, comprising: (i) contacting a hydrocarbon composition comprising at least about 12% renewable components comprising butanol with a first sample of the elastomer for a time period of at least about one day while, separately, contacting a hydrocarbon composition comprising no more than about 10% ethanol with a second sample of the same elastomer for about the same time period; (ii) measuring a value of a physical or chemical property from the first and second samples of the elastomer following the contacting; and (iii) comparing the values from the first and second samples. In embodiments, the contacting is for at least about 1, 2, 3, 4, 5, 6, 7, 8, 9, 10, 11 or 12 weeks; 5, 6, 7, 8, 9, 10, 11 or 12 months; or 1, 2, 3, 4, or 5 years (or any ranges of values therein). In embodiments, the temperature is no greater than about 10, 20, 30, 40, 50, 60, 70 or 80° C. (or any ranges of values therein). In embodiments, the elastomer can be selected from any of those described herein, including FKM fluoroelastomer, ethylene oxide copolymer, FVQM fluorosilicone rubber, hydrogenated acrylonitrile butadiene rubber, acrylonitrile butadiene rubber, silicon rubber, chlorinated polyethylene, chloroprene rubber, styrene butadiene rubber, terpolymer of ethylene propylene diene Monomer rubber, vulcanized rubber, or a thermoplastic elastomer. In embodiments, the method further comprises curing the elastomer prior to the contacting. In embodiments, the method further comprises cutting the elastomer into a slab prior to the contacting.

In embodiments, the physical or chemical property of the elastomer can be any such property described herein, including mass swell, volume swell, elongation, hardness, tensile strength, or permeability. In embodiments, the physical or chemical property is measured by any method described herein, including measuring the hardness with a durometer. In embodiments, the hardness is measured according to ASTM D2240. In embodiments, the tensile strength is measured according to ASTM D412. In embodiments, the permeability is measured according to SAE J2665. In embodiments, the mass swell or volume swell is measured according to ASTM D471.

Properties and Compatibility of Fiberglass Resins and Sealants with Butanol Hydrocarbon Compositions In embodiments, a composition of the invention is compatible and/or is capable of being used with a fiberglass resin or sealant. Fiberglass resins or sealants can be found in many parts of a fuel system or terminal, and are known in the art. However, any fiberglass resin or sealant used for an automotive purpose can be used in relation to the compositions and methods of the present invention.

Examples of fiberglass resins or sealants include, but are not limited to, high density polyethylene (HDP), fluorinated HDP, polypropylene, acetal homopolymer, acetal copolymer, polyethylene terephthalate polyester, polyethylene terephthalate glycol copolyester, polybutylene terephthalate polyester, cork, nylon, polyvinylidene fluoride, polytetrafluoroethylene, polyphenylene sulfide, isophthalic polyester resin, terephthalic polyester resin, epoxy novolac vinyl ester resin, epoxy resin, polythiourea, nitrile and any combinations thereof. In embodiments, the fiberglass resin or sealant is a material for an underground storage tank (UST) in the retail section of a fuel supply chain.

The physical and chemical properties of physical and chemical properties of fiberglass resins or sealants have been described. Examples of such properties include, but are not limited to, mass swell, volume swell, elongation, hardness, tensile strength, flexural strength and/or permeability.

Methods for measuring a physical or chemical property of a fiberglass resin or sealant have been described. Examples of such methods include, but are not limited to standard ASTM testing methods, and federal and state standards. In embodiments of the invention, one or more physical or chemical properties of a fiberglass resin or sealant are measured.

In other embodiments, the hardness of a fiberglass resin or sealant is measured with a durometer. In embodiments, the hardness of a fiberglass resin or sealant is measured according to ASTM D2240. In embodiments, the tensile strength of a fiberglass resin or sealant is measured according to ASTM D412. In other embodiments, the permeability of a fiberglass resin or sealant is measured according to SAE J2665. In embodiments, the swell of a fiberglass resin or sealant is measured according to ASTM D471. In embodiments, the durometer hardness of a fiberglass resin or sealant is measured according to ASTM D2240. In other embodiments, the elongation of a fiberglass resin or sealant is measured according to ASTM D471. In embodiments, the hardness of a fiberglass resin or sealant is measured according to ASTM D471. In embodiments, the volume of a fiberglass resin or sealant is measured according to ASTM D471. In embodiments, the mass of a fiberglass resin or sealant is measured according to ASTM D471. In embodiments, the indentation hardness of a fiberglass resin or sealant is measured according to ASTM D2583. In embodiments, the international hardness of a fiberglass resin or sealant is measured according to ASTM D1415. In embodiments, the flexural strength of a fiberglass resin or sealant is measured according to ASTM D790.

In other embodiments, the invention is directed to a hydrocarbon composition comprising at least about 12% renewable components comprising butanol, wherein the composition is capable of being used with a fiberglass tank resin or sealant, wherein the change in durometer hardness of the resin or sealant upon contact with the composition is substantially the same or less than the change in durometer hardness of the resin or sealant upon contact with a hydrocarbon composition comprising no more than about 10% ethanol. In other embodiments, the invention is directed to a hydrocarbon composition comprising at least about 12% renewable components comprising butanol, wherein the composition is capable of being used with a fiberglass tank resin or sealant, wherein the resin or sealant has a change in durometer hardness of from about 20 to about 90 units after contact with the composition. In other embodiments, the invention is directed to a hydrocarbon composition comprising at least about 12% renewable components comprising butanol, wherein the composition is capable of being used with a fiberglass tank resin or sealant, wherein the resin or sealant has a change in durometer hardness of less than about 6% after contact with the composition.

In embodiments, the invention is directed to a hydrocarbon composition comprising at least about 12% renewable components comprising butanol, wherein the composition is capable of being used with a fiberglass tank resin or sealant, wherein the change in indentation hardness of the resin or sealant upon contact with the composition is substantially the same or less than the change in indentation hardness of the resin or sealant upon contact with a hydrocarbon composition comprising no more than about 10% ethanol. In other embodiments, the invention is directed to a hydrocarbon composition comprising at least about 12% renewable components comprising butanol, wherein the composition is capable of being used with a fiberglass tank resin or sealant, wherein the resin or sealant has an indentation hardness of from about 30 to about 65 units of Barcol hardness after contact with the composition. In other embodiments, the invention is directed to a hydrocarbon composition comprising at least about 12% renewable components comprising butanol, wherein the composition is capable of being used with a fiberglass tank resin or sealant, wherein the change in flexural strength of the resin or sealant upon contact with the composition is substantially the same or less than the change in flexural strength of the resin or sealant upon contact with a hydrocarbon composition comprising no more than about 10% ethanol.

In embodiments, the present invention is directed to a hydrocarbon composition comprising at least about 12% renewable components comprising butanol, wherein the composition is capable of being used with a fiberglass tank resin or sealant, wherein the resin or sealant has a flexural strength of from about $10 \times 10^3$ to about $30 \times 10^3$ psi after contact with the composition. In other embodiments, the invention is directed to a hydrocarbon composition comprising at least about 12% renewable components comprising butanol, wherein the composition is capable of being used with a fiberglass tank resin or sealant, wherein the resin or sealant has substantially no visual signs of leaching or delamination after contact with the composition. In other embodiments, the invention is directed to a hydrocarbon composition comprising at least about 12% renewable components comprising butanol, wherein the composition is capable of being used with a fiberglass tank resin or sealant, wherein the change in volume of the resin or sealant upon contact with the composition is substantially the same or less than the change in volume of the resin or sealant upon contact with a hydrocarbon composition comprising no more than about 10% ethanol.

In other embodiments, the invention is directed to a hydrocarbon composition comprising at least about 12% renewable components comprising butanol, wherein the composition is capable of being used with a fiberglass tank resin or sealant, wherein the resin or sealant has a change in volume of less than about 160% after contact with the composition. In embodiments, the invention is directed to a hydrocarbon composition comprising at least about 12% renewable components comprising butanol, wherein the composition is capable of being used with a fiberglass tank resin or sealant, wherein the change in mass of the resin or sealant upon contact with the composition is substantially the same or less than the change in mass of the resin or sealant upon contact with a hydrocarbon composition comprising no more than about 10% ethanol.

In other embodiments, the invention is directed to a method to compare the compatibility of a butanol composition with a fiberglass resin or sealant to the compatibility of an ethanol composition with the same fiberglass resin or sealant, comprising: (i) contacting a hydrocarbon composition comprising at least about 12% renewable components comprising butanol with a first sample of the fiberglass resin or sealant for a time period of at least about one day while, separately, contacting a hydrocarbon composition comprising no more than 10% ethanol with a second sample of the same fiberglass resin or sealant for about the same time period; (ii) measuring a value of a physical or chemical property from the first and second samples of the resin or sealant following the contacting; and (iii) comparing the values from the first and second samples. In embodiments, the contacting is for a time period described herein, including at least about 30 days. In embodiments, the contacting at a temperature described herein, including a temperature of no greater than about 60° C.

In embodiments, the physical or chemical property of the fiberglass resin or sealant can be any property described herein, including leaching, delamination, mass swell, volume swell, hardness, or flexural strength. In embodiments, the property can be measured by any method described herein, including measuring the leaching or delamination visually. In embodiments, the leaching or delamination is measured with metallographic or microscopic examination. In embodiments, the hardness is measured with a durometer. In embodiments, the hardness is measured according to ASTM D2240. In embodiments, the hardness is measured according to the Barcol hardness test.

In embodiments, the hardness is measured according to ASTM D2583. In embodiments, the flexural strength is measured according to ASTM D790. In embodiments, the fiberglass resin or sealant can be any fiberglass resin or sealant described herein, including high density polyethylene (HDP), fluorinated HDP, polypropylene, acetal homopolymer, acetal copolymer, polyethylene terephthalate polyester, polyethylene terephthalate glycol copolyester, polybutylene terephthalate polyester, cork, nylon, polyvinylidene fluoride, polytetrafluoroethylene, polyphenylene sulfide, isophthalic polyester resin, terephthalic polyester resin, epoxy novolac vinyl ester resin, epoxy resin, polythiourea, or nitrile.

Electrical Conductivity of Butanol Hydrocarbon Compositions

In embodiments, a composition of the invention has an electrical conductivity. Methods for measuring an electrical conductivity have been described. Examples of such methods include, but are not limited to standard ASTM testing methods, and federal and state standards. In embodiments, the electrical conductivity is measured according to ASTM D2624 or ASTM D4308.

In embodiments, the invention is directed to a hydrocarbon composition comprising renewable components and butanol having an electrical conductivity. In embodiments, the electrical conductivity of the composition is substantially the same or less than the electrical conductivity of a hydrocarbon composition comprising ethanol. In embodiments, the hydrocarbon composition comprising ethanol comprises no more than about 10% ethanol. In other embodiments, the invention is directed to a hydrocarbon composition comprising at least about 12% renewable components comprising butanol, wherein the electrical conductivity of the composition is substantially the same or less than the electrical conductivity of a hydrocarbon composition comprising no more than about 10% ethanol.

In embodiments, the invention is directed to a hydrocarbon composition comprising a renewable component and butanol, wherein the composition has an electrical conductivity that does not cause static build-up, static discharge, or galvanic corrosion. In embodiments, the invention is directed to a hydrocarbon composition comprising at least about 12% renewable components comprising butanol, wherein the composition has an electrical conductivity that does not cause static build-up, static discharge, or galvanic corrosion.

In embodiments, the invention is directed to a hydrocarbon composition comprising a renewable component and butanol, wherein the composition has an electrical conductivity of at least about 10, 15, 20, 25, 30, 35, 40, 45, 50, 75, 100, 200, 300, 400, 500, or 1000 pS/m (as well as ranges between any of these values). In embodiments, the invention is directed to a hydrocarbon composition comprising at least about 12% renewable components comprising butanol, wherein the composition has an electrical conductivity of at least about 10, 15, 20, 25, 30, 35, 40, 45, 50, 75, 100, 200, 300, 400, 500, or 1000 pS/m (as well as ranges between any of these values).

In embodiments, the invention is directed to a method to compare an electrical conductivity of a butanol composition to an electrical conductivity of an ethanol composition, comprising: (i) measuring the electrical conductivity of a hydrocarbon composition comprising at least about 12% renewable components comprising butanol; (ii) measuring the electrical conductivity of a hydrocarbon composition comprising no more than about 10% ethanol; (iii) comparing the electrical conductivity of (i) with (ii). In embodiments, the electrical conductivity is measured according to ASTM D2624 or ASTM D4308.

Exhaust, Evaporative and Permeation Emissions of Butanol Hydrocarbon Compositions In embodiments, a composition of the invention results in exhaust, evaporative and/or permeation emissions. Methods for measuring exhaust, evaporative and/or permeation emissions have been described. Examples of such methods include, but are not limited to standard ASTM testing methods, and federal and state standards. Predictive models can also used by refiners to demonstrate whether or not a particular batch of fuel meets the emissions requirements set by the state. An example of such a model is the California Air Regulatory Board (CARB) predictive model. In this model, the properties of a given batch of fuel are the inputs and the calculated changes in oxides of nitrogen (NOx), total hydrocarbons (THC), and potency weighted toxics (POT) emissions from vehicles consuming the gasoline the outputs, expressed as percentage changes versus a reference composition (defined in the regulations). A given batch of fuel must have a negative value for each of these outputs in order to be compliant with California regulations.

In embodiments, the invention is directed to a hydrocarbon composition comprising renewable components and butanol having an exhaust, evaporative and/or permeation emission. In embodiments, the exhaust, evaporative and/or permeation emission of the composition is substantially the same or less than the exhaust, evaporative and/or permeation emission of a hydrocarbon composition comprising ethanol. In embodiments, the hydrocarbon composition comprising ethanol comprises no more than about 10% ethanol. In other embodiments, the invention is directed to a hydrocarbon composition comprising at least about 12% renewable components comprising butanol, wherein the exhaust, evaporative or permeation emission of the composition is substantially the same or less than the exhaust, evaporative or permeation emission of a hydrocarbon composition comprising no more than about 10% ethanol.

Examples of exhaust, evaporative and permeation emissions have been described and any such example can be used in relation to the present invention. In embodiments, the measured emissions component is one or more of a carbon monoxide, oxides of nitrogen, carbon dioxide, total hydrocarbons, methane, benzene, 1,3-butadiene, formaldehyde, and acetaldehyde. In embodiments, the total hydrocarbons comprise a polycyclic aromatic hydrocarbon. In embodiments, the polycyclic aromatic hydrocarbon is one or more of an acenaphthene, acenaphthylene, anthracene, benzo[a]anthracene, benzo[b]fluoranthene, benzo[k]fluoranthene, benzo[g,h,i]perylene, benzo[a]pyrene, benzo[e]pyrene, chrysene, dibenzo[a,h]anthracene, fluoranthene, fluorene, indeno[1,2,3-cd]pyrene, 2-methylnaphthalene, naphthalene, phenanthrene, perylene, and pyrene. In embodiments, the total hydrocarbons comprise one or more of an ethane, ethylene, acetylene, propane, propylene, trans-2-butene, butane, 1-butene, 2-methylpropenc, 2,2-dimethypropane, propyne, 1,3-butadiene, 2-methylpropane, 1-butyne, or cis-2-butene.

In embodiments, the invention is directed to a method to compare an exhaust emission of a butanol composition to an exhaust emission of an ethanol composition, comprising: (i) operating a vehicle containing a hydrocarbon composition comprising at least about 12% renewable components comprising butanol in the fuel system of the vehicle; (ii) obtaining an exhaust sample from the vehicle during operation; (iii) measuring an exhaust emission from the sample; (iv) repeating steps (i) to (iii) while operating the vehicle containing a hydrocarbon composition comprising no more than about 10% ethanol in the fuel system of the vehicle; and (v) comparing the exhaust emission from the vehicle containing a hydrocarbon composition comprising at least about 12% renewable components comprising butanol with the exhaust emission from a vehicle containing a hydrocarbon composition comprising no more than about 10% ethanol.

In embodiments, the exhaust emission is carbon monoxide, oxides of nitrogen, carbon dioxide, total hydrocarbons, methane, benzene, 1,3-butadiene, formaldehyde or acetaldehyde. In embodiments, the total hydrocarbon comprises a polycyclic aromatic hydrocarbon. In embodiments, the polycyclic aromatic hydrocarbon is acenaphthene, acenaphthylene, anthracene, benzo [a]anthracene, benzo[b]fluoranthene, benzo[k]fluoranthene, benzo[g,h,i]perylene, benzo[a]pyrene, benzo[e]pyrene, chrysene, dibenzo[a,h]anthracene, fluoranthene, fluorene, indeno[1,2,3-cd]pyrene, 2-methylnaphthalene, naphthalene, phenanthrene, perylene, or pyrene. In embodiments, the total hydrocarbon comprises ethane, ethylene, acetylene, propane, propylene, trans-2-butene, butane, 1-butene, 2-methylpropene, 2,2-dimethypropane, propyne, 1,3-butadiene, 2-methylpropane, 1-butyne, or cis-2-butene. In embodiments, the sample is collected in a bag or cartridge. In embodiments, the measuring is performed with gas chromatography, high performance liquid chromatography, gas chromatography-mass spectrometry, or Fourier transform infrared spectroscopy. In embodiments, the modal raw emission of the sample is measured at 1 Hz for carbon monoxide, oxide of nitrogen, carbon dioxide, and total hydrocarbons. In embodiments, the total hydrocarbon is measured using a flame ionization detector. In embodiments, the carbon monoxide is measured using a non-dispersive infrared detector. In embodiments, the carbon dioxide is measured using a chemiluminescent detector. In embodiments, the methane is measured according to SAE J1151.

In embodiments, the invention is directed to a method to compare an evaporative emission of a butanol composition to an evaporative emission of an ethanol composition, comprising: (i) adding a hydrocarbon composition comprising at least about 12% renewable components comprising butanol to an evaporative emissions generator; (ii) heating the generator to form a volatile portion of the composition; (iii) collecting a sample from the headspace in the generator; (iv) measuring an evaporative emission from the sample; and (v) comparing the evaporative emission of (iii) with the same evaporative emission from a hydrocarbon composition comprising no more than about 10% ethanol. In embodiments, the evaporative emission is measured at a temperature of at least about 70° F. In embodiments, the evaporative emission is measured more than once during the heating. In embodiments, the evaporative emission is hydrocarbon, carbon monoxide, oxide of nitrogen, carbon dioxide, ozone, ozone precursor, total hydrocarbon, methane, benzene, or toluene.

In embodiments, the invention is directed to a method to compare a permeation emission of a butanol composition to a permeation emission of an ethanol composition, comprising: (i) operating a fuel system containing a hydrocarbon composition comprising at least about 12% renewable components comprising butanol; (ii) measuring a permeation emission of the fuel system; and (iii) comparing the permeation emission of (ii) with the same permeation emission from a hydrocarbon composition comprising no more than about 10% ethanol. In embodiments, the permeation emission is carbon monoxide, oxides of nitrogen, carbon dioxide, total hydrocarbons, methane, benzene, 1,3-butadiene, formaldehyde or acetaldehyde.

In embodiments, the invention is directed to a hydrocarbon composition comprising renewable components and butanol identified by any one of methods described herein. In embodiments, the identified composition has substantially the same or improved properties when compared to a hydrocarbon composition comprising ethanol. In embodiments, the invention is directed to a hydrocarbon composition comprising at least about 12% renewable components comprising butanol identified by any method described herein as having substantially the same or improved properties when compared to a hydrocarbon composition comprising no more than about 10% ethanol.

In embodiments, the invention is directed to a method to compare a permeation emission of a butanol composition to a permeation emission of an ethanol composition, comprising: (i) operating a fuel system containing a hydrocarbon composition comprising at least about 12% renewable components comprising butanol; (ii) measuring a permeation emission of the fuel system; and (iii) comparing the permeation emission of (ii) with the same permeation emission from a hydrocarbon composition comprising no more than about 10% ethanol. In embodiments, the permeation emission is total hydrocarbons, methane, benzene, or 1,3-butadiene.

EXAMPLES

The present invention is further defined in the following examples. It should be understood that these examples, while indicating embodiments of the invention, are given by way of illustration only and are not intended to be comprehensive or limiting. From the above discussion and these examples, one skilled in the art can ascertain the essential characteristics of this invention, and without departing from the spirit and scope thereof, can make various changes and modifications of the invention to adapt it to various uses and conditions.

Abbreviations used in the Examples are as follows. "vol %", "v/v %" or "v %" is a measurement of concentration expressed in percentage of a liquid solute in a liquid solution, and calculated as the volume of the solute, divided by the total volume of solution, multiplied by 100%. "° F." means degree(s) Fahrenheit. "° C." means degree(s) Celsius. "psi" means pound-force per square inch. "EtOH" means ethanol. "BuOH" means butanol. "E10" means ethanol at 10 vol %. "Bu16" means butanol at 16 vol %.

Example 1

Compatibility of Elastomers with Butanol-Containing Fuels

Methods:

The purpose of this experiment is to assess the properties and compatibility of an elastomer with fuel blends containing isobutanol. Hardness testing of elastomers is conducted according to ASTM D2240 (Standard test method for rubber property—durometer hardness), before and after exposure to the test fuels. As stated in ASTM D2240, this test method is based on the penetration of a specific type of indentor when forced into the material under specified conditions. The indentation hardness is inversely related to the penetration, and is dependent on the elastic modulus and viscoelastic behavior of the material. ASTM D471 (Standard test method for rubber property—effect of liquids) is employed as a basis for measuring changes in other rubber properties after immersion in test liquids. Properties such as mass, volume and breaking resistance, among others, can be determined within this test procedure.

Tensile properties of elastomers are measured according to ASTM D412 (Standard test method for vulcanized rubber and thermoplastic elastomers—tension), which covers procedures for determination of tensile strength and elongation. Elastomer permeability to fuel is measured as described in SAE J2665, which is a Surface Vehicle Recommended Practice, entitled "Test procedure to measure the fuel permeability of materials by the cup weight loss method."

For comparative purposes, some tests do not include all of the ASTM reference oils, and the temperature and/or duration of exposure of a fuel to an elastomer is slightly varied.

Experiments are conducted on elastomer materials which fall into two subsets. The first subset are elastomers that are typically used in fuel system applications. These materials, listed below, are exposed to test fuels for 1 week at a temperature of 40° C. prior to testing:

FKM: fluoro rubber of the polymethylene type that utilizes vinylidene fluoride as a comonomer and has substituent fluoro, alkyl, perfluoroalkyl or perfluoroalkoxy groups on the polymer chain, with or without a cure site monomer (having a reactive pendant group), e.g. Viton®;

ECO: Ethylene oxide (oxirane) and chloromethyl oxirane (epichlorohydrin copolymer);

FVQM: silicone rubber having fluorine, vinyl, and methyl groups on the polymer chain;

HNBR: hydrogenated acrylonitrile butadiene; and

NBR: acrylonitrile-butadiene.

The second subset are elastomers that can come into incidental contact with fuels.

These materials, listed below, are typically expected to exhibit good resistance to alcohols but poor resistance to hydrocarbons, and are exposed to test fuels for 1 week at a temperature of 23° C. prior to testing:

VMQ: silicone rubber having both methyl and vinyl substituent groups on the polymer chain;

CPE: chlorinated polyethylene;

CR: chloroprene, e.g., Neoprene;

SBR: styrene-butadiene; and

EPDM: terpolymer of ethylene, propylene, and a diene with the residual unsaturated portion of the diene in the side chain.

These materials are available from the following manufacturers: DuPont (Wilmington, Del.), 3M (St. Paul, Minn.), Veyance (Goodyear)(Akron, Ohio), Parker O-Ring (Lexington, Ky.), Parker/Dayco (Manitowoc, Wis.), McMaster-Carr (Los Angeles, Calif.), and Rubber Sheet Roll (Shippensburg, Pa.).

The elastomer materials are cured and cut into slabs prior to testing. Standard elastomer compounds are also prepared for testing to have 75±5 durometer hardness rating, which is typical of rubber seals such as O-rings.

The following test fuels are used in the experiments:

TABLE 1

Test Fuels for Elastomer Testing

| | | |
|---|---|---|
| CARB Fuel 1 | 10 V % Carson [E10] | Current quality RFG3 |
| CARB Fuel 2 | 16 V % Cherry Point [Bu16] | High Aromatic Low Olefin base |
| CARB Fuel 3 | 16 V % Carson [Bu16] | Low Aromatic High Olefin base |
| CARB Fuel 4 | 50:50 mix Carson E10 + Carson Bu16 | E10/Bu16 Transmix |

Hydrocarbon base stocks for this program are sourced from two different refineries: BP Carson ("Carson") and BP Cherry Point ("Cherry Point") which currently supply the California market. These two refineries have different process configurations and, as a result, their respective hydrocarbon base stocks represent the range of aromatics/olefins levels typically found in CARB (California Air Resources Board) gasolines. Each test fuel is blended to meet current CaRFG3 specifications and pass the 31 Dec. 2009 version of the predictive model. Fuels are approved by ARB staff prior to testing.

Results:

Elastomer samples contacted with test fuels containing 16 vol % isobutanol (Bu16) or a 50:50 mix of 10 vol % ethanol (E10):16 vol % isobutanol (Bu16) have a resulting durometer hardness of from about 20 to about 90 units and/or a resulting change in durometer hardness of less than about 6%. Elastomer samples contacted with test fuels containing 16 vol % isobutanol or a 50:50 mix of 10 vol ethanol:16 vol % isobutanol have a change in tensile strength or elongation of less than about 70%. Elastomer samples contacted with test fuels containing 16 vol % isobutanol or a 50:50 mix of 10 vol % ethanol:16 vol % isobutanol have a change in hardness of less than about 20%. Elastomer samples contacted with test fuels containing 16 vol % isobutanol or a 50:50 mix of 10 vol % ethanol:16 vol % isobutanol have a change in volume of less than about 160%. Elastomer samples contacted with test fuels containing 16 vol % isobutanol or a 50:50 mix of 10 vol % ethanol:16 vol % isobutanol have an indentation hardness of from about 30 to about 65 units of Barcol hardness. Elastomer samples contacted with test fuels containing 16 vol % isobutanol or a 50:50 mix of 10 vol % ethanol:16 vol % isobutanol have an international hardness of from about 10 to about 100 International Rubber Hardness Determination (IRHD) units.

Elastomer samples contacted with test fuels containing 16 vol % isobutanol or a 50:50 mix of 10 vol % ethanol:16 vol % isobutanol have substantially the same or reduced volume swell, mass swell, elongation, hardness, tensile strength and/or permeability when compared to elastomer samples contacted with the test fuel containing 10 vol % ethanol.

Test fuels containing 16 vol % isobutanol or a 50:50 mix of 10 vol % ethanol:16 vol % isobutanol are compatible with the tested elastomer samples and/or have substantially the same or greater compatibility with the tested elastomer compared to the test fuel containing 10 vol % ethanol.

Example 2

Compatibility of Fiberglass Resins or Sealants with Butanol-Containing Fuels

Methods:

The purpose of this experiment is to assess the properties and compatibility of a fiberglass resin or sealant with fuel blends containing isobutanol. Testing is performed using the fuel blends described in Example 1. Measurements of material properties is based on standard test methods (with preference given to ASTM methods), unless otherwise specified. Subjective assessments, such as microscopic examination by independent materials experts at SwRI, can be performed in addition to the standard test methods.

Fiberglass resins and sealants are exposed to the test fuels for 30 days at a temperature of 60° C. The following measurements are performed on fiberglass and resin sealant materials, before and after fuel blend exposure:

Metallographic/microscopic examination for visual signs of leaching or delamination;

Mass/volume/swell measurements;

Hardness tests, by durometer hardness (ASTM D2240), by Barcol impressor (ASTM D2583), or by another method, whichever is deemed most suitable by SwRI; and Measurements of flexural strength, flexural modulus and flexural strain, by ASTM D790.

Composites fabricated from the following fiberglass resins or sealants are evaluated:

High density polyethylene (HDPE): KS-1866A;

Fluorinated HDPE: KS-1866A (surface of plastic was fluorinated in secondary process);

Polypropylene (PP): KS-537;

Acetal homopolymer (polyoxymethylene-POM): Delrin II 150;

Acetal copolymer: Acetron GP;

Polyethylene terephthalate polyester (PETP): Ertalyte;

Polyethylene terephthalate glycol copolyester (PETG): Spectar;

Polybutylene terephthalate polyester (PBT): Hydex 4101;

Cork (blended w/ nitrile rubber);

Nylon 6/6, 6, 11, & 12;

Polyvinylidene fluoride (PVDF): KS-5341;

Polytetrafluoroethylene (PTFE): KS-2342A;

Polyphenylene sulfide (PPS): Techtron CM;

Isophthalic polyester resin: Vipel F764 and Vipel F701;

Terephthalic polyester resin: Vipel F774;

Epoxy novolac vinyl ester resin: Vipel F085;

Epoxy resin: Epon 862/Epi-Cure 3282 (RT cured and heat cured);

Polythiourea (free film & coated on steel): PTU; and

Buna-N.

These materials are be available from the following manufacturers: K-mac Plastics (Wyoming, Mich.), Mc-Master Carr (Princeton, N.J.), DuPont (Wilmington, Del.), Arkema (Philadelphia, Pa.), Quadrant (Zurich, Switzerland), Eastman (Kingsport, Tenn.), Ensinger-Hyde (Grenloch, N.J.), Boedeker, (Leander, Tex.), Dow (Midland, Mich.), Huntsman (The Woodlands, Tex.), Air Products (Lehigh Valley, Pa.), AOC Resins (Collierville, Tenn.), and Global Specialty Products (Mt. Holly, N.J.).

Results:

Fiberglass resin or sealant samples contacted with test fuels containing 16 vol % isobutanol (Bu16) or a 50:50 mix of 10 vol % ethanol (E10):16 vol % isobutanol (Bu16) have a resulting durometer hardness of from about 20 to about 90 units and/or a resulting change in durometer hardness of less than about 6%. Fiberglass resin or sealant samples contacted with test fuels containing 16 vol % isobutanol or a 50:50 mix of 10 vol % ethanol:16 vol % isobutanol have a resulting indentation hardness of from about 30 to about 65 units. Fiberglass resin or sealant samples contacted with test fuels containing 16 vol % isobutanol or a 50:50 mix of 10 vol % ethanol:16 vol % isobutanol have a resulting flexural strength of from about $10 \times 10^3$ to about $30 \times 10^3$ psi. Fiberglass resin or sealant samples contacted with test fuels containing 16 vol % isobutanol or a 50:50 mix of 10 vol % ethanol:16 vol % isobutanol have substantially no visual signs of leaching or delamination. Fiberglass resin or sealant samples contacted with test fuels containing 16 vol % isobutanol or a 50:50 mix of 10 vol % ethanol:16 vol % isobutanol have a change in volume of less than about 160%.

Test fuels containing 16 vol % isobutanol or a 50:50 mix of 10 vol % ethanol:16 vol % isobutanol are compatible with the tested fiberglass resin and sealant samples and/or have substantially the same or greater compatibility with the tested fiberglass resin and sealant compared to the test fuel containing 10 vol % ethanol.

Example 3

Electrical Conductivity of Butanol-Containing Fuels

Methods:

The purpose of this experiment is to assess the electrical conductivity of fuel blends containing isobutanol. The electrical conductivity of pure ethanol and pure isobutanol has been reported. (International Critical Tables of Numerical Data, Physical Chemistry and Technology, $1^{st}$ Electronic Edition, Edited by Washburn, E.W. Originally published from 1926-1930, and released by Knovel in 2003.) Pure ethanol has a conductivity of 135 pS/m, and pure isobutanol has a conductivity of 950 pS/m. However, the conductivity of hydrocarbon compositions comprising 10 vol % ethanol (E10) and 16 vol % isobutanol (Bu16) has not been described.

The ability of a fuel to generate and dissipate charge during fuel-handling operations depends on the fuel's electrical conductivity. The time for a static charge to dissipate is inversely related to conductivity, so a high conductivity is desirable for safety reasons. Conversely, a fuel with high conductivity could in principle facilitate galvanic corrosion (i.e., corrosion of metals having different electrochemical potentials when they are immersed in an electrolyte).

Testing is performed using the same fuel blends described in Example 1. Measurements of material properties is based on standard test methods (with preference given to ASTM methods), unless otherwise specified. For example, testing is performed following ASTM D2624 ("Standard test method for the electrical conductivity of aviation and distillate fuels") or ASTM D4308 ("Standard test method for the electrical conductivity of liquid hydrocarbons by precision meter"). Both methods cover measurement of the "rest conductivity," which is the electrical conductivity when a fuel is uncharged. In other words, rest conductivity is electrical conductivity in the absence of ionic depletion or polarization, and can therefore be measured at the initial instant of current measurement when a direct-current voltage is applied to the fuel, or by measurement of the average current when an alternating-current voltage is applied to the fuel, or continuously by use of a flow-cell. The methods of ASTM D2624 and ASTM D4308 have good precision over a range of electrical conductivities up to 2000 pS/m. ASTM D4308 also offers extension of the measurement range up to 20,000 pS/m, but with lower precision, so these methods used together are suitable for measurements on the test fuels.

Results:

The electrical conductivity of test fuels containing 16 vol % isobutanol or a 50:50 mix of 10 vol % ethanol:16 vol % isobutanol does not cause static build-up static discharge, or galvanic corrosion. The electrical conductivity of test fuels containing 16 vol % isobutanol or a 50:50 mix of 10 vol % ethanol:16 vol % isobutanol is less than about 2000 pS/m. The electrical conductivity of test fuels containing 16 vol % isobutanol or a 50:50 mix of 10 vol % ethanol:16 vol % isobutanol is close to the usual range of conductivities measured for existing CARB gasolines. The electrical conductivity of test fuels containing 16 vol % isobutanol or a 50:50 mix of 10 vol % ethanol:16 vol % isobutanol is substantially the same or greater than the electrical conductivity of the test fuel containing 10 vol % ethanol.

Example 4

CARB Predictive Model Emissions of Butanol-Containing Fuels

The purpose of this experiment was to assess performance parameters and emissions impact of a butanol-containing fuel using the CARB predictive model described above. For this analysis, the fuel properties and emissions noted in the following Table were identified for a typical fuel blend compositions containing 10 vol % ethanol (E10) meeting CARB requirements (i.e., all model outputs being negative values), and used to estimate the same fuel properties and emissions for a 15 vol % ethanol blend (E15) and a 12 vol % butanol blend (B12) produced using approximately the same hydrocarbon gasoline.

TABLE 2

Properties and Emissions Impact of E10, E15 and B12 Fuels

| | Units | E10 | E15 | B12 |
| --- | --- | --- | --- | --- |
| Fuel Properties | | | | |
| Reid vapor pressure (RVP) | psig | 7.00 | 7.00 | 7.00 |
| Aromatics | vol % | 22.0 | 20.8 | 21.5 |
| Benzene | vol % | 0.70 | 0.66 | 0.68 |
| Olefins | vol % | 7.0 | 6.6 | 6.8 |
| Sulfur | ppm-wt | 9.0 | 8.5 | 8.8 |
| T50 | deg F. | 215 | 215 | 215 |
| T90 | deg F. | 317 | 317 | 317 |
| Oxygen | wt % | 3.50 | 5.25 | 2.63 |
| Emissions Impact | | | | |
| NOx (oxides of nitrogen) | gm/mile | −0.20% | 10.46% | −3.61% |
| Total Hydrocarbons (THC) | gm/mile | −1.65% | −3.70% | −1.18% |
| Potency Weighted Toxics (POT) | gm/mile | −1.75% | −4.07% | −2.26% |

Compared to E10, E15 had a 50% greater greenhouse gas (GHG) emissions benefit, offered significant improvements in THC and POT, but had dramatically increased NOx emissions. However, compared to E10, B12 offered some of the same GHG benefits as E15 without increased NOx emissions.

Example 5

CARB Predictive Model Emissions of Butanol-Containing Fuels

The purpose of this experiment is to assess performance parameters and emissions impact of 16 vol % butanol-containing fuel using the CARB predictive model described above. For this analysis, the fuel properties and emissions noted in the Table 2 are identified for a typical fuel blend compositions containing 10 vol % ethanol (E10) meeting CARB requirements (i.e., all model outputs being negative values), and is used to estimate the same fuel properties and emissions for a 16 vol % butanol blend (B16) produced using approximately the same hydrocarbon gasoline.

B16 has comparable NOx, POT and THC benefits to E10 and twice the GHG benefits as E10.

Example 6

Exhaust Emissions of Butanol-Containing Fuels

Methods:

The purpose of this experiment is to assess the exhaust emissions of fuel blends containing isobutanol, including the impact on ozone reactivity and potency-weighted toxics emissions.

Testing is performed using the same fuel blends described in Example 1. Measurements of material properties is based on standard test methods (with preference given to ASTM methods), unless otherwise specified.

The vehicle fleet used in the experiments is selected to include representative vehicles from the Tech III, Tech IV and Tech V vehicle technology groups as defined in the Predictive model. To represent the California vehicle pool, the test vehicles are selected from Tech Groups 3, 4 and 5. Specifically, a total of seven vehicles (three from Tech III, two from Tech IV and two from Tech V) are used as indicated in Table 3.

TABLE 3

Vehicle Fleet for Exhaust Emissions Testing

| Vehicle No | Vehicle Description | Year | Program |
|---|---|---|---|
| 1 | Buick Riviera 5.0L | 1981 | Emissions & Evaporative |
| 2 | Honda Accord 5.0L | 1991 | Emissions |
| 3 | Ford Crown Victoria 5.2L | 1985 | Emissions |
| 4 | Lexus ES 300 3.0L | 1992 | Emissions & Evaporative |
| 5 | Nissan Sentra 1.6L | 1985 | Emissions |
| 6 | Chevrolet Silverado 4.8L | 2007 | Emissions & Evaporative |
| 7 | Dodge Caravan 3.3L | 2005 | Emissions |

Vehicles are approved by CARB prior to testing and checked for general service requirements including acceptable tires, after treatment device, exhaust leaks, transmission fluid level, and proper vehicle operation on the chassis dynamometer. The exhaust systems of all vehicles is modified to allow the measurement of pre- and post-catalyst exhaust emissions. Each vehicle has the following start of test services: drain the engine oil, perform a single oil flush, replace the oil filter, charge the crankcase with the manufacturers specified engine oil, replace the fuel filter, and replace the air cleaner element.

All vehicles undergo any manufacturer scheduled maintenance based on the current odometer reading. If unscheduled maintenance is necessary, the repairs are made to Original Equipment Manufacturer (OEM) specifications using OEM or OEM approved parts when possible. Following these services, each vehicle accumulates a minimum of 100 miles of on-road stabilization.

In preparation for emissions testing, the vehicle fuel system is drained and refueled with the CaRFG3+E10 (CARB Fuel 1) according to the prescribed fuel change procedure in FIG. 1. This fuel change procedure is based on the Auto-Oil protocol. Specifically, the vehicle's exhaust system is prepared for connection to the Constant Volume Sampler (CVS) with the chassis dynamometer coefficients taken from the Environmental Protection Agency's (EPA's) Test Car List Database. All necessary calibrations of the testing equipment are performed and the vehicle is run over one Urban Dynamometer Driving Schedule (UDDS) sequence to prepare it for testing the following day. The vehicle is soaked overnight (12 to 36 hours). The exhaust emissions and fuel economy (FE) is determined by operating the vehicles on a chassis dynamometer over the Federal Test Procedure (FTP-75) 4 bag test. Measurement of regulated emissions includes total hydrocarbons (THC), carbon monoxide (CO), oxides of nitrogen ($NO_x$) and carbon dioxide ($CO_2$) determined in a manner consistent to 40 CFR parts 86 and 600. Samples for hydrocarbon speciation, including aldehydes, ketones, alcohols, ethers, methane and NMHC, are collected with Tedlar bags and/or 2,4-dinitrophenylhydrazine (DNPH) cartridges or suitable alternative [Non-Methane Organic Gas (NMOG); Gas Chromatography-Mass Spectrometry (GCMS), Fourier transform infrared spectroscopy (FTIR), etc.). Post test analysis is performed by gas chromatography (GC) and high performance liquid chromatography (HPLC). Measurement of modal raw emissions is also recorded at 1 Hz for THC, CO, NO and $CO_2$.

Each vehicle is prepared with one UDDS sequence and the steps of soaking and exhaust emissions and fuel economy measuring are repeated. After three tests are completed on a given vehicle/fuel combination, its repeatability is checked to determine if a fourth test is required. Repeatability criteria for gaseous emissions are as follows: ratio between highest and lowest; CO, 1.330; HC, 1.175; $NO_x$, 1.500; $CO_2$, 2.000.

Following the repeating, the vehicle is drained and refueled with the CaRFG3+16% isobutanol (CARB Fuel 2) according to the above fuel change procedure. The vehicle is then prepared with one UDDS sequence and the steps of soaking and exhaust emissions and fuel economy measuring are repeated. After three tests are completed on a given vehicle/fuel combination, its repeatability is checked to determine if a fourth test is required. Repeatability criteria for gaseous emissions are as follows: ratio between highest and lowest; CO, 1.330; HC, 1.175; $NO_x$, 1.500; $CO_2$, 2.000.

Following the repeating, the vehicle is drained and refueled with the CaRFG3+16% isobutanol (CARB Fuel 3) according to the above fuel change procedure. The vehicle is then prepared with one UDDS sequence and the steps of soaking and exhaust emissions and fuel economy measuring are repeated. After three tests are completed on a given vehicle/fuel combination, its repeatability is checked to determine if a fourth test is required. Repeatability criteria for gaseous emissions are as follows: ratio between highest and lowest; CO, 1.330; HC, 1.175; $NO_x$, 1.500; $CO_2$, 2.000.

Following the repeating, the vehicle is drained and refueled with the CaRFG3 transmix (CARB Fuel 4) according to the above fuel change procedure. The vehicle is then prepared with one UDDS sequence and the steps of soaking and exhaust emissions and fuel economy measuring are repeated. After three tests are completed on a given vehicle/fuel combination, its repeatability is checked to determine if a fourth test is required. Repeatability criteria for gaseous emissions are as follows: ratio between highest and lowest; CO, 1.330; HC, 1.175; $NO_x$, 1.500; $CO_2$, 2.000.

Following the repeating of this process in all test vehicles, the exhaust emissions samples are analyzed, including the influence of these findings on the California predictive model.

Results:

The exhaust emissions of test fuels containing 16 vol % isobutanol or a 50:50 mix of 10 vol % ethanol:16 vol % isobutanol are in compliance with CARB requirements. Test fuels containing 16 vol % isobutanol or a 50:50 mix of 10 vol % ethanol:16 vol % isobutanol are the same as or have increased benefits on greenhouse gas emissions compared to test fuels containing 10 vol % ethanol.

Example 7

Evaporative Emissions of Butanol-Containing Fuels

Methods:

The purpose of this experiment is to assess the evaporative emissions of fuel blends containing isobutanol.

Testing is performed using the same fuel blends described in Example 1 and the vehicles of Table 3. Measurements of material properties is based on standard test methods (with preference given to ASTM methods), unless otherwise specified. Test vehicles are evaluated following the California Evaporative Emission Test Sequences consisting of: the California Three Day Diurnal Test, and the California Two Day Supplemental Diurnal Test.

California Three Day Diurnal Test

The test sequence for the California Three Day Diurnal Test is as follows:
1. Fuel Change
2. Urban Drive (LA-4)
3. Fuel Change
4. Canister Loading to 1.5× working capacity
5. 12 to 36 hour park (68° F. to 86° F.)
6. FTP drive at 75° F. (unmeasured)
7. Running Loss Measurement at 105° F. in a RL-SHED
8. One hour Hot Soak at 105° F. in the traditional SHED
9. Three Day Diurnal (65° F. to 105° F. to 65° F.) in a VT-SHED California Two Day Supplemental Diurnal Test The test sequence for the California Two Day Supplemental Diurnal Test is as follows:
1. Fuel Change
2. Urban Drive (LA-4)
3. Fuel Change
4. Canister Loading to 2 gram measured breakthrough
5. 12 to 36 hour park (68° F. to 86° F.)
6. FTP drive at 75° F. (unmeasured)
7. One hour Hot Soak at 75° F. in the traditional SHED
8. Two Day Diurnal (65° F. to 105° F. to 65° F.) in a VT-SHED Execution of Evaporative Emissions Tests Emission tests are CARB enhanced evaporative emission tests as contained in "California Evaporative Emission Standards and Test Procedures for 2001 and Subsequent Model Motor Vehicles." Each vehicle receives an incoming inspection to include documentation of vehicle ID (VIN, Test Group, Evap Family, etc.), fuel system pressure check, thorough check of fluid levels (including oil and filter change), emission test instrumentation and road safety inspection. Test instrumentation includes installation of a fuel tank surface thermocouple and means of draining the fuel from the fuel tank. The thermocouple provides a close approximation of the liquid fuel temperature, which is used for matching the FTTP (fuel tank temperature profile) during the running loss test. Fuel temperature is also monitored during the diurnal emission test.

An incoming emission test is performed to ensure that no fuel system leaks or evaporative emission control system problems exist. If unscheduled maintenance is necessary, the repairs are made to Original Equipment Manufacturer (OEM) specifications using OEM or OEM approved parts when possible. Unscheduled maintenance is defined as any repairs or changes required to the vehicle to return it to a state of normal operation outside of those normally deemed necessary by the manufacturer. All methods are performed in accordance with 40 C.F.R. 86.1834-01.

A FTP, Hot Soak, 24-hour diurnal constitutes an adequate test of vehicle condition. Prior to beginning the emission testing, each vehicle is preconditioned/stabilized to the test fuel. Following previously established protocols, a 4-week preconditioning program are be employed. Each vehicle is operated twice per week over the on-road LA-4 course, and two LA-4 cycles (one cold, one hot) are driven.

Upon completing the preconditioning, each vehicle is tested for evaporative emissions according to the ARB 3-day test sequence and the supplemental 2-day test described above. Each test is performed with "fresh" test fuel. The enhanced evaporative emissions test procedure includes the LA-4 preconditioning, fuel tank drain and 40% fill, canister load, FTP drive cycle, running loss test, hot soak, and the 72-hour diurnal. Supplemental tests include the LA-4 preconditioning, fuel tank drain and 40% fill, canister load, FTP drive cycle, hot soak, and 48-hour diurnal. Speciation of evaporative emissions is performed.

Upon completion of the emission tests and acceptance of the test data from CARE Fuel 1, the fuel system of each vehicle is drained and flushed to remove residual fuel. CARE Fuel 2 is then introduced and the 4-week on-road preconditioning process begins. This same procedure is followed for CARE Fuels 3 and 4.

Data Analysis and Reporting

Following analysis of the data generated, a final report is prepared. The report includes a summary of all tests conducted and their results, statistical evaluation of those results, calculation of any impacts on ozone reactivity for Bu16 relative to E10 and an assessment of the measured emissions compared to those predicted by the California Predictive Model.

Results:

The evaporative emissions of test fuels containing 16 vol % isobutanol or a 50:50 mix of 10 vol % ethanol:16 vol % isobutanol are in compliance with CARB requirements. Test fuels containing 16 vol % isobutanol or a 50:50 mix of 10 vol % ethanol:16 vol % isobutanol are the same as or have increased benefits on greenhouse gas emissions compared to test fuels containing 10 vol % ethanol.

Example 8

Performance and Toxic Air Pollutants of Butanol-Containing Fuels

Methods:

The purpose of this experiment is to assess the toxic air pollutants of fuel blends containing isobutanol. Testing is performed using the 10 vol % ethanol fuel (CARB Fuel 1) and one of the 16 vol % butanol fuels (CARB Fuel 3) described in Example 1. Per EPA methodology, the testing is done with a single, recent vintage, high production model vehicle. Table 4 identifies the vehicle chosen for this program:

TABLE 4

Test Vehicle for EPA 211(b) Testing

| Vehicle Description | Year | Program |
|---|---|---|
| Toyota Camry 2.4L | 2009 | Unregulated |

Additionally, the test vehicle is selected from a group as per the EPA requirements for fuel/fuel additive registration, and is obtained with less than 500 miles on the odometer. When the vehicle is received, it is checked for an intact after treatment device, exhaust leaks, acceptable tires, proper oil level, proper transmission fluid level, and proper vehicle operation on the mileage accumulation dynamometer (MAD). The vehicle fuel system are drained and refueled with the CaRFG3+E10 (CARB Fuel 1) fuel. No other fuel is used until testing and mileage accumulations are completed with the fuel. Mileage accumulation for 4,000 miles is performed using a MAD or suitable alternative. All scheduled maintenance is performed according to the manufacturer's recommendations. If unscheduled maintenance is necessary, the repairs are made by Original Equipment Manufacturer (OEM) specifications using OEM or OEM approved parts. To ensure that the post-maintenance emission levels are within 20 percent of the pre-maintenance emission levels, baseline emissions are measured before resuming mileage accumulation after any unscheduled maintenance.

For emission testing after the first 4,000 miles, the vehicle's exhaust system is prepared for connection to the Constant Volume Sampler (CVS), the chassis dynamometer coefficients is taken from EPA's Test Car List Database. All necessary calibrations of the testing equipment are performed and the vehicle is run over one UDDS sequence to prepare it for testing the following day. The vehicle is soaked overnight (12 to 36 hours) and a 4-bag Federal Test Procedure (FTP75) is performed. Measurement of regulated emissions include total hydrocarbons (THC), carbon monoxide (CO), oxides of nitrogen ($NO_x$), carbon dioxide ($CO_2$) and methane (NMHC) and are determined in a manner consistent to 40 C.F.R. parts 86 and 600. Samples for hydrocarbon speciation include aldehydes, ketones, alcohols, ethers, PAH and NPAH. Sample collections are with Tedlar bags and/or DNPH cartridges or suitable online alternative (NMOG, GCMS, FTIR, etc.). Post test analysis is performed with GC and HPLC. Measurement of modal raw emissions are recorded at 1 Hz for THC, CO, NO and $CO_2$. The soaking and sample measurement steps are then repeated two additional times on different days.

The catalytic converter is then removed and replaced with an uncoated, non-functioning catalyst monolith of similar size or a blank spool piece and the soaking and sample measurement steps are repeated as described above. A fuel change procedure is then performed as described above using the CaRFG3+16% isobutanol (CARB Fuel 3). The fuel filters are then changed and the fuel supply is purged. No other fuel is used until testing with the fuel is completed. The oil is then changed and the monolith or spool piece is replaced with the original catalytic converter and mileage accumulation for 4,000 miles is performed using the same criteria above. The soaking and sample measurement steps above are then repeated two additional times on different days. All collected samples are collected and analyzed and final report is prepared.

The analysis of the regulated and speciated emissions is conducted in the following manner. Exhaust constituents are analyzed as follows:

| Constituent | Analysis Method |
|---|---|
| Total Hydrocarbon* | Flame Ionization Detector |
| Carbon Monoxide* | Non-Dispersive Infrared Detector |
| Carbon Dioxide* | Non-Dispersive Infrared Detector |
| Oxides of Nitrogen* | Chemiluminescent Detector |
| Methane | Gas Chromatograph |

*modal emissions measurements are performed for these constituents

For the determination of the unregulated emissions, following test methods are used. Table 5 provides the equipment used for the speciation of volatile-phase hydrocarbon compounds, aldehydes, ketones, alcohols, and ethers and semi-volatile emissions for both volatile- and particulate-phase PAH.

TABLE 5

Sampling Methodologies

| Regulated THC, NMHC, CO, $NO_x$, and Particulate | Speciation $C_1$-$C_{12}$ | PAH Particulate | PAH Volatile | Alcohols and Ethers | Aldehydes and Ketones |
|---|---|---|---|---|---|
| Cont., Bag, 90 mm Filter | Bag | 20 × 20 Filter | PUF | Bubbler | Cartridge |

Volatile hydrocarbon compounds are determined by hydrocarbon speciation. Hydrocarbon speciation ($C_1$ to $C_{12}$ hydrocarbons, aldehydes and ketones) is conducted on exhaust emissions samples to detect the presence of more than 200 different exhaust species. Four gas chromatography (GC) procedures and one High Performance Liquid Chromatography (HPLC) procedure are used to identify and quantify specific compounds. One GC is used for the measurement of methane, a second for C2-C4 species, and a third for C5-C12 species including three ethers (methyl tertiary butyl ether—MTBE, ethyl tertiary butyl ether—ETBE, and di-isopropyl ether—DIPE). A fourth GC is used to measure 1-methylcyclopentene, benzene, toluene, 2,3-dimethylhexane, cyclohexane, and 2,3,3-trimethylpentane, which co-elute. Analysis of all emission "sample" bags begins within 30 minutes of sampling and before the "background" bags, so that reactive exhaust compounds can be analyzed as quickly as possible. Data is reported as background corrected. A brief description of these procedures follows.

Methane Speciation

Methane levels are determined for proportional exhaust gas samples collected in Tedlar® bags. A GC equipped with a flame ionization detector (FID) is utilized for the analyses, and used in accordance with SAE J1151 procedures. The GC system is equipped with a packed column to resolve methane from other hydrocarbons in the sample. Samples are introduced into a 5-mL sample loop via a diaphragm pump. For analysis, the valve is switched to the inject position, and the helium carrier gas sweeps the sample from the loop toward the detector through a 61 cm×0.3 cm Porapak N column in series with a 122 cm×0.3 cm molecular sieve 13× column. As soon as the methane peak passes into the molecular sieve column, the helium flow is reversed through the Porapak N column to vent. For quantification, sample peak areas are compared to those of external calibration standards. Detection limits for the procedure are on the order of 0.05 mg/bhp-hr in dilute exhaust.

$C_2$-$C_4$ Species

With the aid of a DB-WAX pre-column and a 10-port switching valve, this procedure allows the separation and determination of exhaust concentrations of $C_2$-$C_4$ individual hydrocarbon species, including: ethane; ethylene; acetylene; propane; propylene; trans-2-butene; butane; 1-butene; 2-methylpropene (isobutylene); 2,2-dimethypropane (neopentane); propyne; 1,3-butadiene; 2-methylpropane; 1-butyne; and cis-2-butene. Bag samples are analyzed with a GC system which utilizes a Hewlett-Packard Model 5890 Series II GC with an FID, two pneumatically operated and electrically controlled valves, and two analytical columns. The first column separates the $C_2$-$C_4$ hydrocarbons from the higher molecular weight hydrocarbons and the polar compounds. These higher molecular weight hydrocarbons (and water and alcohols) are retained on the pre-column while the $C_2$-$C_4$ hydrocarbons are passed through to the analytical column. At the same time, the $C_2$-$C_4$ hydrocarbons are separated on the analytical column, the pre-column is back-flushed with helium to prepare for the next analysis. The carrier gas for this analysis is helium. Analysis for the $C_2$-$C_4$ hydrocarbons is typically begun within 30 minutes after sample collection is complete. Detection limits for the procedure are on the order of 0.05 mg/bhp-hr in dilute exhaust for all compounds, with a quantification limit of 0.1 mg/bhp-hr.

$C_5$-$C_{12}$ Species

Bag samples are analyzed using a gas chromatograph equipped with an FID. The GC system utilizes a Hewlett-Packard Model 5890 Series II GC with an FID, a pneumatically operated and electrically controlled valve, and a DB-1 fused silica open tubular (FSOT) column. The carrier gas is helium. Gaseous samples are pumped from the bag through the sample loop and then introduced into a liquid nitrogen cooled column. The column oven is programmed to provide a maximum temperature of 200° C. Detection limits for the procedure are in the order of 0.05 mg/bhp-hr in dilute exhaust for all compounds, and a quantification limit of 0.1 mg/bhp-hr. This procedure provides separation and exhaust concentrations for more than 100 $C_5$-$C_{12}$ individual hydrocarbon compounds.

Benzene and Toluene

This analytical procedure uses a separate system configured similarly to the third GC method (with a DB-5 analytical column in place of a DB-1 FSOT column) to resolve individual concentrations of benzene and toluene according to the CRC Auto/Oil Phase II Protocols. Separation of benzene and toluene from co-eluting peaks is carried out by fine-tuning the column head pressure to give benzene a retention time of 22 to 23 minutes. The GC is calibrated daily using a CRC 7-component calibration mixture. Detection limits for the procedure are 0.05 mg/bhp-hr in dilute exhaust for all compounds, with a quantification limit of 0.1 mg/bhp-hr.

Aldehydes and Ketones

An HPLC procedure is used for the analysis of aldehydes and ketones. The method is similar to CARB SOP MLD 104. Samples are collected in DNPH cartridges at a nominal flow rate of 2 L/min and eluted with acetonitrile. Samples are extracted from the cartridges using pure acetonitrile, transferred into volumetric flasks with ground glass joints, and either analyzed immediately or stored in ground glass stopped vials at 0° C. for no more than one week prior to analysis. For analysis, a portion of the acetonitrile solution is injected into a liquid chromatograph equipped with an ultraviolet (UV) detector. External standards of the aldehyde and ketone DNPH derivatives are used to quantify the results. The aldehydes and ketones shall include formaldehyde, acetaldehyde, acrolein, acetone, propionaldehyde, crotonaldehyde, isobutyraldehyde/methylethylketone (not resolved from each other during normal operating conditions, and so split equally between the two compounds), benzaldehyde, valeraldehyde, o-tolualdehyde, m-tolualdehyde/p-tolualdehyde (not resolved from each other during normal operating conditions, and so reported together), hexanaldehyde, and 2,5-dimethylbenzaldehyde. Detection limits for this procedure are in the order of 0.05 mg/bhp-hr aldehyde or ketone in dilute exhaust, with a quantification limit of 0.1 mg/bhp-hr.

Alcohols and Ethers

The measurement of alcohols in exhaust is accomplished by bubbling the exhaust through glass impingers containing deionized water. Water soluble alcohols are detected using two glass impingers in series to collect exhaust samples for the analysis. The two glass impingers contain 25 ml of deionized water each and are able to collect 99+ percent of the lower molecular weight alcohols which are soluble in water. Table 6 lists a number of alcohols and ethers that range in solubility from miscible to slightly soluble in water.

TABLE 6

Selected C1 to C6 Alcohols and Ethers Having Some Solubility in Water

| Compound | Empirical Formula | Compound | Empirical Formula |
|---|---|---|---|
| Water Soluble Alcohols | | | |
| Methanol | $CH_4O$ | 3-Methyl-2-butanol | $C_5H_{12}O$ |
| Ethanol | $C_2H_6O$ | Neopentanol (2,2-dimethyl-1-propanol) | $C_5H_{12}O$ |
| 2-Propyn-1-ol | $C_3H_4O$ | 1-Pentanol | $C_5H_{12}O$ |
| Allyl alcohol (2-propen-1-ol) | $C_3H_6O$ | 2-Pentanol | $C_5H_{12}O$ |
| Isopropanol | $C_3H_8O$ | 3-Pentanol | $C_5H_{12}O$ |
| n-Propanol | $C_3H_8O$ | tert-Pentanol (2-methyl-2-butanol) | $C_5H_{12}O$ |
| Crotyl alcohol (2-buten-1-ol) | $C_4H_8O$ | Phenol | $C_6H_6O$ |
| n-Butanol | $C_4H_{10}O$ | 3-Methyl-1-pentyn-3-ol | $C_6H_{10}O$ |
| Isobutanol (2-methyl-1-propanol) | $C_4H_{10}O$ | Cyclohexanol | $C_6H_{12}O$ |
| sec-Butanol (2-butanol) | $C_4H_{10}O$ | 4-Hydroxy-4-methyl-2-pentanone | $C_6H_{12}O_2$ |
| tert-Butanol (2-methyl-2-propanol) | $C_4H_{10}O$ | 2,2-Dimethyl-1,3-dioxolane-4-methanol | $C_6H_{12}O_3$ |
| Furfuryl alcohol | $C_5H_6O_2$ | 2,5-Tetrahydrofurandimethanol | $C_6H_{12}O_3$ |
| 2-Methyl-3-butyn-2-ol | $C_5H_8O$ | 1-Hexanol | $C_6H_{14}O$ |
| Cyclopentanol | $C_5H_{10}O$ | 2-Methyl-1-pentanol | $C_6H_{14}O$ |
| Tetrahydrofurfuryl alcohol | $C_5H_{10}O_2$ | 3-Methyl-3-pentanol | $C_6H_{14}O$ |
| Isopentanol (3-methyl-1-butanol) | $C_5H_{12}O$ | 4-Methyl-2-pentanol | $C_6H_{14}O$ |
| 2-Methyl-1-butanol | $C_5H_{12}O$ | 3,3-Dimethyl-2-butanol | $C_6H_{14}O$ |
| 3-Methyl-1-butanol | $C_5H_{12}O$ | 2-Ethyl-1-butanol | $C_6H_{14}O$ |
| Water Soluble Ethers | | | |
| Methyl ether | $C_2H_6O$ | Ethyl ether | $C_4H_{10}O$ |
| Methyl ethyl ether | $C_3H_8O$ | Methyl propyl ether | $C_4H_{10}O$ |
| Vinyl ether | $C_4H_6O$ | Isopropyl ether | $C_6H_{14}O$ |
| Cyclopropyl methyl ether | $C_4H_8O$ | Propyl ether | $C_6H_{14}O$ |

The temperature of the collection impingers is maintained at 0 to 5° C. with an ice water bath, and the flow rate through the impingers was maintained at 4 L/min by the sample pump. A dry gas meter is used to determine the total flow through the impingers. The temperature of the gas stream is monitored by a thermocouple immediately prior to the dry gas meter. A drier is included in the system to prevent condensation in the pump, flow meter, or dry gas meter, etc. The flow meter in the system allows for continuous monitoring of the sample to ensure proper flow rates during the sampling. The Teflon line connecting the CVS and the solenoid valve is heated to approximately 235° F. to prevent water from condensing in the sample line.

The exhaust sample is collected continuously during each cold- and hot-start test cycle. Upon completion of each transient cycle, the impingers are removed, and the contents transferred to a 30 mL polypropylene bottle and capped. Analysis of samples begins within four hours of sampling. The analytical method is similar to CARB SOP MLD 101. For analysis, a 1.0 µL portion of the aqueous solution is injected into a GC equipped with a FID and an autosampler. The analytical column is a 30 m×0.53 mm i.d. capillary column of 1 µm DB-Wax film thickness. The carrier gas is helium and set to give optimum separation (18 ml/min.). To quantify the results, the sample peak areas are compared to peak areas of standard solutions. External standards containing methanol, ethanol; isopropanol, n-propanol, isobutanol, and n-butanol in deionized water are used to quantify the results. Sample chromatograms also search for the presence of a number of other alcohols using predetermined retention times. The search list includes: tert-butanol (CAS#75-65-0), 2-methyl-2-butanol (CAS#75-85-4), 2-butanol (CAS#78-92-2), 3-pentanol (CAS#584-02-1), 3-methyl-3-pentanol (CAS#77-74-7), 3,3-dimethyl-2-butanol (CAS#464-07-3), 2-pentanol (CAS#6032-29-7), 4-methyl-2-pentanol (CAS#108-11-2), 2-methyl-1-butanol (CAS#137-32-6), 3-methyl-1-butanol (CAS#123-51-3), 1-pentanol (CAS#71-41-0), 2-methyl-1-pentanol (CAS#105-30-6), and 2-ethyl-1-butanol (CAS#97-95-0). Detection limits with this procedure are in the order of 0.05 mg/bhp-hr in dilute exhaust, with a quantification limit of 0.1 mg/bhp-hr.

Polycyclic Aromatic Hydrocarbons (PAH)

In addition to the regulated and $C_1$ to $C_{12}$ hydrocarbon exhaust emissions, semi-volatile (volatile- and particulate-phase) PAH compounds are also be determined for each fuel. The analytical method is similar to CARB SOP MLD 429 using an isotope dilution technique. The 19 PAH target compound list includes: acenaphthene, acenaphthylene, anthracene, benzo[a]anthracene, benzo[b]fluoranthene, benzo[k]fluoranthene, benzo[g,h,i]perylene, benzo[a]pyrene, benzo[e]pyrene, chrysene, dibenzo[a,h]anthracene, fluoranthene, fluorene, indeno[1,2,3-cd]pyrene, 2-methylnaphthalene, naphthalene, phenanthrene, perylene, and pyrene. A 400 $in^2$ fluorocarbon-coated glass fiber filter (20× 20-inch Pallflex filter) is used to collect the particulate-phase PAH, and a PUF/XAD/PUF sandwich adsorbent trap for the volatile-phase PAH. The PUF/XAD/PUF traps contain a layered sampling media consisting of a 1.25 inch deep layer of polyurethane foam (PUF), a 0.5 inch deep layer of XAD-2 resin, and a second 1.25 inch deep layer of PUF. The XAD-2 resin is incorporated to improve the trapping efficiency for the lighter PAH compounds.

Volatile-phase PAH samples present a particular problem for light-duty sampling because conventional sampling techniques do not allow for sufficient sample to be gathered to meet EPA detection requirements. Commercially available sampling media and hardware are of insufficient size to allow for the collection of sample volumes needed to meet these detection limits. Sampling media size is also limited by the ability to extract and concentrate the samples obtained. Therefore, the following approach is devised to involve both custom built sampling hardware and a modified sampling plan. The PUF/XAD/PUF traps are sized to allow a media diameter of 4 inches, rather than the conventional 2.5 inches. This larger diameter allows a much higher flow rate to be used, while maintaining the face velocity within recommended levels for the smaller, conventional sampling media. This volume of dilute exhaust sample is sufficient for the analysis to meet a detection threshold of 1 ng/hp-hr.

Prior to sampling, both the XAD-2 and PUF sample media are cleaned. First, the XAD-2 is cleaned by siphoning four times with water using a Soxhlet. The residual water is then removed under vacuum. The XAD-2 Soxhlet is extracted three times: once with methanol for 24 hours, once with toluene for 48 hours, and finally with methylene chloride again for 48 hours. The residual methylene chloride is removed by purging with heated nitrogen. For PUF cleaning, each foam disk is Soxhlet extracted three times: once for 24 hours with acetone, once for 48 hours with hexane/ether, and finally for 24 hours with acetone.

Volatile- and particulate-phase PAH samples are obtained using a separate secondary dilution tunnel; this is operated in parallel with the smaller secondary dilution tunnel to obtain the 90-mm filter samples for particulate mass determinations. The PAH tunnel is considerably larger than the 90-mm system in order to allow for the use of 20×20-inch Pallflex sampling media to collect particulate-phase PAH compounds and to allow the use of a specially designed PUF/XAD/PUF trap to collect the volatile-phase PAH compounds. Filter and PUF/XAD/PUF trap samples are generated during each cold-start and a hot-start test. Background PAH sample sets are obtained by operating the sampling systems for about two hours with sampling media loaded, but without operating the vehicle.

Following testing, sample sets are delivered to the analytical laboratory for extraction and analysis. In cases where immediate extraction is not possible, samples are stored at 4° C. Just prior to extraction of the PUF/XAD/PUF samples, the material is placed in a Soxhlet, and 25 µL of a PAH internal standard (IS) spiking solution containing 18 deuterated PAHs is spiked onto each PUF/XAD/PUF sample. This spiked solution is used as an internal standard to verify sample recovery during the extraction process. The samples are then extracted for 16 hours with methylene chloride. After extraction, the methylene chloride extract are reduced to approximately 20 mL with a rotary evaporator and water bath held at 35° C. The concentrated extract is split into two equal portions: one for storage as a reserve and the other for analysis. Samples for analysis are solvent exchanged to hexane and cleaned with acid or base wash and silica gel fractionation; and the solvent volume reduced to 1000 µL. Each extract is then spiked with 25 µL of a recovery standard (RS) which is a mixture of 1-methylmaphthalene-d10 and p-terphenyl-d14 just prior to analysis by GC/MS. After analysis for the lower molecular weight PAH, the 1000 µL extract is carefully blown down to 100 µL. This reduced sample is then analyzed for benzo(a) anthracene and higher molecular weight PAHs.

The filter extract is treated similarly to the trap extract. One half of each filter is extracted separately, and the unextracted filter half saved as a reserve. Just prior to extraction, 20 µL of the PAH IS is spiked onto each filter after placement in the Soxhlet. Filter samples are extracted for 16 hours with toluene. After extraction, the methylene chloride extract is reduced to approximately 20 mL with a rotary evaporator and water bath held at 95° C. Samples are then solvent exchanged to hexane and cleaned with acid or base wash and silica gel fractionation; and the solvent volume reduced to 150 µL. Each extract is then spiked with 10 µL of RS just prior to analysis by GC/MS.

Samples for both the volatile- and the particulate-phase PAH are analyzed by GC/MS using an Agilent 5973N MSD 30 m by 0.25 mm i.d. DB-5 column with a 0.25 µm film thickness. A calibration curve consisting of at least five points is obtained prior to sample analysis to ensure linearity in the range from 3 pg/μL to 1000 pg/μ, and a mid-point continuing calibration performed each day after the initial five point calibration. All PAH IS and RS are at a concentration of 250 pg/μL. For each analysis, a 1 μL aliquot of the sample extract is injected into the instrument. Analysis for PAH compounds is performed using the positive ion/electron ionization (PI/EI) mode. Two or three characteristic ions for each PAH and one or two characteristic ions for each IS are monitored. Each target compound meets the criterion of a 30 percent relative response factor (RRF) and 30 percent deviation in relation to the mean RRF obtained in the initial and continuing calibrations. A solvent or lab blank are also analyzed immediately after the last calibration to ensure no carryover. Quantitation limits (QL) range from 2 to 10 ng per PAH for the PUF/XAD/PUF samples and 2 ng per PAH for the filter samples.

Data Analysis and Reporting

The test plan described above delivers triplicate determinations of the combustion products from both CARB E10 and CARB Bu16 fuels taken both with and without a catalytic converter. These data are then analyzed to determine the presence or absence of statistically significant differences, between the combustion products with the two fuels either with or without a catalytic converter.

Results:

The combustion products of the test fuels containing 16 vol % isobutanol is in compliance with CARB requirements. The test fuels containing 16 vol % isobutanol exhibit the same or reduced combustion products compared to test fuels containing 10 vol % ethanol. Toxic emissions of the test fuels containing 16 vol % isobutanol do not exceed those of the test fuels containing 10 vol % ethanol.

Example 9

Impact of Butanol on Gasoline Headspace

Figure 2:
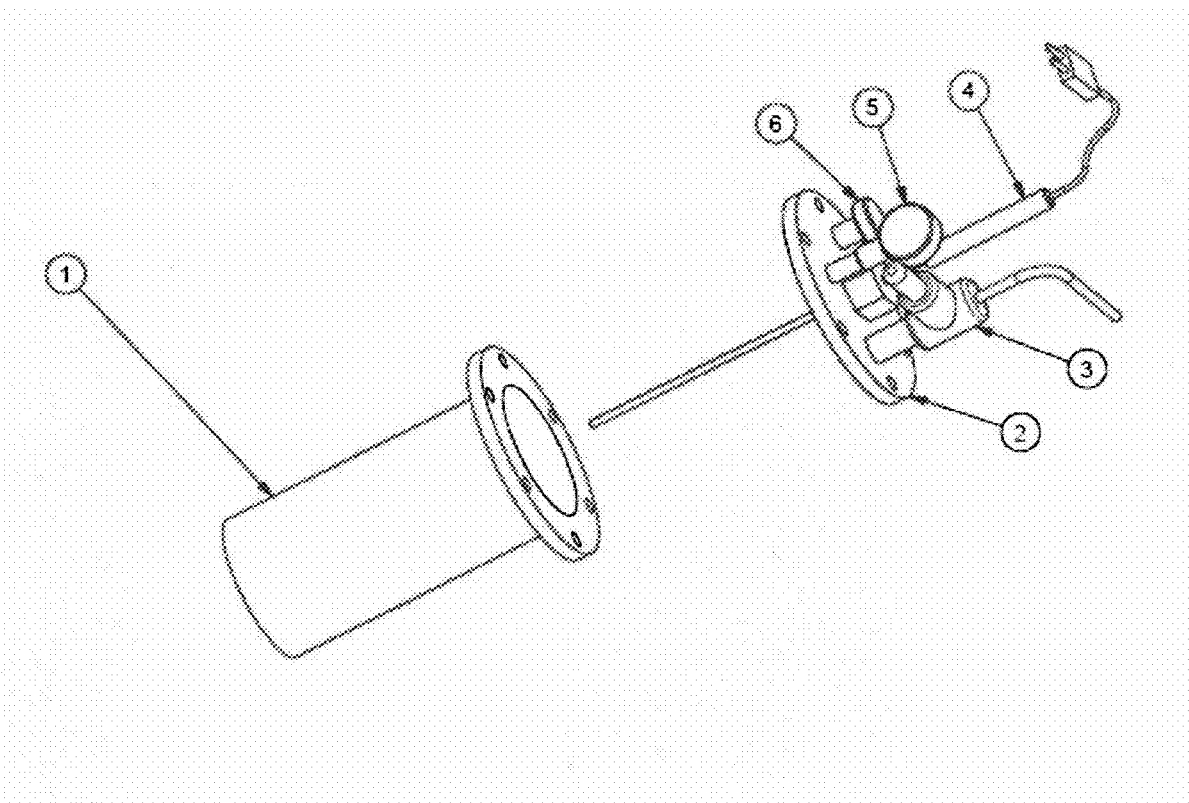
FIG. 2 shows an evaporative emissions generator used in the examples.

Methods:

The purpose of this experiment is to determine the composition of the headspace of 10 vol % ethanol and 16 vol % isobutanol blended California reformulated gasoline blends over a range of temperatures and calculate differences in potency-weighted toxics and reactivity. Evaporative emissions are generated using an evaporative emissions generator (EEG) (shown in FIG. 2) and subsequently speciated a using a gas chromatograph equipped with a flame ionization detector (FID).

Evaporative Emissions Generator

An Evaporative Emissions Generator (EEG) is a fuel tank or vessel which is heated to cause the volatile portion of the fuel or fuel additive to evaporate at a desire rate. A vessel is designed and constructed by Southwest Research Institute® (SwRI®) in accordance with the requirements of the Code of Federal Regulation (CFR) Title 40—Protection of Environment, Part 79—Registration of Fuels and Fuel Additives, Subpart F—Testing Requirements for Registration, Section 79.57—Emission Generation.

The EEG is a stainless steel cylinder with a flange on the top for the introduction of the fuel sample. A bleed valve, closed-tip thermocouple extends to the liquid volume, pressure gauge, and septum-type sampling port are mounted on the top flange. The top flange is bolted onto the main portion of the vessel at the start of each test. A Teflon® ring is used to provide a seal between the bottom and top of the vessel. The assembled vessel is wrapped with a custom-made thermal blanket. The thermal blanket is connected to a temperature controller to maintain the desired test temperature.

Sample Generation

The EEG is filled to 40±5% of its internal volume (375 mL); 150 mL of the fuel or additive/fuel mixture being tested is added using a Class A graduated cylinder, and the vessel is sealed. The remainder of the volume, 225 mL, is ambient air. The temperature of the fuel in the vessel is then raised to the desired temperature (see table 1 for fuel and temperature test permutations). This temperature is maintained for two hours. During this equilibration period, the pressure inside the vessel is monitored and maintained within 10 percent of the ambient atmospheric pressure. Headspace samples are collected after two hours and then at one hour intervals for a total of three samples.

Sample Collection and Analysis

For the purpose of characterizing the evaporative emissions, duplicate samples are collected from the vapor space of the EEG. First, a 100 μL sample is withdrawn with a syringe, injected into a Tedlar® bag filled with 0.5 ft$^3$ of nitrogen and gently mixed to obtain a homogeneous mixture. A sample of this homogenous mixture is immediately analyzed for hydrocarbon species. Hydrocarbons ($C_1$-$C_{12}$) speciation follow a 3 column GC method based the procedures outlined in the CRC Auto/Oil Phase II methods discussed in SAE Paper No. 930142. (Siegl, Walter O., et al. Improved Emissions Speciation Methodology for Phase II of the Auto/Oil Air Quality Improvement Research Program—Hydrocarbons and Oxygenates, SAE Paper No. 930142, 1993.) Second, a 500 μL sample is withdrawn from the vapor space and introduced into a 50 mL volumetric flask filled with the distilled water. Contents of the flask are vigorously shaken and a sample is analyzed for alcohols. Alcohols ($C_1$-$C_8$) speciation is performed following the guidelines outlined in the California Air Resources Board, SOP No. MLD 101, revision 2, January 2005. ("Determination of Alcohols in Automotive Source Samples by Gas Chromatography," California Air Resources Board, SOP No. MLD 101, revision 2, January 2005.) The concentration of all speciated hydrocarbons and alcohols are reported as a percentage of the sampled headspace.

Test Matrix/Permutations

Two base fuels, representative of the extremes of Californian gasoline, are selected for the purpose of the evaporative emissions and combustions emissions testing. A more aromatic gasoline from the BP Chemy Point Refinery is available ("Chemy Point BOB"); a 16 vol % isobutanol blend (Bu16) is prepared from this BOB. A more olefinic (low aromatic) BOB from the BP Carson Refinery ("Carbon BOB") is also available. From this BOB, a Bu16 and an 10 vol % ethanol blend (E10) are prepared. All fuels are blended in compliance with the ARB predictive model (2009).

Evaporative emissions are generated from each fuel at three different test temperatures: 70° F., 105° F. and 130° F. The components of the fuel blends tested and the test temperatures are provided in Table 7.

TABLE 7

Test Fuels and Temperatures

| Base Fuel | Oxygenate | Test Temperatures (° F.) |
|---|---|---|
| Carson BOB | 16% isobutanol | 70, 105 and 130 |
| Carson BOB | 10% Ethanol | 70, 105 and 130 |
| Cherry Point BOB | 16% isobutanol | 70, 105 and 130 |
| 50:50 Mix of Carson E10 and Bu16 | 5% Ethanol + 8% isobutanol | 70, 105 and 130 |

Data Analysis and Report

The composition of the headspace is compared across the four test fuels at each of the three test temperatures. The potency-weighted toxics are calculated for each headspace. The ozone reactivity for the headspace above each fuel is calculated at each test temperature using the Carter Maximum Incremental Reactivity (MIR) methodology to estimate the ozone forming potential of the headspace.

The calculated results for composition, toxicity and reactivity are examined for statistically significant differences.

Results:

The test fuel containing 16 vol % isobutanol has no substantial impact on the composition of the headspace gases when compared the test fuel containing 10 vol % ethanol at the same vapor pressure and seasonal volatility class (ASTM 4814). The test fuel containing 16 vol % isobutanol has no differences in potency-weighted toxics and reactivity when compared the test fuel containing 10 vol % ethanol. The only significant difference is the presence of isobutanol in the headspace associated with the test fuel containing 16 vol % isobutanol rather than ethanol. The headspace gases of the test fuel containing 16 vol % isobutanol are in compliance with CARB requirements.

Example 10

Impact of Butanol on Permeation Emissions

Methods:

The purpose of this experiment is to determine permeation emissions of a hydrocarbon composition comprising butanol relative to a hydrocarbon composition comprising ethanol.

Test Fuels

The following four test fuels are used for this experiment:
1. Non-Oxygenated comparison fuel—"E0"
2. 10 V % Ethanol fuel—"E10"
3. 16 V % Butanol Blend—"Bu16"
4. 50:50 blend of E10:Bu16

The blend RVP and Aromatics levels of the test fuels were matched at 7.0 psi and an effort was made to minimize the differences in aromatic content, distillation and octane (FIGS. 4A-4D). During new vehicle certification, special procedures are required to accurately measure alcohol concentration and mass in an evaporative or exhaust emission sample. These procedures are used during the E65 testing for ethanol, and are required to measure butanol in this program. A known n-butanol standard is used for calibration of the Sealed Housing for Evaporative Determinations (SHED) FID and the gas chromatograph (GC). A 5-ppmV standard is employed for this purpose.

During each SHED test, periodic samples are withdrawn from the enclosure and analyzed with a GC to determine butanol ppmV concentrations. New vehicle certification procedures are used to separate the butanol concentration from the total hydrocarbon (HC) concentration. This requires determination of a response factor of the SHED FID for butanol, subtraction of the corrected butanol ppm from the FID total, independent computation of the mass of butanol, and mass of remaining HC's using average density for each SHED measurement. The two masses (butanol and HC) are then summed to provide the total SHED mass.

Test Vehicles

Seven vehicles used in this study are listed in Table 8. Each vehicle was inspected at time of purchase for any indication of non-representative operation, major repair, or for any modifications to the body or fuel systems. The vehicles are all high-volume, representative in-use samples.

TABLE 8

Vehicle Fleet for Permeation Study

| Make/Model | Cylinders | Displacement | Certification |
|---|---|---|---|
| 2006 Chevrolet Impala | 6 | 3.5 L | Tier 2 Bin 8 |
| 2005 Dodge Caravan | 6 | 3.3 L | LEV II |
| 2003 Toyota Camry | 4 | 2.4 L | ULEV |
| 1994 Ford Taurus | 6 | 3.0 L | Tier 0 |
| 1991 Honda Accord | 4 | 2.2 L | Tier 0 |
| 1985 Nissan Sentra | 4 | 1.6 L | Tier 0 |
| 1981 Buick Riviera | 8 | 5.0 L | Tier 0 |

Test vehicles were drained and filled with non-oxygenated fuel when they arrive at the laboratory. The vehicles were operated on the dynamometer for a minimum of 45 minutes (2×LA-4 preconditioning) at least once per week until dismantled. An incoming vehicle inspection documented the vehicle condition and all identification data including odometer, VIN, engine size, emission identification data, and a description of emission control systems. Digital photographs were included in the vehicle log.

An evaporative system evaluation test was performed and reported before the vehicle was dismantled. The test consisted of an LA-4 preconditioning, drain and 40% fill with non-oxygenated 7.0 psi fuel, 12-36 hour soak, a bag-only FTP exhaust emission cycle, a one-hour hot soak evaporative test, and one 24 hour 65° F. to 105° F. California diurnal test. This was done to verify that the vehicles were performing consistent with their certification.

Figure 3:
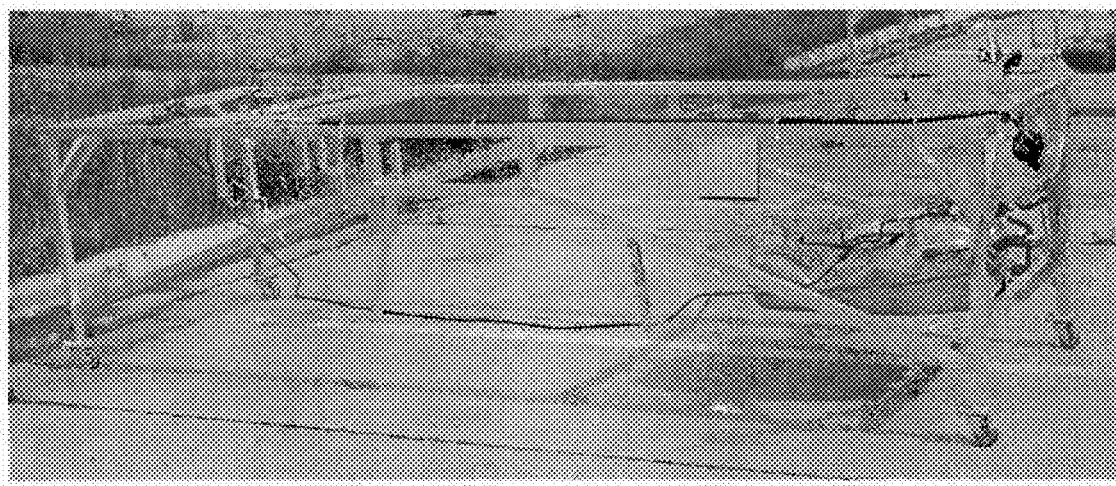
FIG. 3 shows a typical fuel test rig used in the examples.
Figure 4A:
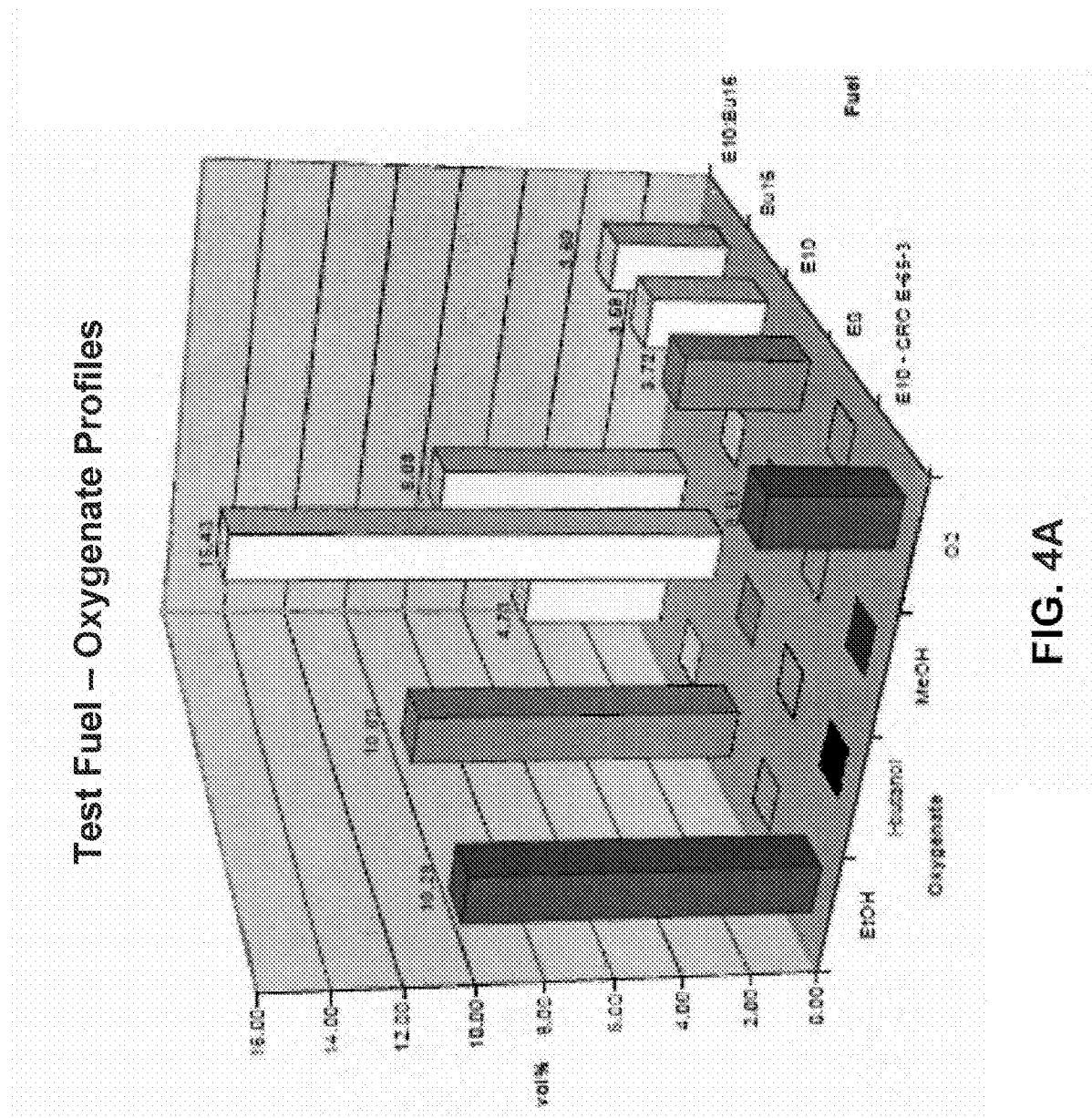
FIGS. 4A-4D show blend RVP and Aromatics levels of test fuels described in the examples.
Figure 4B:
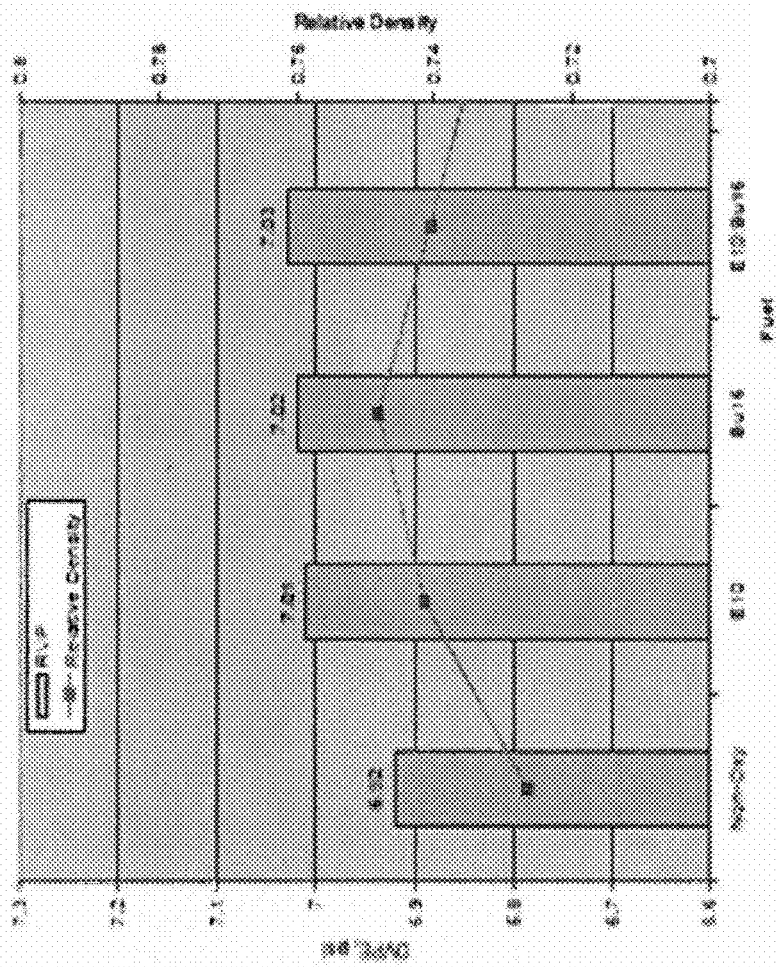
Figure 4C:
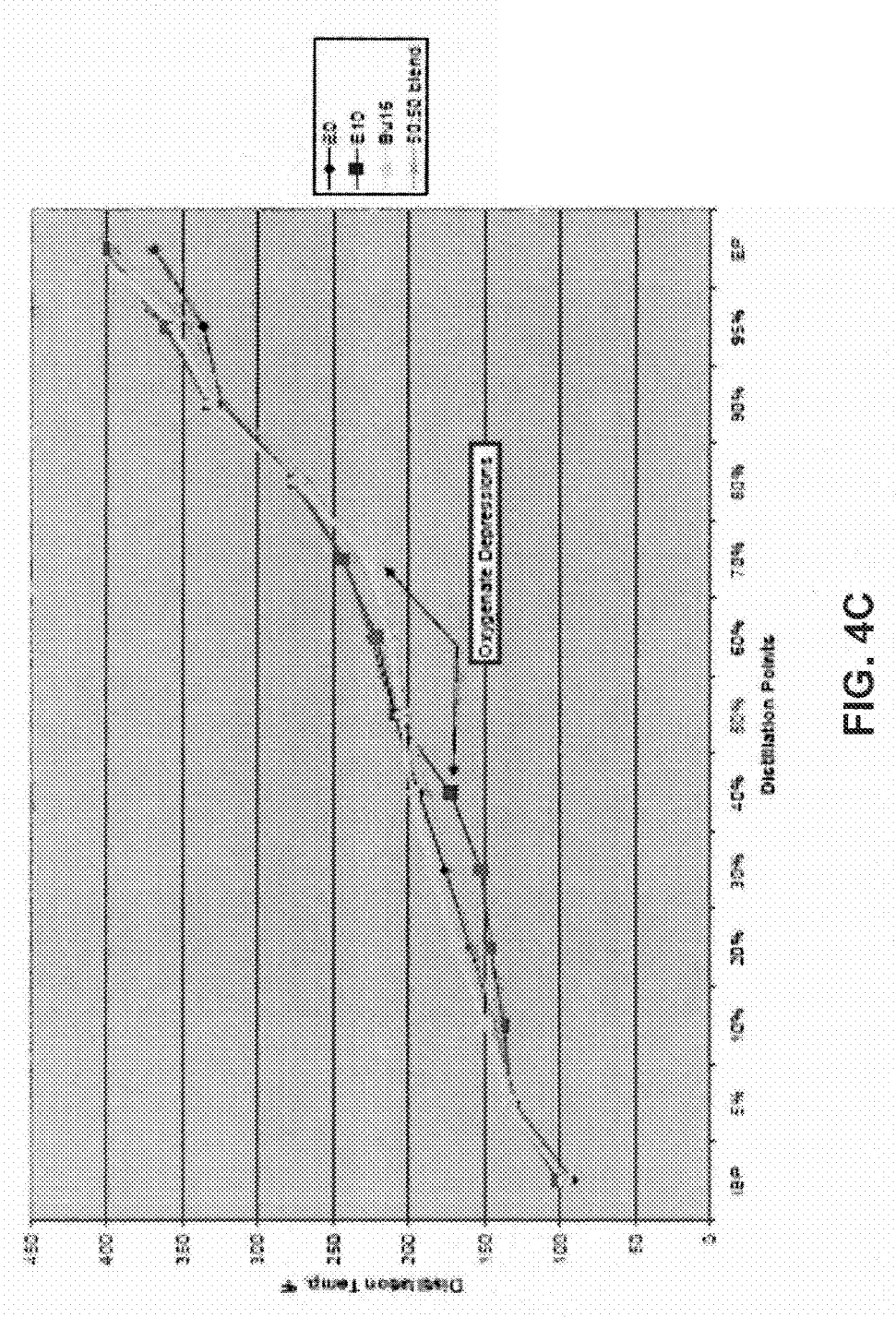
Figure 4D:
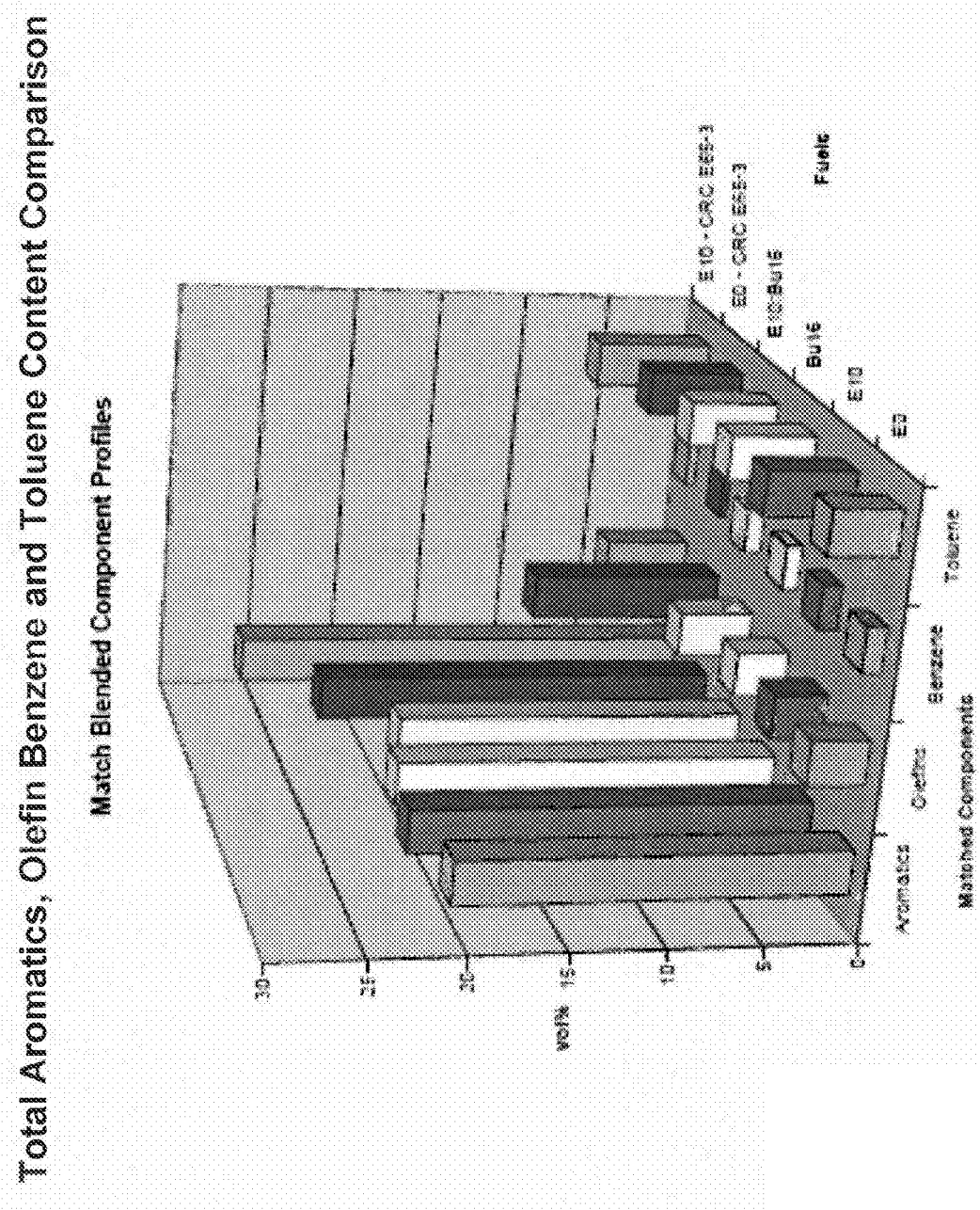

After each vehicle was evaluated and determined to be a suitable candidate, the fuel system was removed from the vehicle and mounted on a custom constructed aluminum frame for testing (the "rig"). A photo of a typical "test rig" is shown in FIG. 3. The fuel tank, fuel inlet and cap, vapor control canister, vapor and purge lines, and fuel lines to the inlet at the manifold were tested. The intake manifold, fuel injectors, and other engine parts were not included in the permeation test. Fuel caps were fitted with a stainless steel Swagelok® adapter to permit venting of the fuel tank vapor space. The outlet of the fuel vapor evaporative control canister was sealed and fitted with a similar adaptor. During testing, fuel vapors were directed from the two rig outlets to matching bulkhead fittings in the SHED wall, using nonpermeable Teflon® hoses. Provisions were made to activate the fuel pump, permitting weekly circulation of fuel in the rig through all OEM lines and hoses. Similar adaptors to operate purge control valves were installed for weekly system purge simulation. All openings, other than the two vent outlets, were fitted with caps and/or valves to positively seal the rigs during testing.

The express purpose and intent of this operation was to insure that only the low-level fuel system permeation emissions existing on the whole vehicle are measured during the test program. No repairs or additional parts were added, and no joints or connections on the vehicle's fuel system were be broken during transfer from vehicle to fuel test rig. The resulting rig represented the fuel system as it previously existed on the production vehicle.

Test Procedures

Each rig was tested with a non-oxygenated base fuel (E0), the 10 Vol % ethanol fuel (E10), the 16 Vol % butanol fuel (Bu16), and a 50:50 blended fuel (E10/Bu16). For each fuel, the test rig received a fuel flush with the test fuel, stabilization, and were evaluated weekly in the SHED at 105° F. to determine when the steady state permeation had stabilized.

Figure 5:
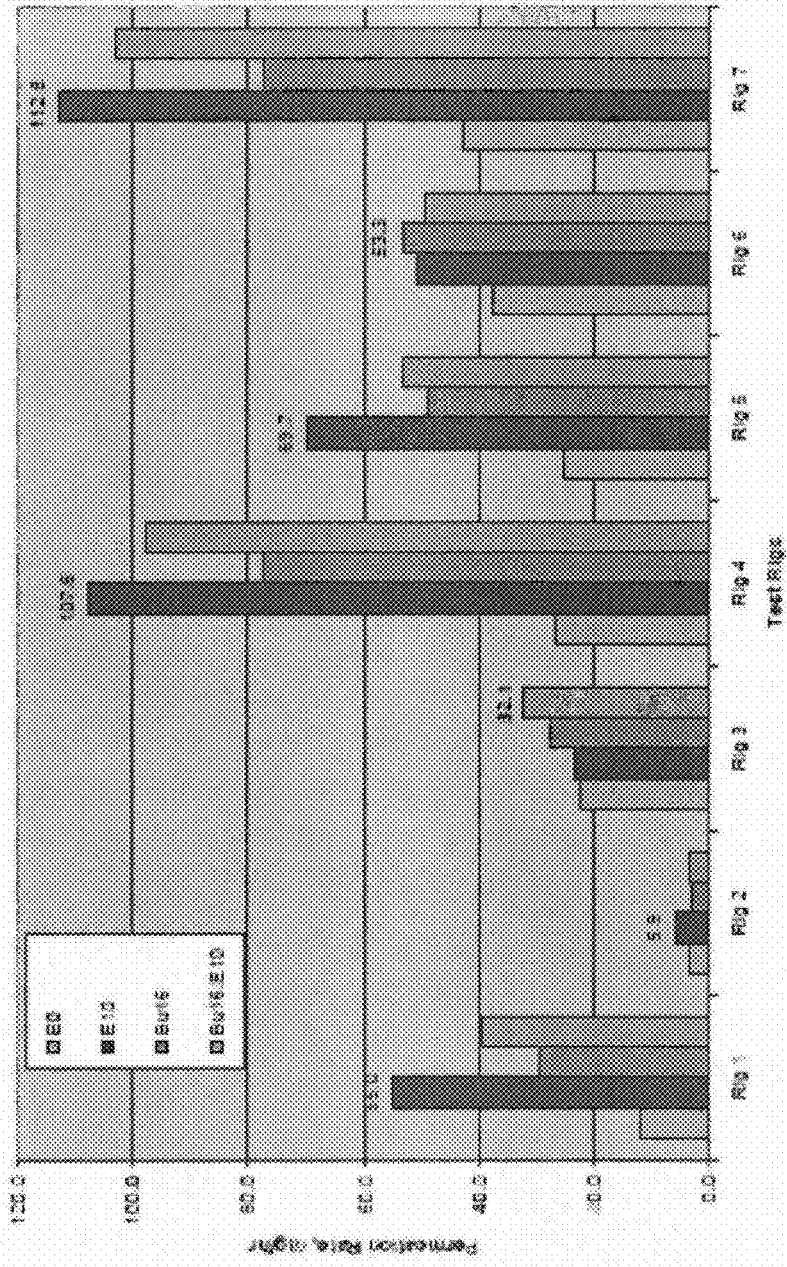
FIG. 5 shows steady state stabilization permeation results described in the examples.

The stabilization period began with a fuel flush and 100% fill with the appropriate test fuel. Once each week, the rig was transferred to a SHED for a 5-hour steady-temperature permeation stability check. The weekly result, and a running three-week average result, was reported. A rig is considered stable when the last of three consecutive running average results "reverses" the trend seen in the previous two. For example, a rig's first two running averages can show a steady decrease in readings, whereas the third running average can reverses this trend and show an increase. At this time, the rig is considered stabilized with the new fuel. Steady state stabilization permeation results are shown in FIG. 5. The general trend in the test fleet was increasing steady state permeation in the following order: E0<Bu16<E10:Bu16<E10.

Figure 6A:
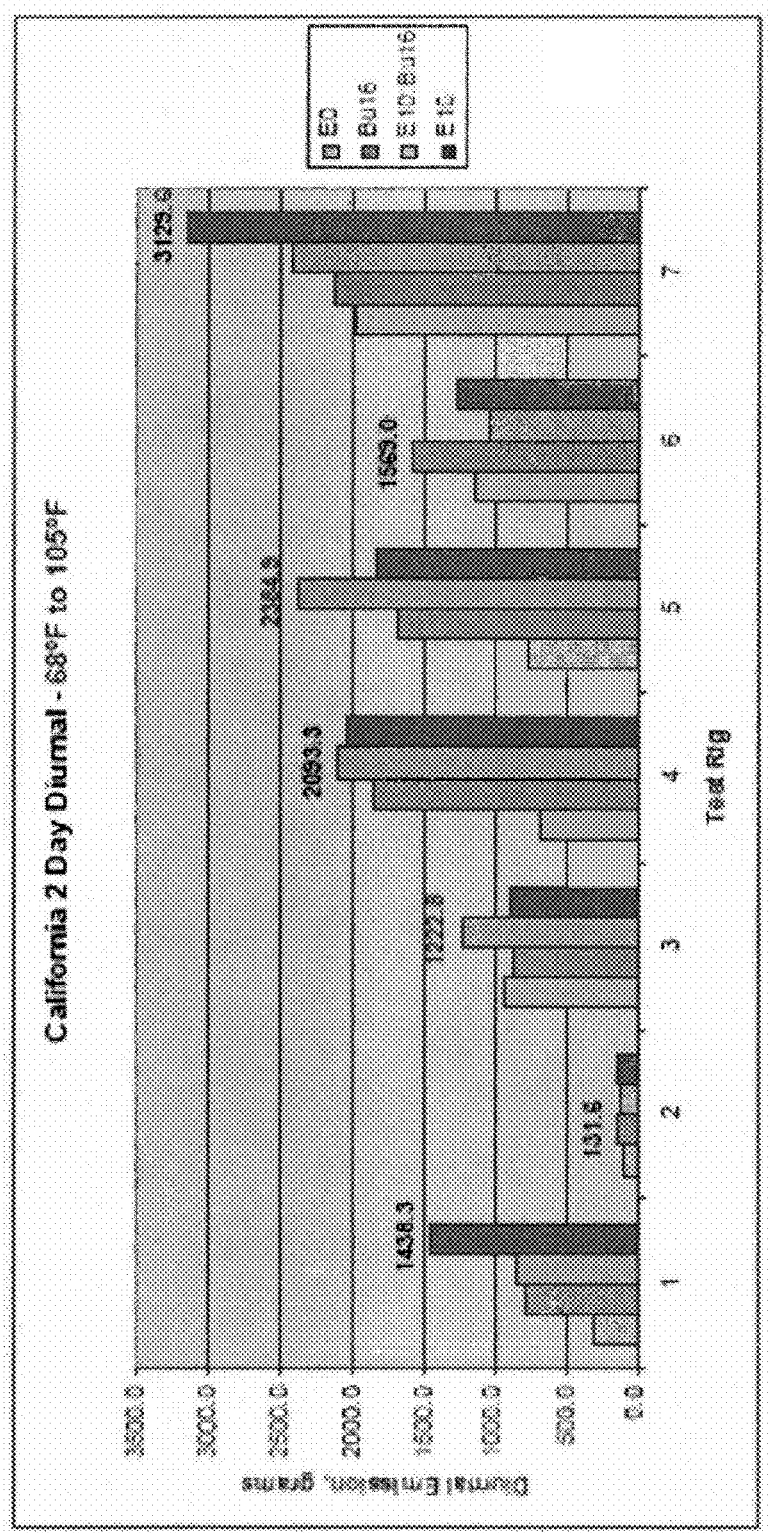
FIGS. 6A-6C show diurnal emissions results described in the examples.
Figure 6B:
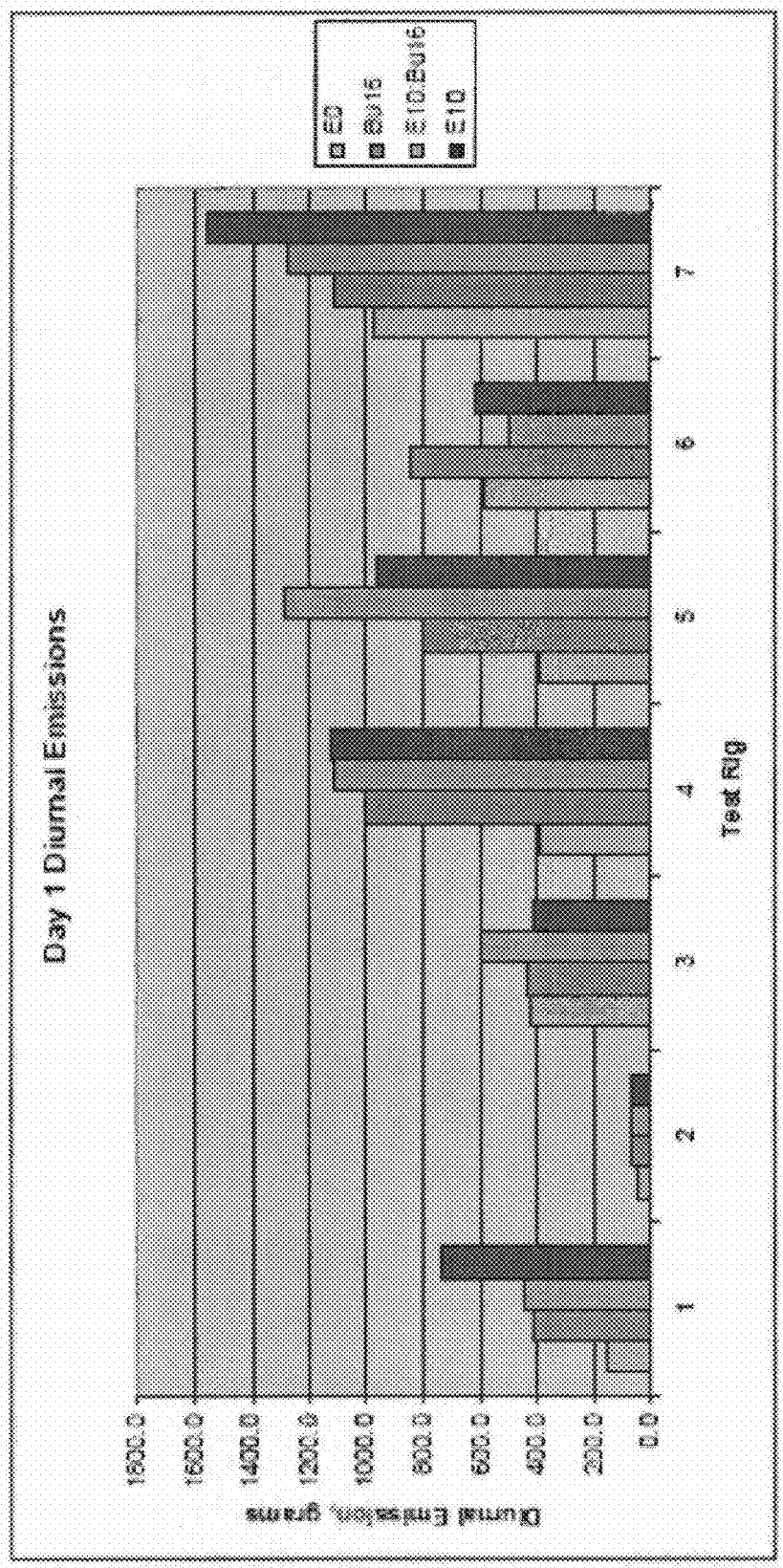
Figure 6C:
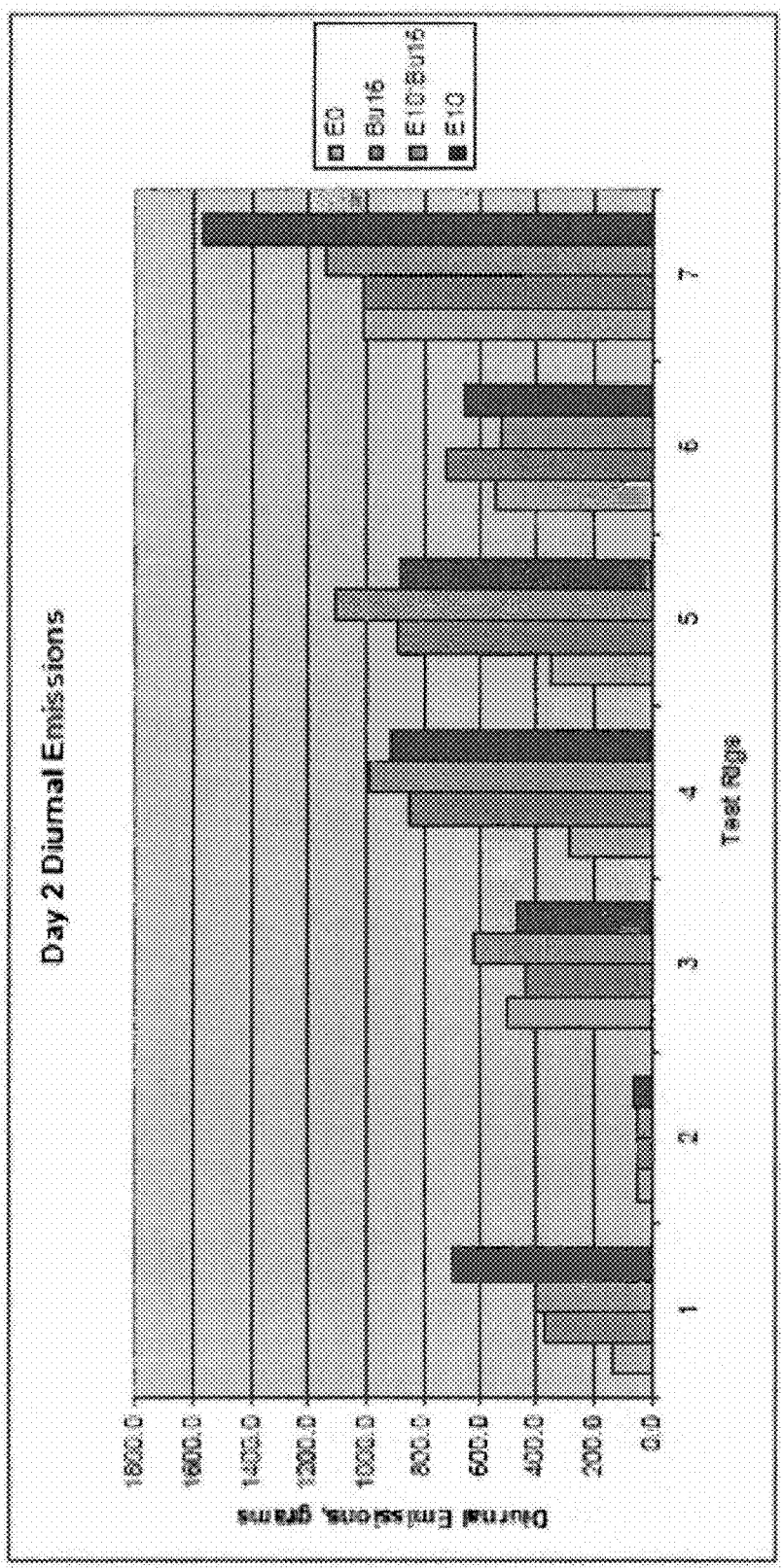

When the rig and fuel had stabilized, a final diurnal test was performed. Fresh fuel was used for the diurnal test. A two-day California diurnal temperature cycle (65° F.-105° F.) was performed. The SHED atmosphere received detailed speciation analysis for each diurnal day. When all test results are complete, the rig was then readied for the next fuel evaluation. The process was repeated until all three fuels had been tested and results deemed complete. Diurnal emissions results are shown in FIGS. 6A-6C.

Figure 7:
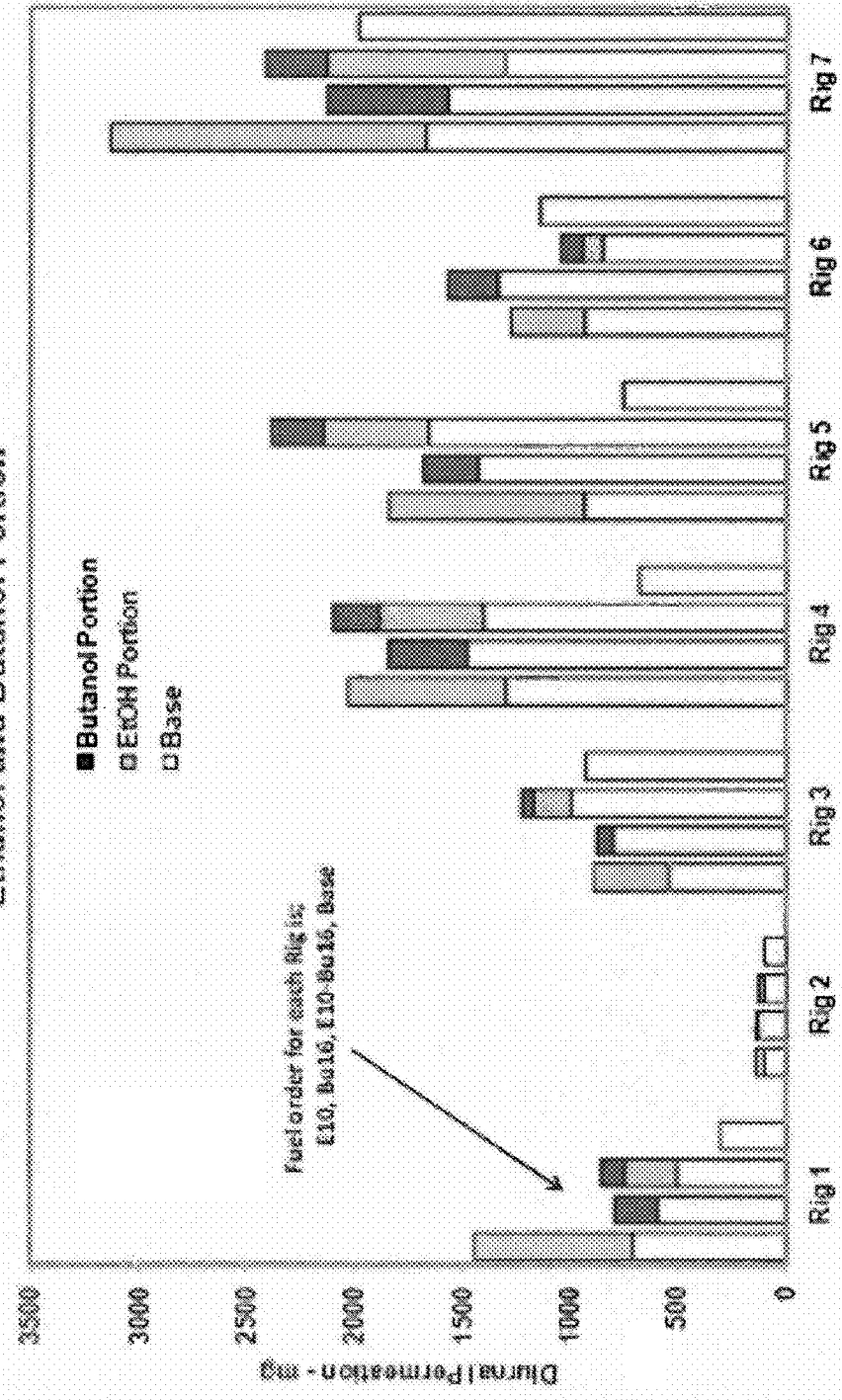
FIG. 7 shows a general permeate profile for test fuels described in the examples.

The following provides a synopsis of the detailed test procedures:

Fuel Change Procedure
1. Drain existing fuel
2. 10% fill with fuel for upcoming test
3. Rock rig to wash walls
4. Activate fuel pump to circulate
5. Drain & fill 10%
6. Repeat rig rocking and fuel circulation
7. Drain and fill 100%
8. Place rig in soak Weekly Fuel Circulation—2 Days Before Test
1. Extend a fuel line from fuel outlet to tank inlet
2. Activate fuel pump for 5 minutes—ensure fuel is flowing
3. Restore rig to standard condition Weekly Canister and Vapor Space Purge—2 Days Before Test
1. Verify canister outlet is open (OBDII valve open, if required)
2. Connect vacuum pump inlet to purge line, pump outlet to lab exhaust
3. Activate vacuum pump for 15 minutes (0.8-CFM minimum)
4. Restore rig to standard condition Steady State Stability Test
1. Set temperature to 105° F.
2. Evacuate and fill SHED volume compensation bag
3. Transfer rig to SHED.
4. Connect fuel cap and canister outlets to SHED bulkhead fittings.
5. Verify Teflon lines do not have condensation to block free flow.
6. Locate ambient temperature probe under fuel tank on rig
7. Allow SHED temperatures to stabilize
8. Seal door and open volume compensation bag
9. Start data logger
10. Zero and span FID
11. Allow rig to stabilize a minimum of one hour before 1st reading
12. Collect GC sample; record initial FID, temperature, and barometer
13. At hour 3 and hour 5 repeat GC sample, SHED readings
14. Check linearity of first 3 observations, continue for additional 2 hours if indicated
15. Return rig to 105° F. soak Diurnal Test
1. Set SHED temperature to 65° F.
2. Drain the tank, fill to 40% with fresh fuel, transfer to SHED when complete
3. Connect fuel cap and canister outlets to SHED bulkhead fittings.
4. Verify Teflon lines do not have condensation to block free flow.
5. Locate ambient temperature probe under fuel tank
6. Allow rig to soak a minimum of 8 hours at 65° F.
7. Evacuate and fill Volume compensation bags
8. Start data logger
9. Zero and span FID
10. Start temperature profile
11. At t=0 hours, t=24 hours, and t=48 hours collect GC bag sample and record FID, barometer and temperature
12. Store rig in main soak room after diurnal test until approved During the diurnal testing, the permeate was speciated to determine the alcohol and hydrocarbon content that was being emitted. FIG. 7 shows a general profile for each vehicle on each oxygenated fuel. The hydrocarbons from the permeate were compared with the hydrocarbon makeup of the fuels. FIGS. 8A-8E show a comparison of the top 20 permeate permeate species.

The ozone reactivity for each fuel was calculated using the Carter Maximum Incremental Reactivity (MIR) methodology. The ozone reactivity is shown in FIG. 9.

Further Analyses

Data were summarized either as ordinary means (i.e. averages) and their associated standard errors or as least square means and their associated standard errors based on various general linear models (GLM's). The following general linear model was used.

$$\text{Diurnal permeation (48 hour)} = \text{constant} + \text{rig} + \text{ethanol presence}(y/n) + \text{isobutanol presence}(y/n) + \text{ethanol presence}(y/n) * \text{isobutanol presence}(y/n)$$

Tests of alternate models indicated that the 3-factor interaction, rig*ethanol presence(y/n)*isobutanol presence(y/n), was not significant. Results for the entire fleet average are shown in FIG. 10.

Figure 10:
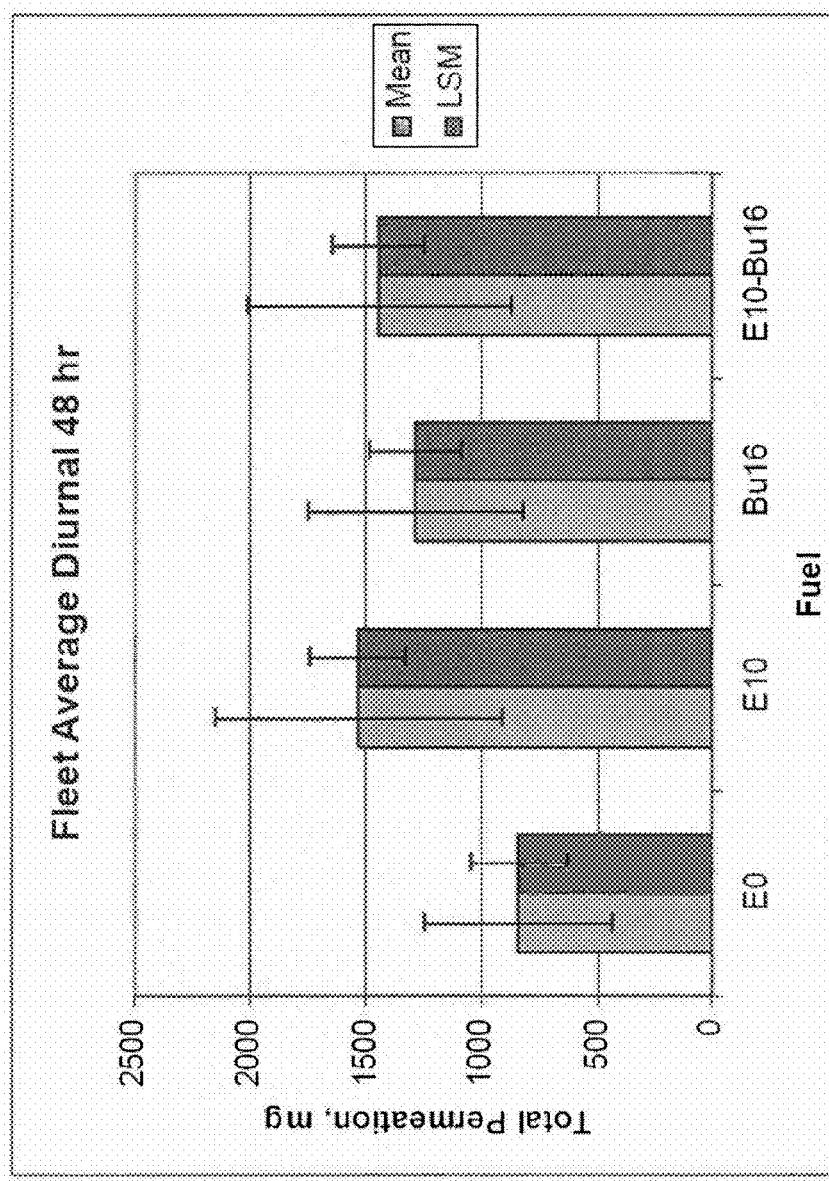
FIG. 10 shows fleet average diurnal permeation results at 48 hours as described in the examples.
Figure 11:
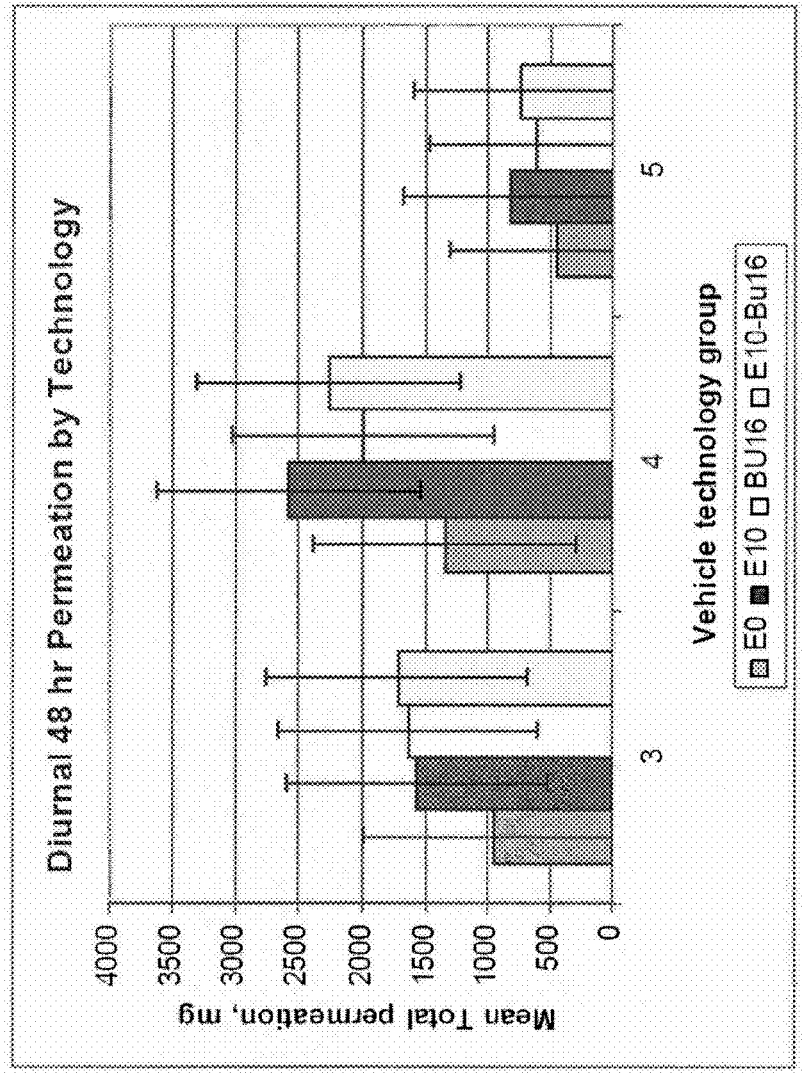
FIG. 11 shows mean total diurnal permeation results at 48 hours by vehicle technology group as described in the examples.
Figure 12:
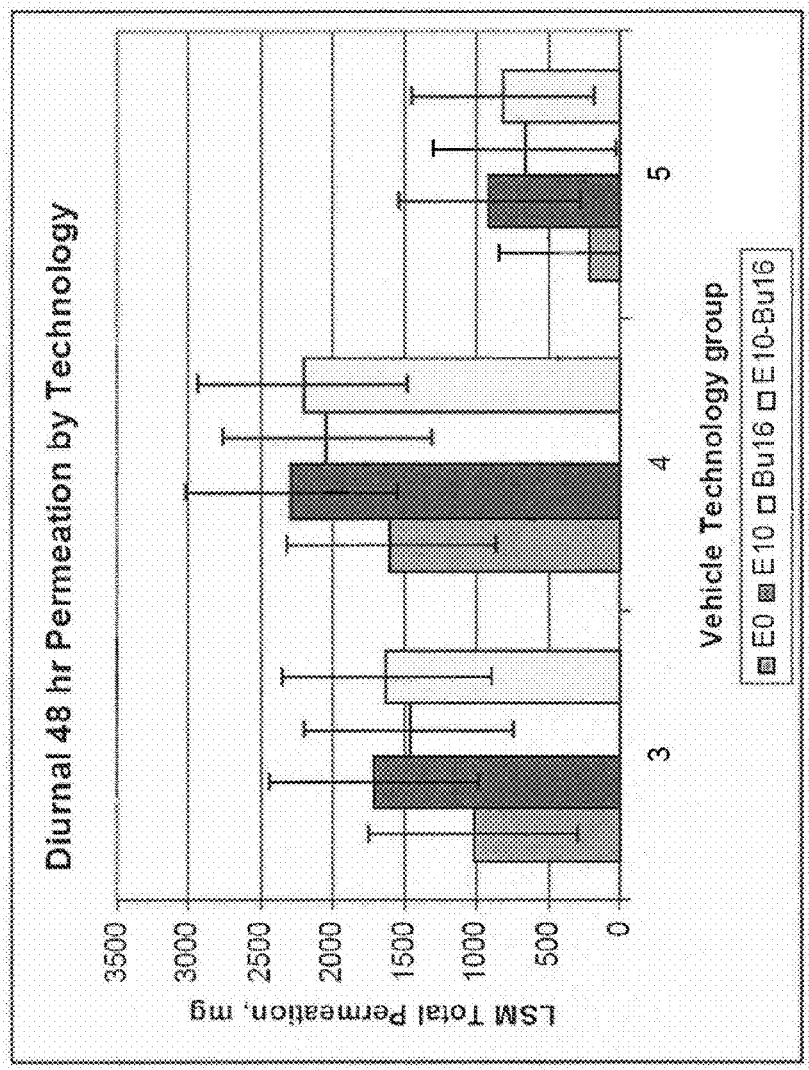
FIG. 12 shows least square mean diurnal permeation results at 48 hours by vehicle technology group as described in the examples.

The error bars in FIG. 10 are least significant intervals (LSI) based on either the standard error (ordinary means) or root mean square error standard errors (GLM). The LSI do not overlap if there is a statistically significant ($P<0.05$) difference between pair wise comparisons of the averages. The LSI's are smaller for the GLM model because the effects of different rigs are removed (i.e. a constant "rig effect" is assumed for each rig independent of the fuel). The GLM results indicate that all the alcohol fuels are higher than the E0 base fuel and that there are no significant differences among all the alcohol fuels. Analyses of the data using vehicle technology group (CARB technology groups) instead of the individual rig gave the results in FIG. 11 and FIG. 12. No significant differences between fuels within each vehicle technology group were observed. The GLM analysis did show significant differences in permeation between vehicle technology groups, 5<3<4, for the average of all fuels tested. The error bars in FIG. 11 and FIG. 12 are based on Tukey's Significant Difference (TSD) test. The estimates of the standard deviations for the ordinary means are based on a pooled estimate.

Figure 13:
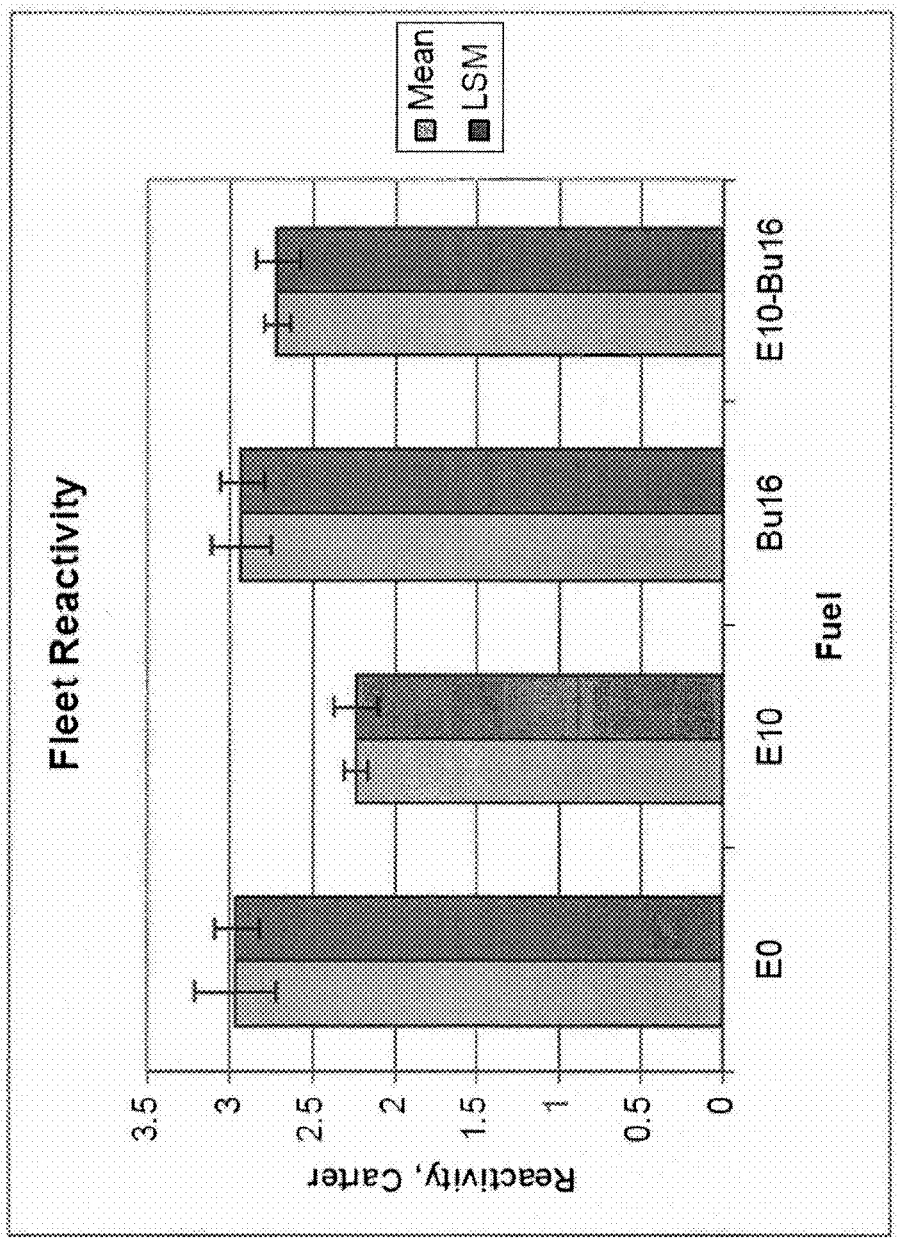
FIG. 13 shows fleet average ozone reactivity results as described in the examples.

Comparisons show that E10 fuel is significantly lower than all the other fuels for both type averages. Also, none of the other three fuels, E0, Bu16, E10-Bu16 are significantly different from one another. The error bars in FIG. 13 are LSI bars.

Figure 14:
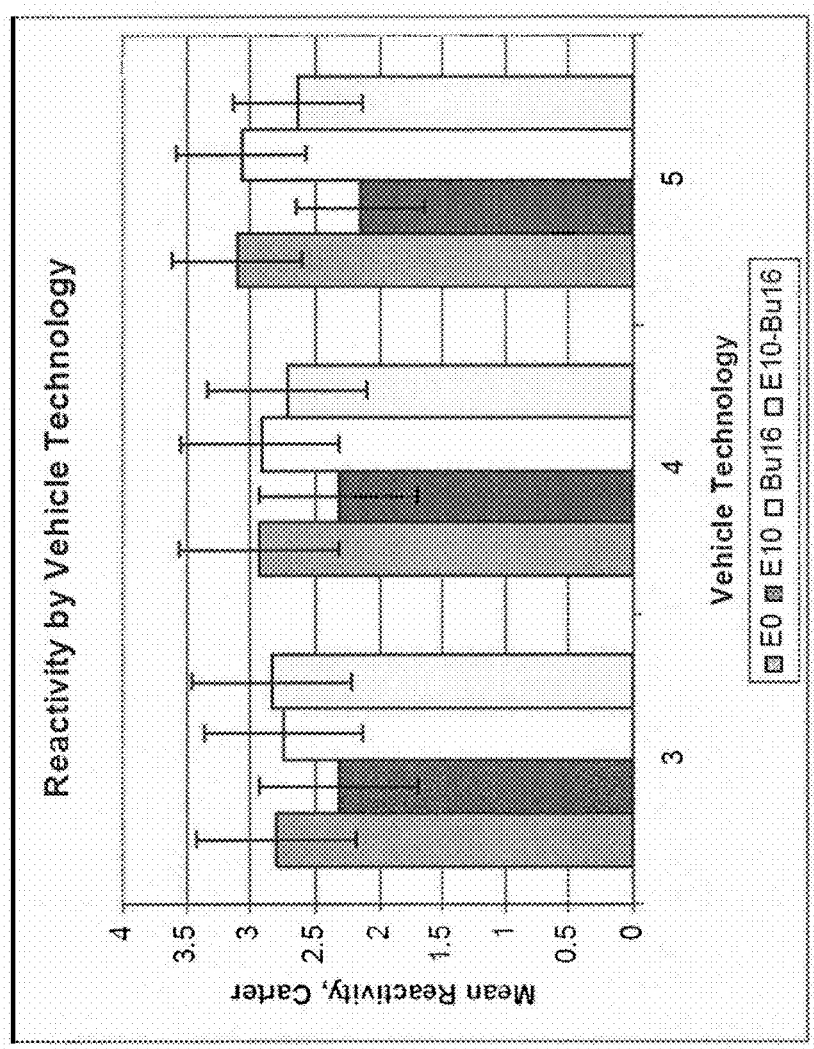
FIG. 14 shows mean ozone reactivity results by vehicle technology group as described in the examples.
Figure 15:
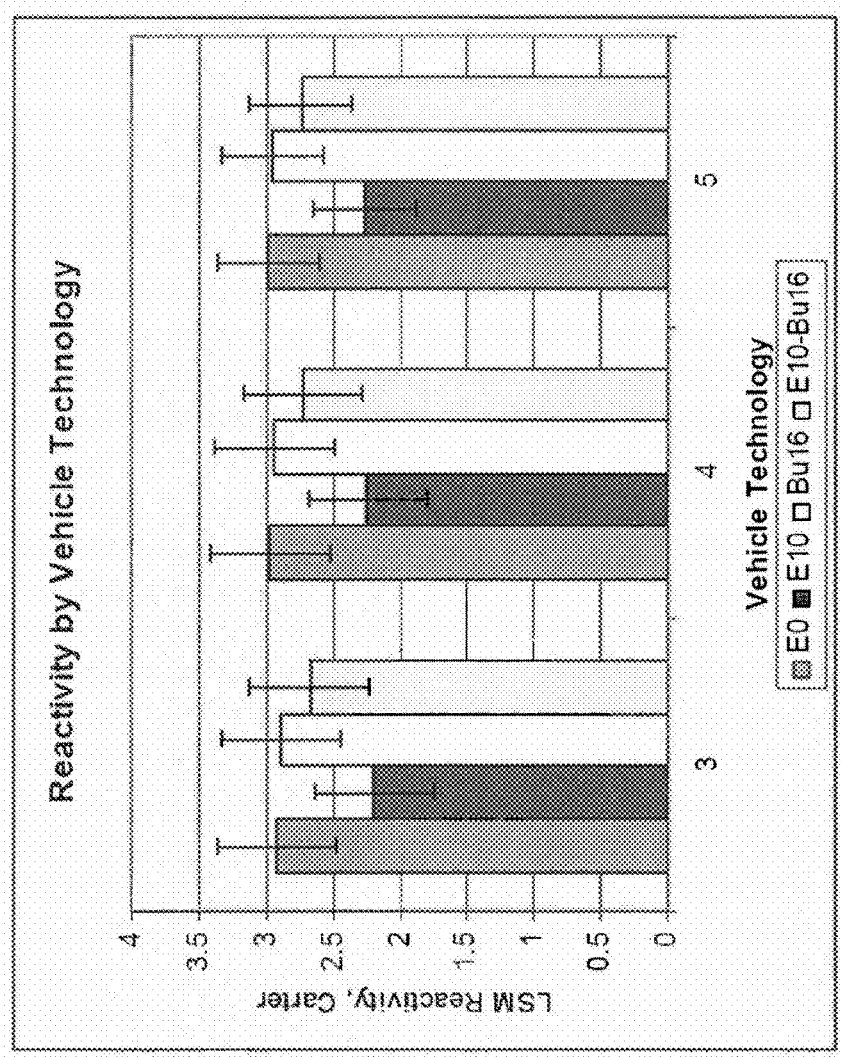
FIG. 15 shows least square mean ozone reactivity results as described in the examples.

Comparisons based on vehicle technology group are shown in FIG. 14 and FIG. 15. As discussed above, the error bars in FIG. 14 and FIG. 15 are based on TSD and estimates of the standard deviations for the ordinary means are based on a pooled estimate. No significant differences between fuels or vehicle technology groups were found by the GLM analysis.

Total permeate from alcohol containing fuels was higher than base fuel (E0). However the reactivity of E10 is less than all the other fuels. This appears to be due to the lower potential ozone formation reactivity of ethanol.

Figure 16:
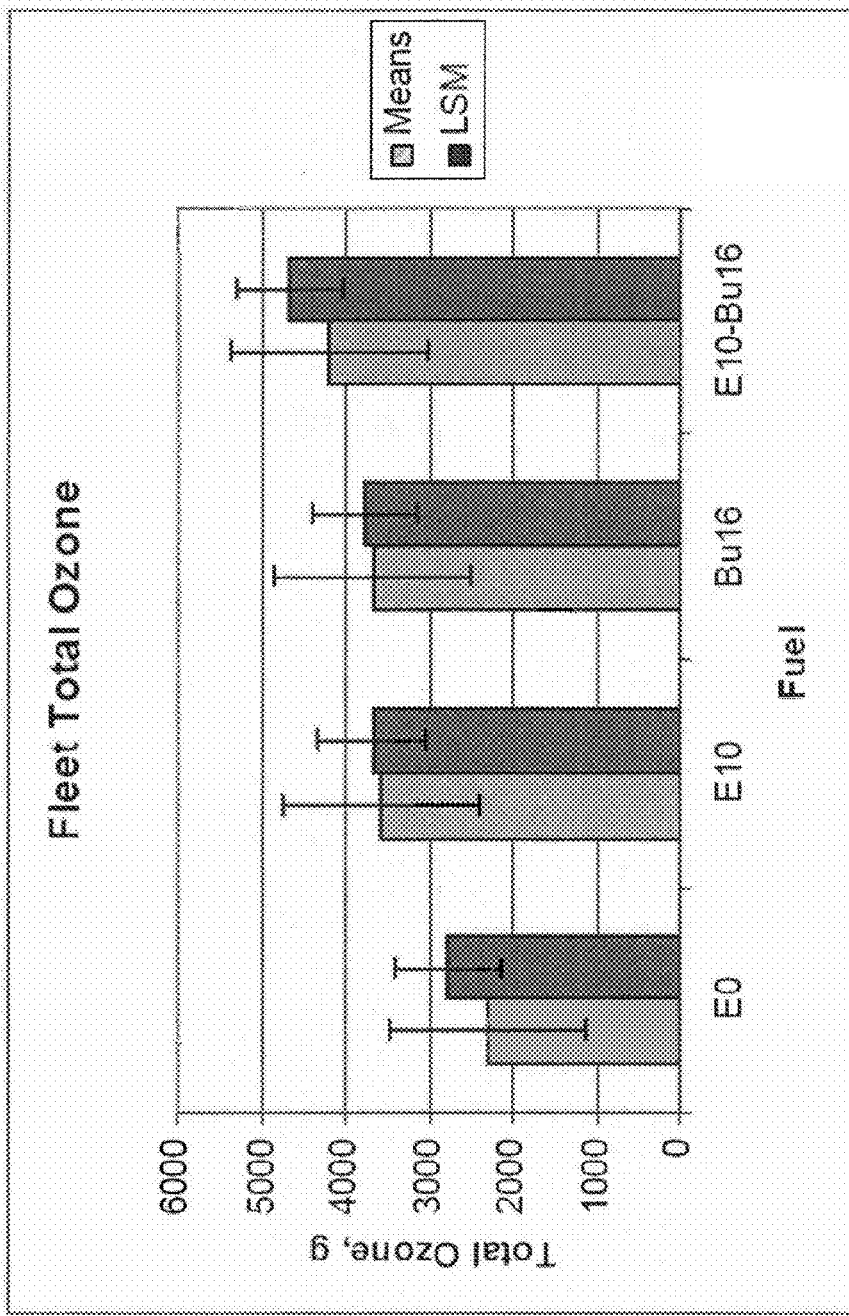
FIG. 16 shows fleet total ozone potential results as described in the examples.

The fleet results, FIG. 16, showed that both E10 and Bu16 were not significantly different than the base fuel, E0. However the mixed alcohol fuel, E10-Bu16, was higher than the base fuel, but not different than the individual alcohol fuels, E10 and Bu16.

Figure 17:
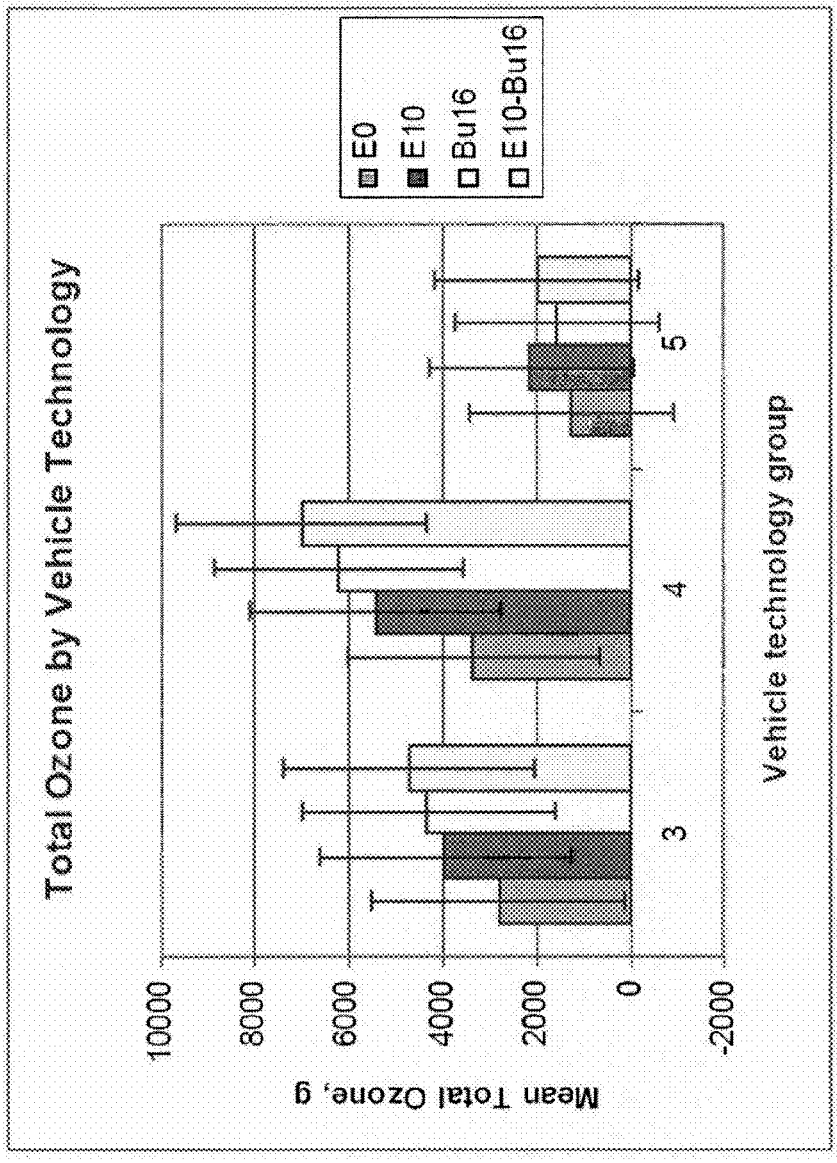
FIG. 17 shows mean total ozone potential results by vehicle technology group as described in the examples.
Figure 18:
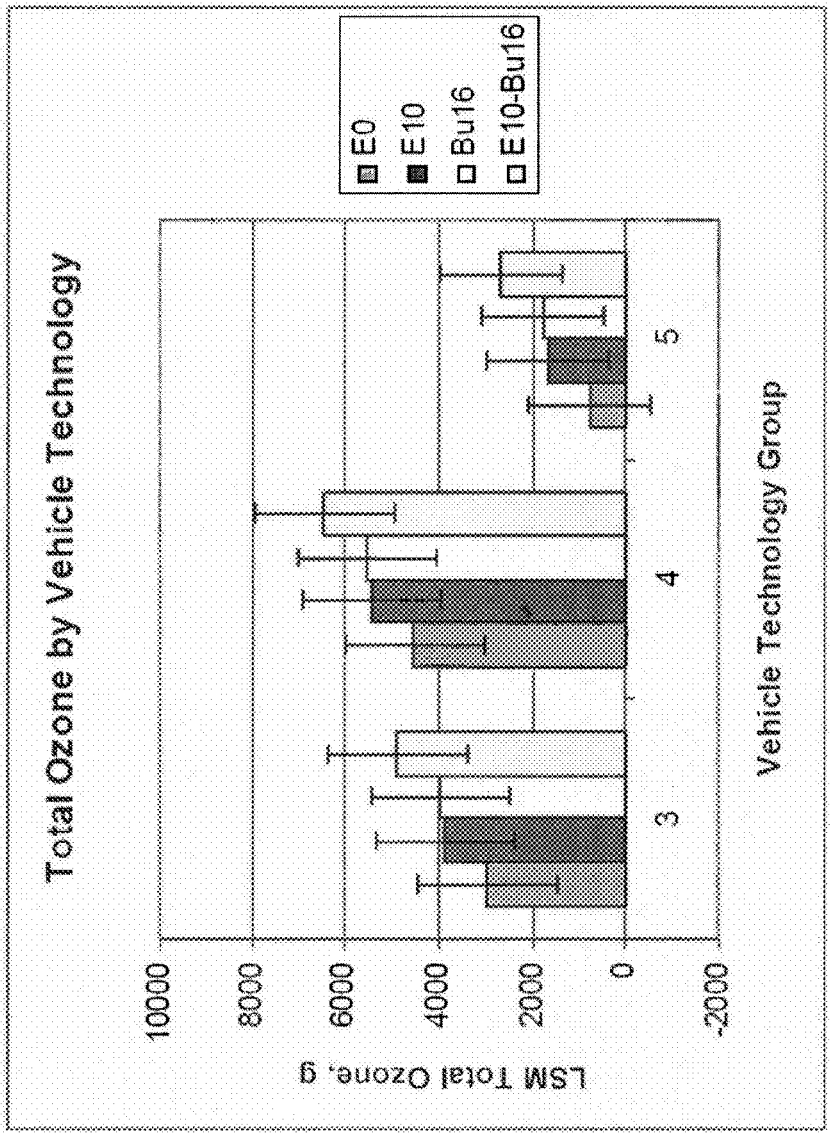
FIG. 18 shows least square mean ozone potential results as described in the examples.
Figure 19:
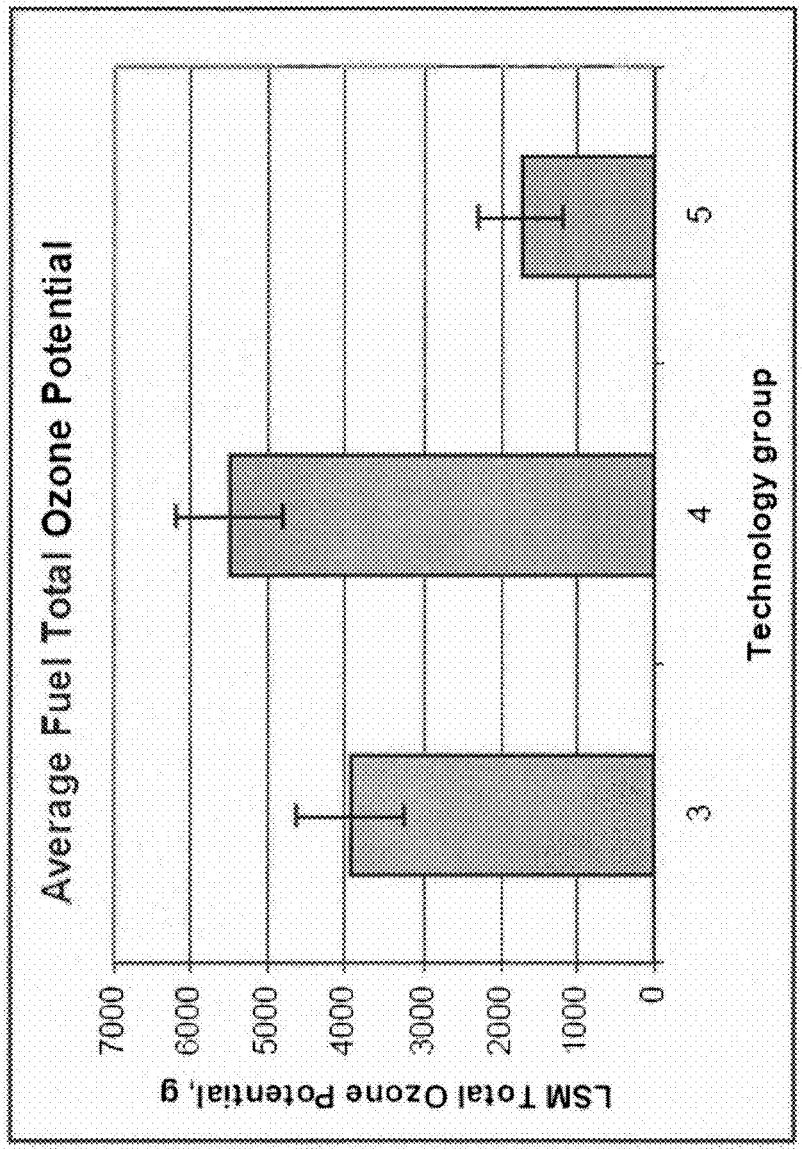
FIG. 19 shows average fuel total ozone potential results as described in the examples.

Results by vehicle technology group are shown in FIG. 17 and FIG. 18. Large variability within technology groups, particularly group 5, leads to wide error limits (TSD) so that no significant differences between fuels were observed within each group. However, there were significant differences in average total ozone potential between technology groups. FIG. 19 shows the averages over all the fuels by technology group. Significant differences rank the technology groups as: Group 5<Group 3<Group 4.

Diurnal testing produced results at 24 (first day) and 48 (second day) hours for all responses of interest. Statistical models were developed to use all the measured data. For total permeate emissions and total potential ozone emissions, a logarithmic transform of the data was used to fit the following model.

$$\text{Ln (Total Emission)} = \text{Day} + \text{EtOH} + \text{BuOH} + \text{EtOH}*\text{BuOH} + \text{Rig} + \text{Rig}*\text{EtOH} + \text{Rig}*\text{BuOH} + \text{Rig}*\text{EtOH}*\text{BuOH}$$

In this model the "Day" is nominal variable and in effect multiplies the total emission by a constant after the inverse transformation, i.e.

$$\text{Total Emission} = \text{Exp(Day)} \times \text{Exp(EtOH} + \text{BuOH} + \text{EtOH}*\text{BuOH} + \text{Rig} + \text{Rig}*\text{EtOH} + \text{Rig}*\text{BuOH} + \text{Rig}*\text{EtOH}*\text{BuOH})$$

First day emissions test=24 hr emissions day 1+$\epsilon$

Second day emissions test=48 hr emissions+$\epsilon$

Second day emissions test−First day emissions test=24 hr emissions day 2+$\epsilon*\sqrt{2}$ where $\epsilon$ is the experimental sampling and analyses errors.

For the models the estimate of the "Day" effect parameter was as expected i.e. 48 hour emissions were about two times the 24 hour emissions. The models were used to predict emissions at 48 hours and their associated standard errors.

Figure 20:
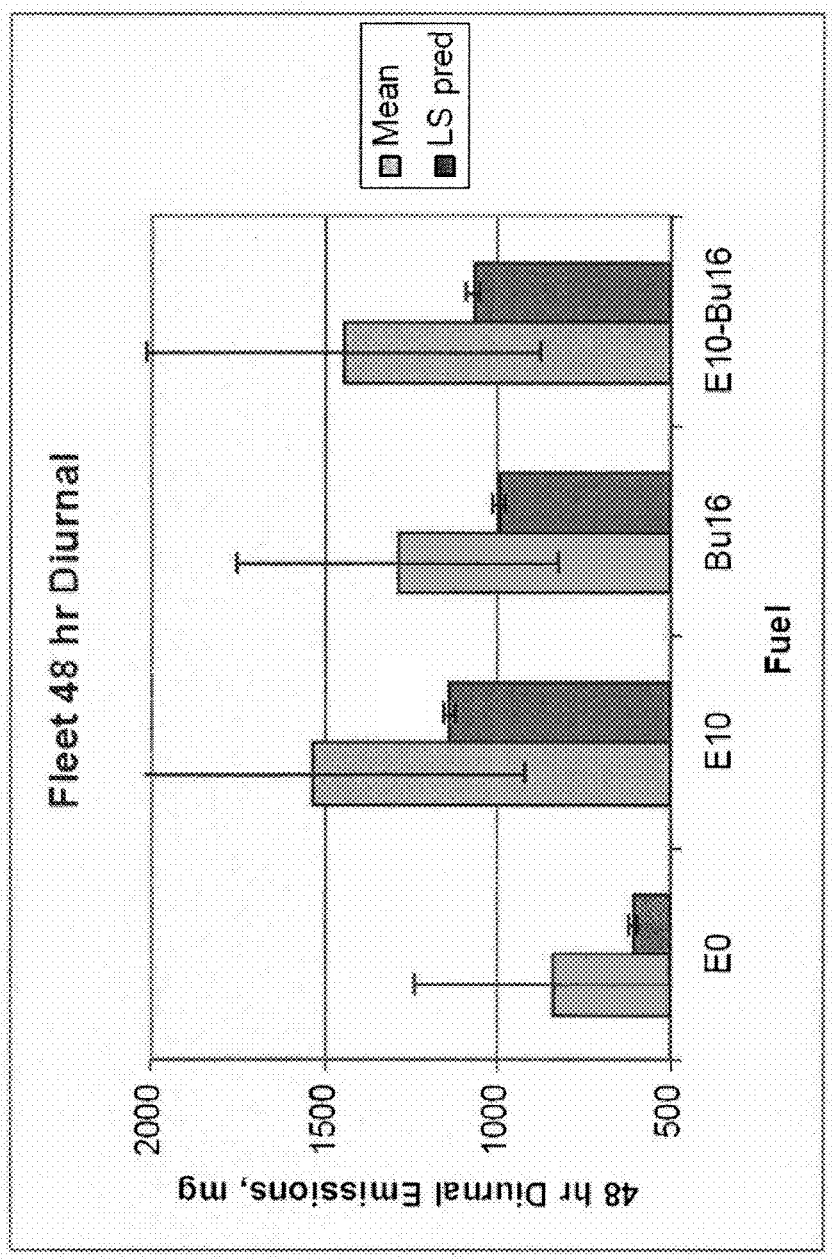
FIG. 20 shows average fleet diurnal emissions at 48 hours as described in the examples.

FIG. 20 shows the results for fleet average 48 hour diurnal emissions. These results are consistent with the above analyses and they also show significant differences between the various alcohol fuels. In particular, Bu16 permeation is less than E10 and the mixed fuel is higher than Bu16, but lower than E10.

Figure 21:
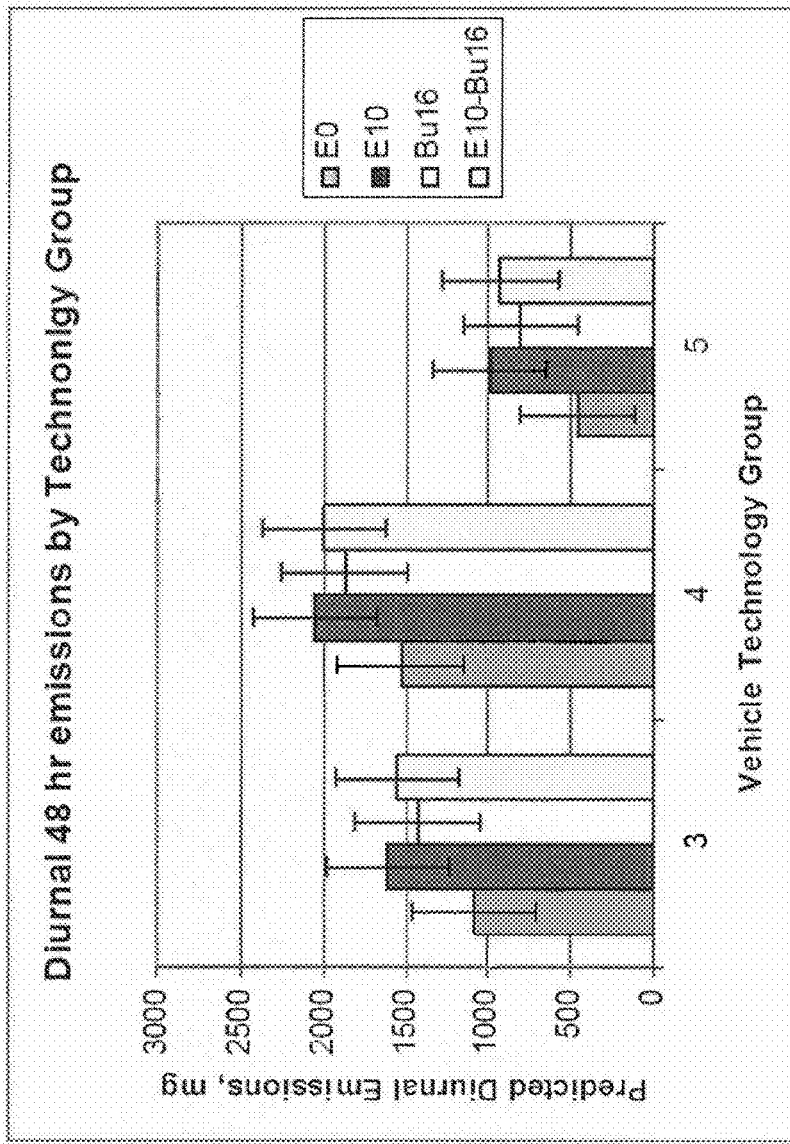
FIG. 21 shows average predicted diurnal emissions at 48 hours by technology group as described in the examples.
Figure 22:
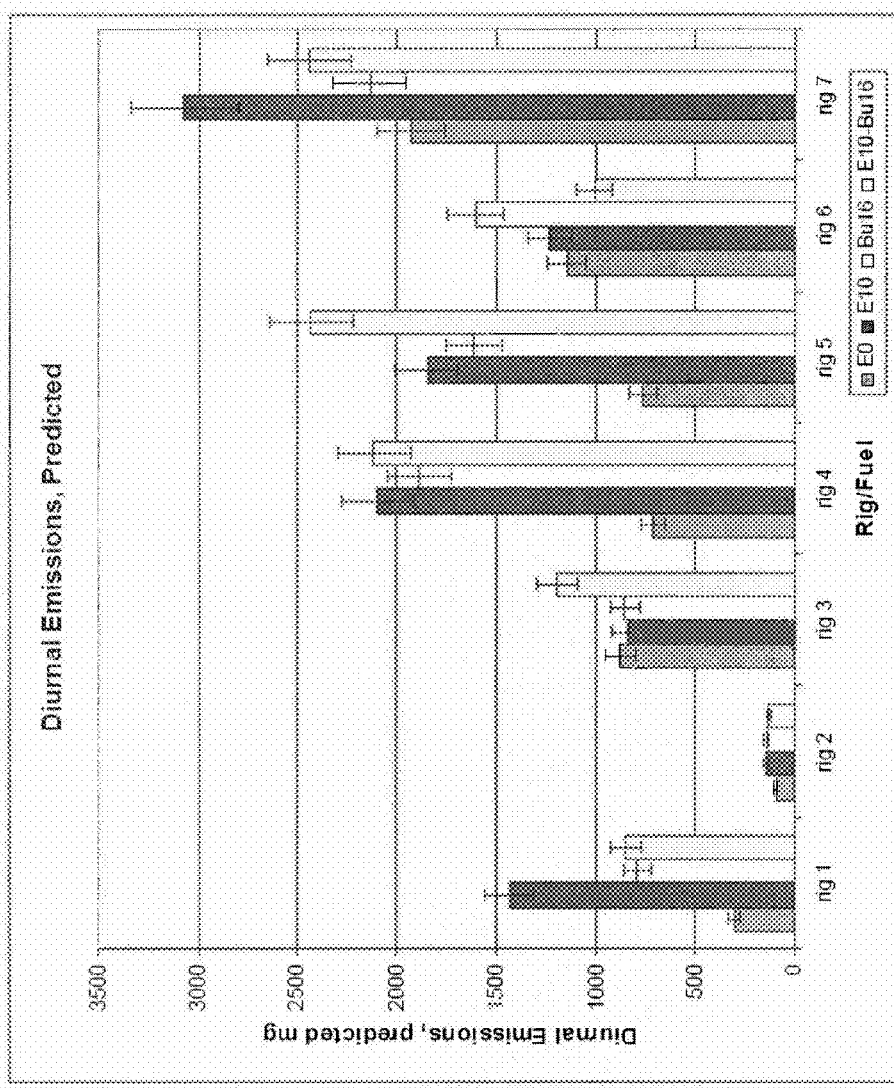
FIG. 22 shows rig average predicted diurnal emissions at 48 hours as described in the examples.

Variability within the technology groups leads to wide comparison limits, FIG. 21. However, individual rig averages with error bars can be evaluated because each rig/fuel combination has at least two test results (i.e. 24 and 48 hours). FIG. 22 shows results for making comparisons. Several significant differences for comparisons between fuels of interest can be made.

a. The Bu16 fuel is the same or less than the E10 fuel in all except one case, rig 6.

b. The combined alcohol fuel, E10-Bu16, is the same or less than the E10 fuel in all except two cases, rigs 3 and rig 5.

Figure 23:
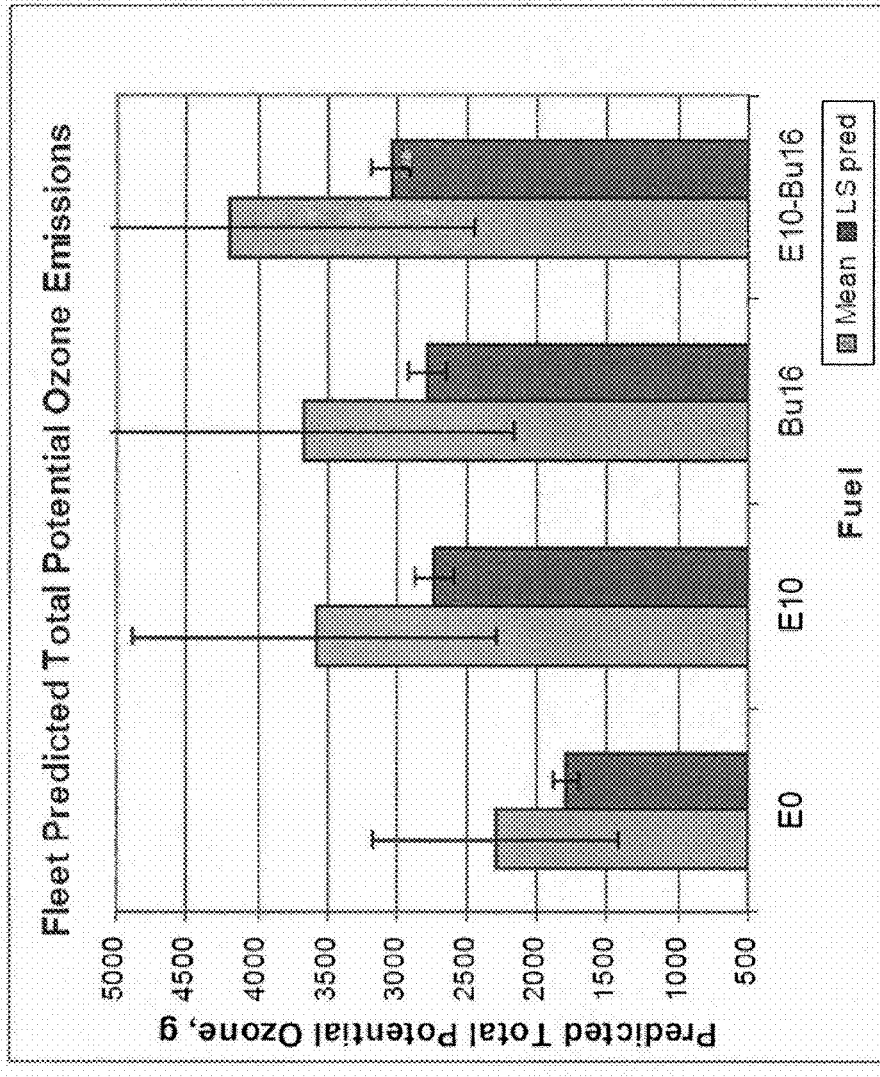
FIG. 23 shows the results for fleet average 48 hour total potential ozone emissions as described in the examples.

FIG. 23 shows the results for fleet average 48 hour total potential ozone emissions. These results are consistent with the above analyses. However they also show a significant difference between the mixed alcohol fuel, E10-Bu16 and the E10 fuel. The difference is significant (P=0.034) and equals 11.6% with 95% confidence limits of 0.9% and 22.2%. While the mean results show these effects in magnitude, their wide error bars do not show them as significant differences.

Figure 24:
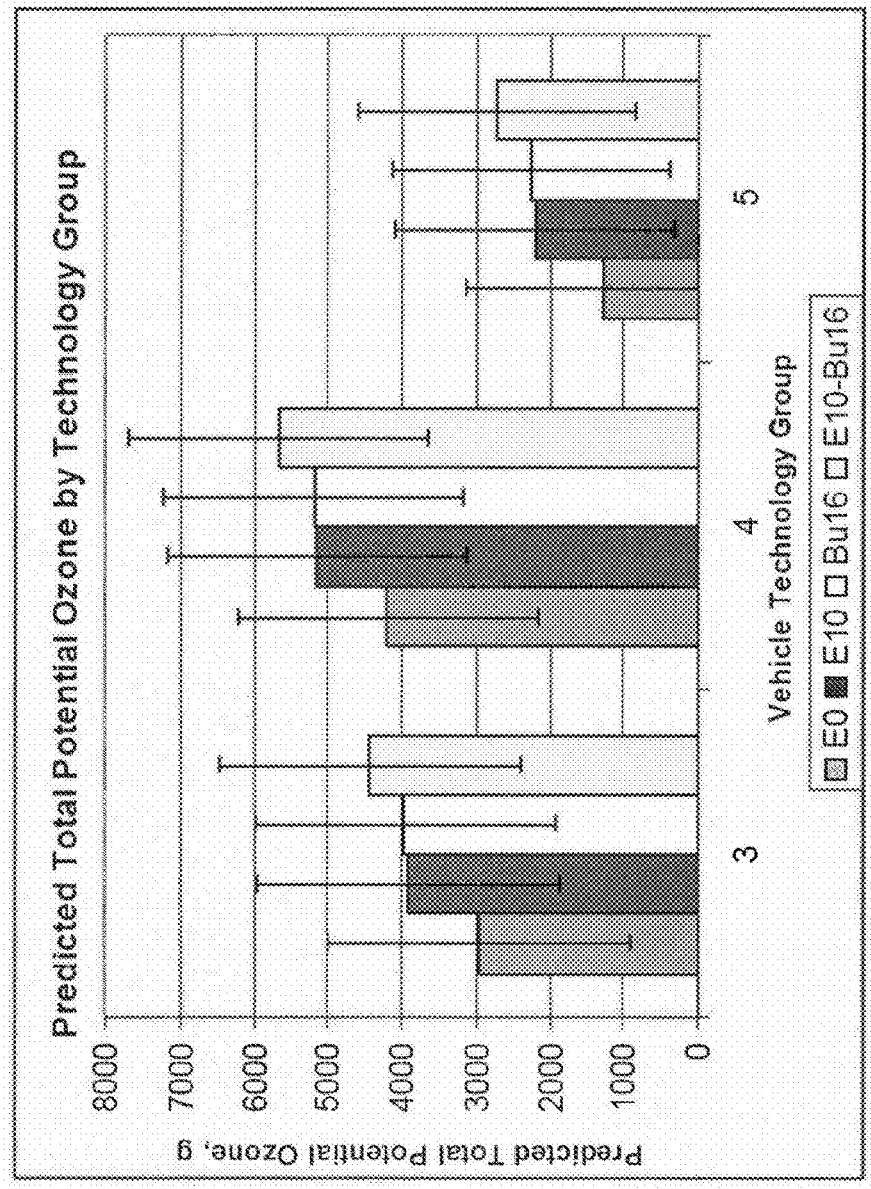
FIG. 24 shows predicted total potential ozone emissions by technology group as described in the examples.

As noted above the large variability within the technology groups leads to wide comparison limits, FIG. 24.

Figure 25:
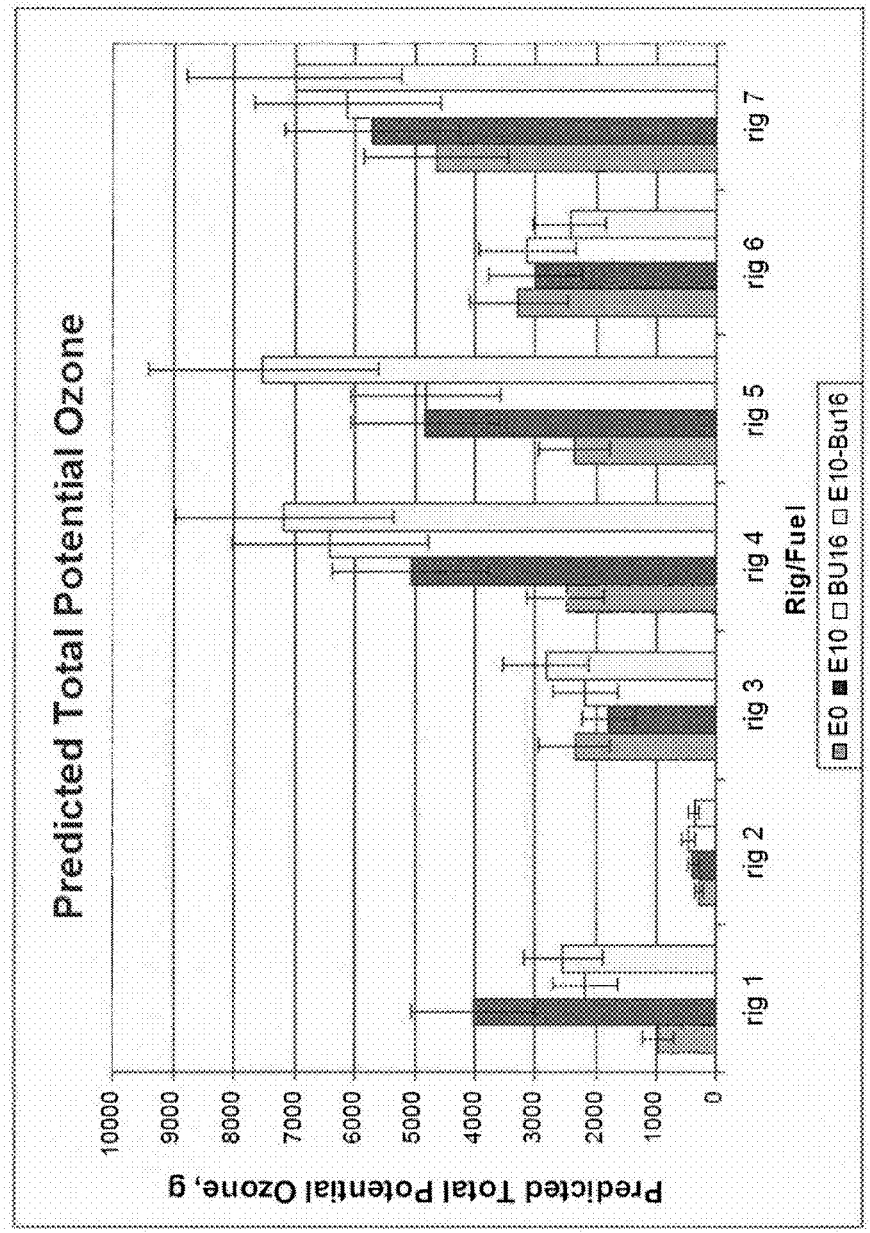
FIG. 25 shows the results for total potential ozone formation emissions by rig as described in the examples.

FIG. 25 shows the results for total potential ozone formation emissions by rig. Comparisons between fuels of interest show the following:

a. The Bu16 fuel is the same or less than the E10 fuel in all cases.

b. The combined alcohol fuel, E10-Bu16, is not significantly different than the E10 fuel in all cases.

For permeate reactivity, the data were fit to a GLM using only the significant factors from a complete factorial design in the factors EtOH, BuOH and Rig. A transform was not needed because the reactivity is calculated by dividing total ozone formation potential by the mass of VOC. This calculation converts the 24 and 48 hour data to the same units, i.e. reactivity=total ozone formation potential (g)/total VOC (g). The variable "day" was not statistically significant in the model.

Figure 26:
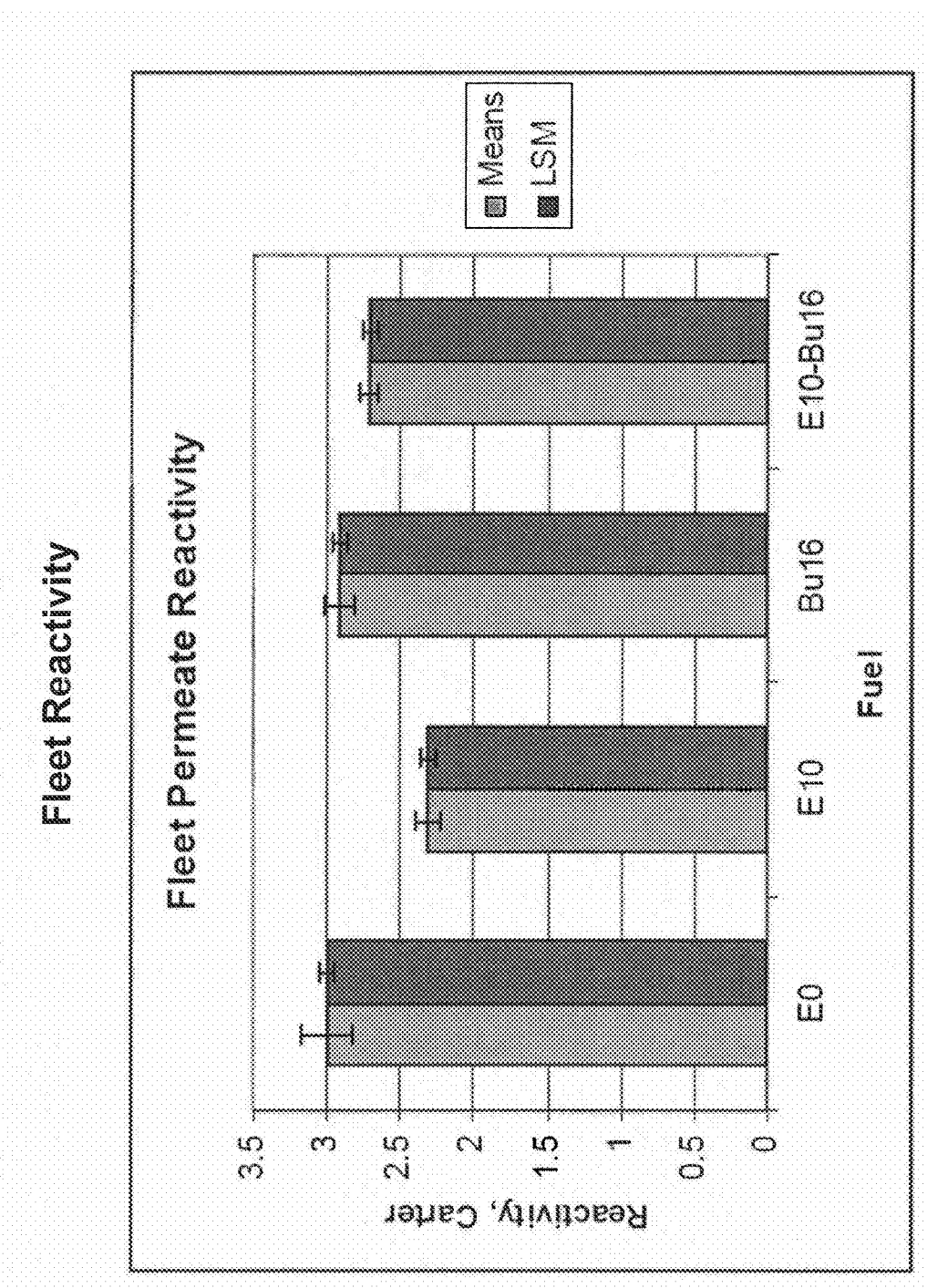
FIG. 26 shows the results for fleet average reactivity as described in the examples.

Results for the fleet average reactivity are shown in FIG. 26. The results are consistent with those described above in that the E10 fuel had lower reactivity than all the other fuels. However an additional significant difference was detected for the mixed alcohol fuel, E10-Bu16, having lower reactivity than the Bu16. This was true for both the GLM results and the ordinary means. Note that the ordinary means are based on both the 24 and 48 hour data because these data should be the same (It is not expected that the second 24 hour period should have different species or relative levels of those species.) The results are in accord with the effect of lower reactivity of ethanol compared to hydrocarbons or isobutanol.

Figure 27:
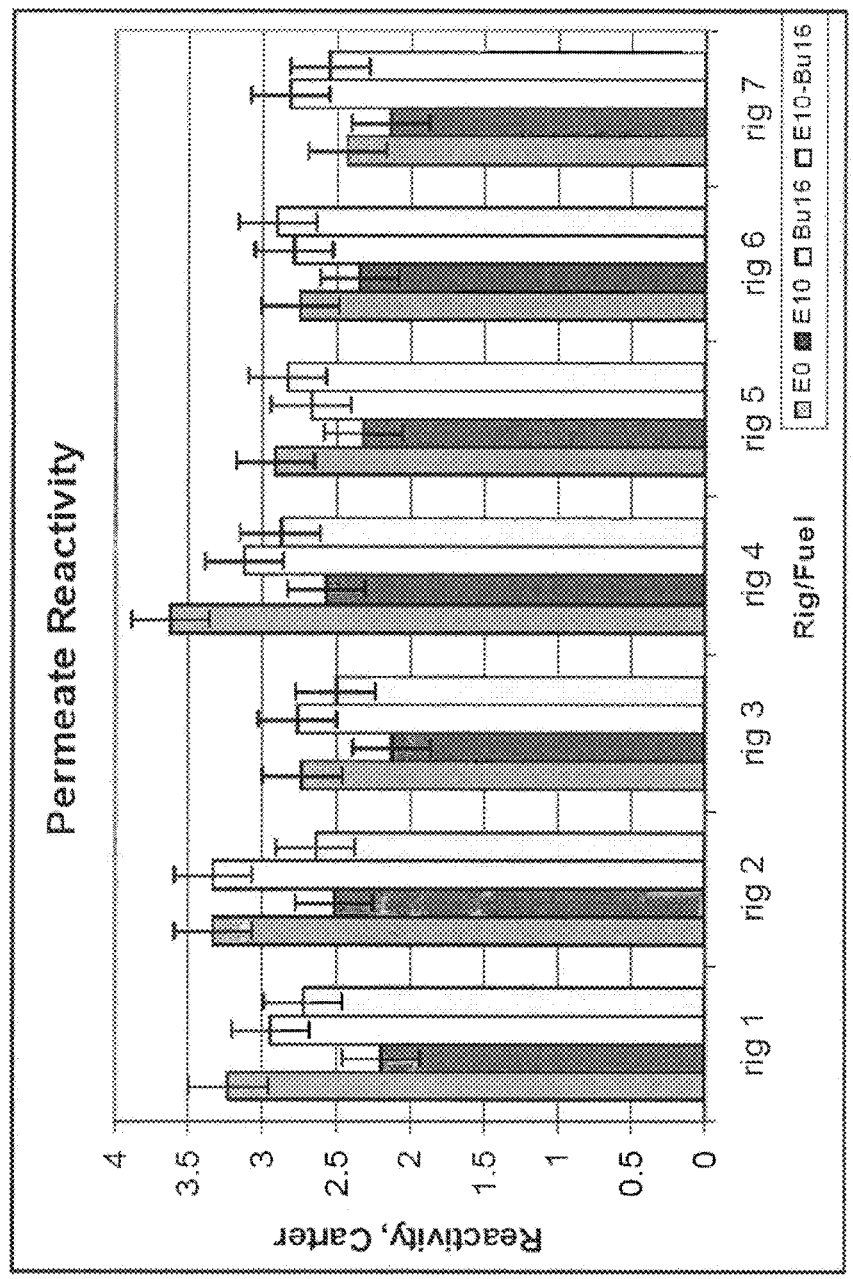
FIG. 27 shows the results for fleet average reactivity for individual rigs as described in the examples.

Individual rig results are shown in FIG. 27. Comparisons show that:

a. Isobutanol permeate reactivity is not significantly different from base fuel, E0 in all cases.

b. Mixed fuel, E10-Bu16, permeate reactivity is not different from E10 except in rig 6 and perhaps rig 1 (borderline, P=0.05).

Before running the 48 hours diurnal test, each rig is "stabilized" at 105° F. with a full tank of test fuel. The average reported stead-state permeation results (mg/hr) were analyzed using the following model $$\text{Steady-state permeation} = \text{constant} + \text{rig} + \text{ethanol presence}(y/n) + \text{isobutanol presence}(y/n) + \text{ethanol presence}(y/n)*\text{isobutanol presence}(y/n) + \text{rig}*\text{ethanol presence}(y/n).$$

Figure 28:
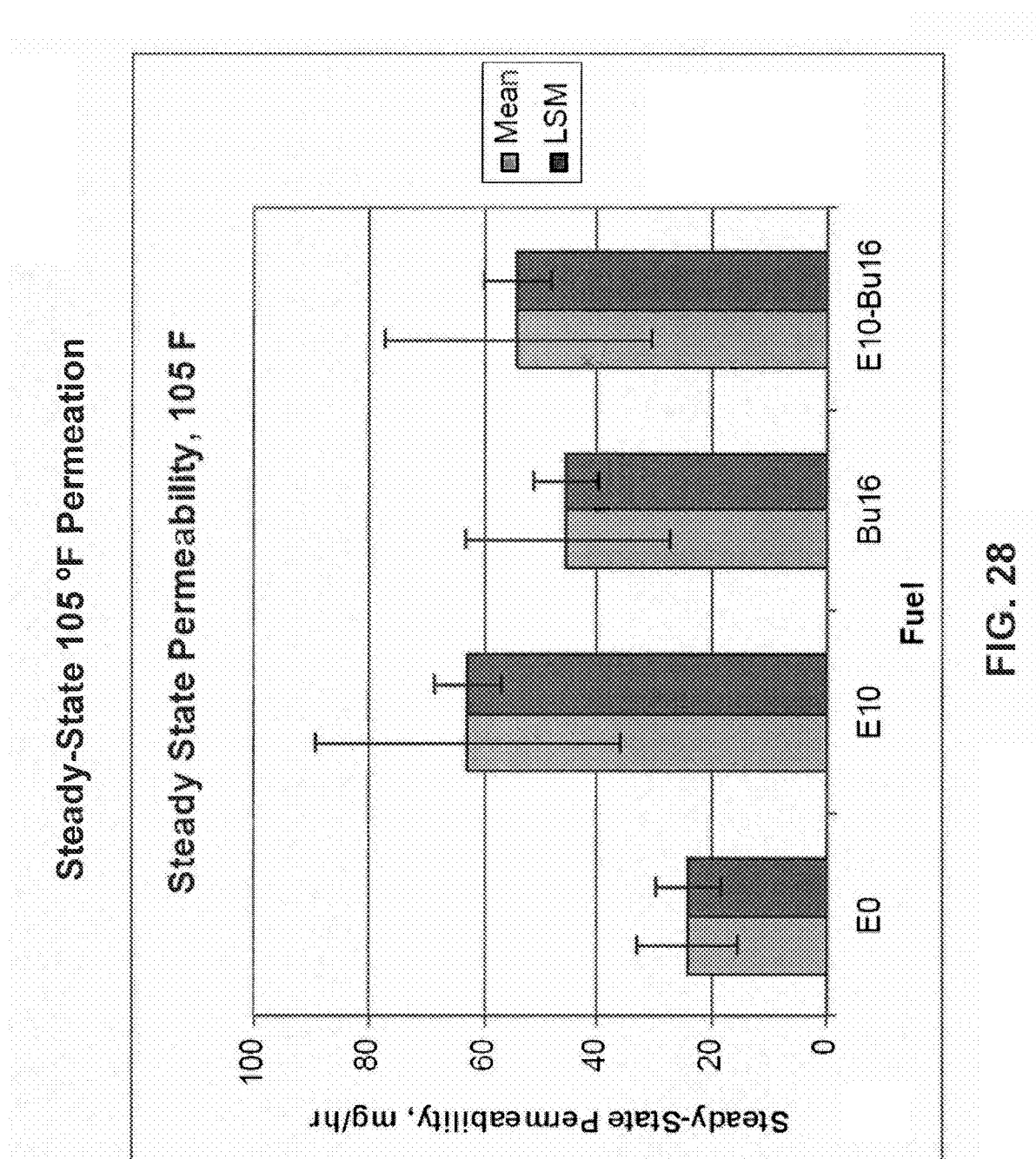
FIG. 28 shows steady state permeability results at 105° F. as described in the examples.

This is the same as the diurnal (48 hr) permeation with an added 2-factor interaction, rig*ethanol presence(y/n) that was found to be statistically significant. FIG. 28 shows the results which are parallel to the diurnal permeation results shown in FIGS. 10 and 20. As observed for the diurnal permeation, all the alcohol fuels were higher than the hydrocarbon base.

While individual rig responses are variable, the fleet average trends indicate that isobutanol decreases permeation emissions when added to ethanol fuels (FIG. 20). When comparing isobutanol fuel (Bu16) and ethanol fuel (E10) individually, the fleet average results indicate that the permeation emissions are lower with Isobutanol at equivalent oxygen content. In regards to ozone reactivity of the permeate, statistically, E10 was lower than all other fuels in the program and Bu16 was not statistically different from E0 or the 50:50 blend. On a mass basis, Bu16 produced lower permeation emissions than all other fuels with the exception of E0. The ozone forming potential of the Bu16 permeation emissions were the same or lower than E10 in all cases (FIG. 25).

A detailed speciation was conducted on the Diurnal permeation as well as the fuel itself. The top 20 species accounts for over 76% of the total permeate with the exception of Bu16 on Rig2. The results indicate that ethanol makes up a disproportionately higher concentration in the permeate relative to it's concentration in the fuel. Isobutanol on the other hand is about the same or half of the relative concentration in the fuel. Two dominant aromatic species in the permeate are toluene and benzene. The concentration of those two aromatic species appears to be relatively the same across all fuels and rigs. However, when examined on a mass basis, there is an increase in benzene emissions with ethanol blended fuels compared to Bu16. For toluene emissions, there is an increase with isobutanol blended fuels compared to E10. E0 produced the lowest aromatic emissions.

Thus, isobutanol does not increase permeation compared to ethanol (E10) on average for the fleet of 7 rigs. This also the result for each vehicle technology group (Tiers 3, 4, 5 vehicles). Further, there is no synergistic impact on permeation amount for mixing isobutanol gasoline with ethanol gasoline. Again the same result for fleet average and each vehicle technology group was observed. Isobutanol did not have a significantly different ozone reactivity compared to E0 (i.e. CARB all hydrocarbon gasoline) for fleet averages. However E10 gasoline (fleet average) had a significantly lower ozone reactivity compared to all the other fuels (i.e. E0, Bu16 and E0-Bu16 mix). However, no statistically significant ozone reactivity differences between fuels within each vehicle technology group were observed. Bu16 total potential ozone formation is not significantly different than E10.

What is claimed is:

1. A method of comparing a permeation emission for an alternative energy fuel to another alternative energy fuel or a fuel that is not an alternative energy fuel comprising:
    measuring a permeation emission obtained from operation of a fuel system on an alternative energy fuel comprising butanol at approximately sixteen percent (16%) by volume;
    measuring a permeation emission obtained from operation of a fuel system on another alternative energy fuel comprising ethanol at no more than about ten percent (10%) by volume;
    measuring a permeation emission obtained from operation of a fuel system on a fuel that is not an alternative energy fuel;
    comparing the permeation emissions obtained from operation of the fuel system on the alternative energy fuel comprising butanol, the alternative energy fuel comprising ethanol, and the fuel that is not an alternative energy fuel to evaluate whether the permeation emissions obtained from the operation of the fuel system on the alternative energy fuel comprising butanol contains permeation emissions equal to or less than the permeation emissions obtained from the operation of the fuel system on the alternative energy fuel comprising ethanol or the fuel that is not an alternative energy fuel.

2. The method of claim 1, wherein to pass the comparing the alternative energy fuel comprising butanol must have a negative value in comparison to the permeation emissions for the fuel that is not an alternative energy fuel.

3. The method of claim 1, wherein to pass the comparing the alternative energy fuel comprising butanol must have a negative value in comparison to the permeation emissions for the alternative fuel comprising ethanol.

4. The method of claim 1, wherein the permeation emissions for the fuel that is not an alternative energy fuel are based on a predicted model.

5. The method of claim 1, wherein butanol comprises isobutanol.

* * * * *